US008080371B2

(12) United States Patent
Ballinger et al.

(10) Patent No.: US 8,080,371 B2
(45) Date of Patent: Dec. 20, 2011

(54) MARKERS FOR ADDICTION

(75) Inventors: Dennis Ballinger, Menlo Park, CA (US); Karel Konvicka, San Francisco, CA (US); Laura Jean Bierut, St. Louis, MO (US); John Rice, St. Louis, MO (US); Frank Scott Saccone, St. Louis, MO (US); Anthony L. Hinrichs, St. Louis, MO (US); Alison M. Goate, St. Louis, MO (US); Jen Wang, Ballwin, MO (US)

(73) Assignee: The Washington University, St. Louis, MO (US)

( * ) Notice: Subject to any disclaimer, the term of this patent is extended or adjusted under 35 U.S.C. 154(b) by 18 days.

(21) Appl. No.: 11/681,177

(22) Filed: Mar. 1, 2007

(65) Prior Publication Data

US 2007/0258898 A1 Nov. 8, 2007

Related U.S. Application Data

(60) Provisional application No. 60/778,597, filed on Mar. 1, 2006, provisional application No. 60/811,318, filed on Jun. 6, 2006.

(51) Int. Cl.
*C12Q 1/68* (2006.01)
*C12P 19/34* (2006.01)
*C07H 21/04* (2006.01)

(52) U.S. Cl. ........ 435/6; 435/91.2; 536/24.33; 536/23.1

(58) Field of Classification Search ................ None
See application file for complete search history.

(56) References Cited

U.S. PATENT DOCUMENTS

| | | | | |
|---|---|---|---|---|
| 4,683,202 | A | * | 7/1987 | Mullis |
| 5,045,694 | A | * | 9/1991 | Beavis et al. |
| 5,202,561 | A | * | 4/1993 | Giessmann et al. |
| 5,468,613 | A | * | 11/1995 | Erlich et al. |
| 5,925,517 | A | * | 7/1999 | Tyagi et al. |
| 6,037,130 | A | * | 3/2000 | Tyagi et al. |
| 6,111,251 | A | * | 8/2000 | Hillenkamp |
| 6,150,097 | A | * | 11/2000 | Tyagi et al. |
| 6,174,670 | B1 | * | 1/2001 | Wittwer et al. |
| 6,342,355 | B1 | * | 1/2002 | Hacia et al. |
| 6,740,510 | B2 | * | 5/2004 | Kautzer et al. |
| 6,897,025 | B2 | * | 5/2005 | Cox et al. |
| 6,898,531 | B2 | * | 5/2005 | Sheehan et al. |
| 6,969,589 | B2 | * | 11/2005 | Patil et al. |
| 7,127,355 | B2 | * | 10/2006 | Cox et al. |
| 2003/0108919 | A1 | * | 6/2003 | Kautzer et al. |
| 2004/0023237 | A1 | * | 2/2004 | Patil et al. |
| 2004/0229224 | A1 | * | 11/2004 | Frazer et al. |
| 2004/0241657 | A1 | * | 12/2004 | Patil et al. |
| 2005/0003410 | A1 | * | 1/2005 | Frazer et al. |
| 2005/0007375 | A1 | * | 1/2005 | Yi |
| 2005/0019787 | A1 | * | 1/2005 | Berno et al. |
| 2006/0166224 | A1 | * | 7/2006 | Norviel |

FOREIGN PATENT DOCUMENTS

WO WO92/02638 * 2/1992

OTHER PUBLICATIONS

Langdahl, Bente et al. Osteoporotic fractures are assoicated with an 86 base pair repeat polymoprhism in the interleukin 1 receptor antagonist gene but not with polymoprhisms in the interleukin 1B gene. 2000. Journal of Bone and Mineral Research. vol. 15 No. 3 pp. 402-414.*
Wall, Jeffery et al. Haplotype blocks and linkage disequilbirium in the human genome. 2003. Nature Reviews Genetics. vol. 4 pp. 587-597.*
Arnhelm, N., et al., *C&EN*—36-47 (1990).*
Barrett ,J.C., et al., *Bioinformatics*—21(2):263-265 (2005).*
Barringer, K.J., et al., *Gene*—89:117-122 (1990).*
Beaucage, S.L., et al., *Tetrahedron Letts.*—22(20):1859-1862 (1981).*
Becker, J., et al., *Mol Gen Genet*—249:65-73 (1995).*
Benjamini, Y., et al., *J.R. Stat. Soc. B*—57(1):289-300 (1995).
Beuten, J., et al., *Am. J. Hum. Genet.*—76:859-864 (2005).
Beuten, J., et al., *Am. J. Med. Genet. B Neuropsychiatr. Genet.*—139:73-80 (2005).
Bierut, L.J. et al., *Hum. Mot. Genet.*—16(1):24-35 (2007).
Bierut, L.J., et al., *Am. J. Med. Genet.*—124A:19-27 (2004).
Bierut, L.J., et al., *Arch. Gen. Psychiatry*—55:982-988 (1998).
Blok, H.J., et al., *Mol Cell Probes*—11:187-194 (1997).
Bonnet, G., et al., *Proc. Natl. Acad. Sci. U.S.A.*—96:6171-6176 (1999).
Boustead. C, et al., *Pharmacogenetics*—7:411-414 (1997).
Breslau, N., et al., *Psychol. Med.*—34:323-333 (2004).
Breslau, N., et al., *Biol. Psychiatry*—55:69-76 (2004).
Breslau, N., et al., *Am. J. Public Health*—90:1122-1127 (2000).
Busby, V., et al., *Neuromolecular Med.*—5:133-146 (2004).
Butt, C.M., et al, *Alcohol. Clin. Exp. Res.*—27(5):733-742 (2003).
Butt, C.M., et al., *Behav. Neurosci.*—119(1):26-37 (2005).
CDC (2005) Annual smoking-attributable mortality, years of potential life lost, and productivity losses—United States, 1997-2001—*Morbidity & Mortality Weekly Report*—54:625-628.
CDC (2005) Cigarette smoking among adults—United States, 2004—*Morbidity & Mortality Weekly Report*—54:121-1124.
CDC (2004) Cigarette use among high school students—United States, 1991-2003—*Morbidity & Mortality Weekly Report*—53:499-502.
Carlson, C.S., et al., *Am. J. Hum. Genet.*—74:106-120 (2004).

(Continued)

*Primary Examiner* — Amanda Shaw

(57) ABSTRACT

Correlations between polymorphisms and addiction are provided. Methods of diagnosing, prognosing, and treating addiction are provided. Systems and kits for diagnosis, prognosis and treatment of addiction are provided. Methods of identifying addiction modulators are also described.

6 Claims, 27 Drawing Sheets

(10 of 27 Drawing Sheet(s) Filed in Color)

OTHER PUBLICATIONS

Carmelli, D., et al., *N. Engl. J. Med.*—327(12):829-833 (1992) Abstract Only.
Chee, M., et al., *Science*—274:610-614 (1996).
Cheng, S., et al., *Nature*—369:684-685 (1994).
Cholerton, S., et al., *Pharmacogenetics*—6:261-263 (1996).
Comings, D.E., et al., *Pharmacogenetics*—6:73-79(1996).
Corrigall, W.A., et al., *Brain. Res.*—653:278-284 (1994).
Craig, A.M., et al., *Trends Neurosci.*—29:8-20 (2006).
Cserzo, M., et al., *Protein Eng.*—10(6):673-676 (1997).
Dobelis, P., et al., *Mol. Pharmacol.*—62(2):334-342 (2002).
Dobson-Stone, C., et al., *Eur. J. Hum. Genet.*—10:773-781 (2002).
Ertekin-Taner, N., et al., *Hum. Mol. Genet.*—12,3133-3143 (2003).
Fang, X. ,et al. *J. Am. Chem. Soc.*—121:2921-2922 (1999).
Feng, Y., et al., *Am. J. Hum. Genet.*—75:112-121 (2004).
Zeng, Z., et al., *Cell*—127:621-633 (2006).
Fodor, P.A., *FASEB Journal*—11:A879 (1997).
Fodor, S.P.A. *Science*—277:393-395 (1997).
Gelernter, J. et al., *Am. J. Med. Genet. B Neuropsychiatr. Genet.*—128B:94-101 (2004).
Grant, B.F., et al., *Arch. Gen. Psychiatry*—61:1107-1115 (2004).
Greenbaum, L., et al., *Mol. Psychiatr.*—11:312-322 (2006).
Guatelli, J.C., et al., *Proc. Natl. Acad. Sci. USA*—87:1874-1878 (1990).
Heath, A.C., et al., *Addict. Behav.*—18:19-34 (1993).
Heatherton, T.F., et al., *Br. J. Addict.*—86:1119-1127 (1991).
Heatherton, T.F., et al., *Br. J. Addict.*—84:791-800 (1989).
Hegab, A.E., et al., *J. Med. Genet.*—41:(e27):1-7 (2004).
Hinds, D.A., et al., *Science*—307:1072-1 079 (2005).
Hinds, D.A., et al., *Am. J. Hum. Genet.*—74:317-325 (2004).
Hochberg, Y., et al., *Stat. Med.*—9:811-818 (1990).
Hsuih, T.C.H., et al., *J. Clin. Microbiol.*—34(3):501-507 (1996).
Hu, S., et al., *Mol. Psychiatry*—5:181-188 (2000).
Iacono, W.G., et al., *Arch. Gen. Psychiatry*—59,750-757 (2002).
Issaq, H.J., et al., *(Analytical Chemistry*—75:149A-155A (2003).
Jeulin, C., et al., *Am. J. Physiol. Lung Cell. Mol. Physiol.*—289:L636-L646 (2005).
Karadsheh, M. S., et al., *J. Neurochem.*—91:1138-1150 (2004).
Kostrikis, L.G., et al., *Science*—279:1228-1229 (1998).
Kwoh, D.Y., et al., *Proc. Natl. Acad. Sci. USA*—86:1173-1177 (1989).
Landegren, U., et al., *Science*—241, 1077-1080 (1988).
Lasser, K, et al., *Jama*—284(20):,2606-2610 (2000).
Laviolette,S.R., et al., *Nat. Rev. Neurosci.*—5:55-65 (2004) Abstract Only.
Leone, G., et al., *Nucleic Acids Res.*—26(9):2150-2155 (1998).
Lerman, C., et al., *Health Psychol.*—18(1):14-20 (1999).
Lerman, C., et al., *Mol. Psychiatry*—5: 189-192 (2000).
Lessov, C.N., et al., *Psychol. Med.*—34, 865-879 (2004).
Lewohl, J.M., et al., *Nat. Neurosci.*—2(12):1084-1090 (1999).
Li, M.D., et al., *BMC Genet.*—4(Suppl I):SI03:1-5 (2003).
Li, M.D., et al., *Hum. Mol. Genet.*—14:1211-1219 (2005).
Li, M.D., *Curr. Psychiatry. Rep.*—8:158-164 (2006).
Lindstrom, J.M., et al., *Ann. N.Y. Acad. Sci.*—998:41-52 (2003).
Liu, Q.R., et al., *Proc. Natl. Acad. Sci. U. S. A.*—102:11864-11869 (2005).
Lockhart, D.J., *Nature Medicine*—4:1235-1236 (1998).
Lomell, H., et al., *J. Clin. Chem.*—35:1826-1831 (1989).
Lowry, O. H., et al,. *J. Biol. Chem.*—193:265-275 (1951).
Ma, J.Z., et al., *Hum. Mol. Genet.*—14(12):1691-1698 (2005).
Madden, P.A., et al., *Behav. Genet.*—29(6):423-431 (1999).
Marks, M. J., et al., *J. Pharmacol. Exp. Ther.*—285(1):377-386 (1998).
Marras, S.A.E., et al., *Genet. Anal. Biomol. Eng.*—14:151-156 (1999).
Meksem, K., et al., *Mol. Gen. Genet.*—249:74-81 (1995).
Merikangas, K.R., et al., *Arch Gen Psychiatryi*—55:973-979 (1998).
Needham-VanDevanter, D.R., et al., *Nucleic Acids Res.*—12(15):6159-6168 (1984).
Pianezza, M.L., et al. Sellers,E.M., and Tyndale,RF. Nicotine metabolism defect reduces smoking. *Nature*—393:750 (1998).
Pritchard, J.K., et al., *Genetics Society of America*—155:945-959 (2000).
Roeder, K., et al., *Am. J. Hum. Genet.*—78, 243-252 (2006).
Saccone, S.F., et al., *Genet. Epidemiol.*—30:459-470 (2006).
Saccone, S.F., et al., *Hum. Mol. Genet.*—16(1):36-49 (2006).
Salminen, O., et al., *Mol. Pharmacol.*—65(6):1526-1535 (2004).
Sapolsky, R.J., et al., *Genetic Analysis: Biomolecular Engineering*—14:187-192 (1999).
Satagopan, J.M., et al., *Biometrics*—58:163-170 (2002).
(Service (1998) *Science* 282:396-401(1998).
Shields, P.G., et al., *Cancer Epidemiol. Biomarkers Prev.*—7:453-458 (1998).
Skol, A.D., et al., *Nat. Genet.*—38(2):209-213 (2006).
Sooknanan, R., et al., *Biotechnology*—13:563-564 (1995).
Sokol, D.L., et al., *Proc. Natl. Acad. Sci. U.S.A.*—95:11538-11543 (1998).
Spitz, M.R, et al., *J. Natl. Cancer. Inst.*—90(5):358-363 (1998).
Stein, L.D., et al., *Genome. Res.*—12:1599-1610 (2002).
Stitzel, J.A., et al., *Pharmacogenetics*—11:331-339 (2001).
Storey, J.D., *J. R. Statist. Soc. B*—64:479-498 (2002).
Storey, J.D., et al., *Proc. Natl. Acad. Sci.*—100(16):9440-9445 (2003).
Swan, G.E., et al., *Am. J. Med. Genet. B Neuropsychiatr. Genet.*—141B:354-360 (2006).
True, W.R., et al., *Arch. Gen. Psychiatry*—56:655-661(1999).
Tyagi, S., et al., *Nature Biotechnology*—14:303-308 (1996).
Tyagi, S., et al., *Nature Biotechnology*—16:49-53 (1998).
Van Brunt, J., *Biotechnology*—8:291-294 (1990).
Vernon, W.I., et al., *Biotechniques*—33(4):730, 732 & 734 (2002).
Vet, J.A.M., et al., *Proc. Natl. Acad. Sci. U.S.A.*—96:6394-6399 (1999).
Vos, P., et al., *Nucl. Acids Res.*—23(21):4407-4414 (1995).
Warren, C.W., et al., *Lancet*—367:749-753 (2006).
Wu, D.Y., et al., *Genomics*—4:560-569 (1989).
Zagranichnaya, T.K., *J Biol. Chem.*—280(33):29559-23569 (2005).
Zhang, N., et al., *Anal. Chem.*—71: 1138-1145 (1999).

\* cited by examiner

CHRNA5, Chromsome 15

KEETESGSGPKSSRNTLEAALDSIRYITRHIMKENDVREVVEDW human
KEETESGSGPKSSRNTLEAALDSVRCITRHIMKENDVREVVEDW chimpanzee
EQTGSGGPESSRNTMEAALDSIRYITRHIVKENAVREVVEDW Bolivian squirrel monkey
KEEARSSRGPRSSRNALEAALDSVRYITRHVMKETDVREVVEDW cattle
REEAESGAGPKSRNTLEAALDCIRYITRHVVKENDVREVVEDW rat
REEAEKDGGPKSRNTLEAALDCIRYITRHVVKENDVREVVEDW mouse
KEEKGNMSGSESSRNTLEAALDSIRYITRHVMKENEVREVVEDW Gallus gallus (chicken)

D: Aspartic Acid (GAU, GAC)
N: Asparagine (AAU, AAC)

Fig. 23

MARKERS FOR ADDICTION

CROSS-REFERENCE TO RELATED APPLICATIONS

The present application claims priority to U.S. Ser. No. 60/778,597 filed Mar. 1, 2006, and U.S. Ser. No. 60/811,318 filed Jun. 6, 2006, each of which is herein incorporated by reference in its entirety for all purposes.

STATEMENT OF GOVERNMENT INTEREST

This invention was made with government support under NIH Contract No. HHSN271200477471C. This work is also supported in part by NIH grants CA89392 from the National Cancer Institute, DA12854 and DA015129 from the National Institute on Drug Abuse, and the contract N01DA-0-7079 from NIDA. As such, the United States government has certain rights in the invention.

FIELD OF THE INVENTION

The present invention is in the field of addiction diagnosis, prognosis, and treatment. The invention relates to correlations between polymorphisms and addiction as well as systems and kits for diagnosis, prognosis and treatment of addiction and methods of identifying addiction modulators.

APPENDIX

This application incorporates by reference herein in its entirety the following file submitted on duplicate compact disks OR alternatively submitted electronically with this submission via EFS:

| File Name | Date Created | Size |
| --- | --- | --- |
| TopSNPs.txt | Mar. 1, 2006 | 1.754 MB |

The content of this file is as follows:
TopSNPs.txt:
  This file contains a table, termed Table 1 in the specification of the instant application submitted herewith, that contains information about the SNPs found to be associated with nicotine addiction in the Examples herein, e.g., Examples 1, 2, 3, etc and that is some embodiments can be considered to be related to sequences.
In the table described above, the first row is a header row with the column names. The columns are as follows:
1. SNP_ID: Perlegen internal SNP identifier.
2. refsnp_ID: SNP identification number from dbSNP (NCBI) for each variant. This is the reference number according to dbSNP database established and maintained by NCBI of the National Library of Medicine at the National Institute of Health)
3. nda01_all_result.CASES_P: case allele frequency for all samples
4. nda01_all_result.CNRLS_P: control allele frequency for all samples
5. nda01_all_result.DELTA_P: delta allele frequency for all samples
6. nda01_all_result.CALL_RATE: call rate for all samples
7. nda01_all_result.HWE_P_VALUE_CTRLS: Hardy-Weinberg equilibrium (HWE) p-value for the controls
8. nda01_all result.GC_TREND_SCORE_P: genomic control-corrected trend score p-value for all samples
9. nda01_all_result.TREND_SCORE_FWER: familywise error rate computed from candidate gene trend scores for all samples
10. nda01_all_result_sex_strat.TREND_SCORE_P_SEX_STRAT: gender-stratified trend score p-value for all samples
11. nda01_regression_result.ALL_GLM_P_VALUE: logistic regression on case/control ANOVA p-value for all samples
12. nda01_regression_result.ALL_LM_P_VALUE: linear regression on FTND score ANOVA p-value for all samples
13. nda01_ig_result.CASES_P: case allele frequency for pooled samples
14. nda01_ig_result.CTRLS_P: control allele frequency for pooled samples
15. nda01_ig_result.DELTA_P: delta allele frequency for pooled samples
16. nda01_ig_result.CALL_RATE: call rate in pooled samples
17. nda01_ig_result.HWE_P_VALUE_CTRLS: HWE p-value for the controls in the pooled samples
18. nda01_ig_result.TREND_SCORE_P: uncorrected p-value for the trend score for the pooled samples
19. nda01_ig_result_sex_strat.TREND_SCORE_P_SEX_STRAT: gender-stratified trend score p-value for the pooled samples
20. nda01_regression_result.IG_GLM_P_VALUE: logistic regression on case/control ANOVA p-value for the pooled samples
21. nda01_regression_result.IG_LM_P_VALUE: linear regression on FTND score ANOVA p-value for the pooled samples
22. nda01_rep_result.CASES_P: case allele frequency for the validation samples
23. nda01_rep_result.CTRLS_P: control allele frequency for the validation samples
24. nda01_rep_result.DELTA_P: delta allele frequency for the validation samples
25. nda01_rep_result.CALL_RATE: call rate in validation samples
26. nda01_rep_result.HWE_P_VALUE_CTRLS: HWE p-value for the controls in the validation samples
27. nda01_rep_result.GC_TREND_SCORE_P: genomic control-corrected trend score p-value for the validation samples
28. nda01_rep_result_sex_strat.TREND_SCORE_P_SEX_STRAT: gender-stratified trend score p-value for the validation samples
29. nda01_regression_result.REP_GLM_P_VALUE: logistic regression on case/control ANOVA p-value for the validation samples
30. nda01_regression_result.REP_LM_P_VALUE: linear regression on FTND score ANOVA p-value for the validation samples
31. CHROMOSOME_ID: chromosome where the SNP is mapped in NCBI Build 35 of the human genome
32. contig: contig on which the SNP is mapped in NCBI Build 35 of the human genome
33. POSITION: position on the chromosome where the SNP is mapped
34. gene_name: gene symbol for a gene near or within which the SNP is mapped 35. gene_hyperlink: indicated gene can be found in the NCBI GENE database
36. HIT_TYPE: where the SNP lies in relation to the gene, e.g., upstream, downstream, intron, exon, etc.
37. SYNONYMOUS: whether the SNP alleles cause a synonymous ("yes") or non-synonymous ("no") change in the gene sequence
38. is_candidate_region: 1 if SNP is selected from candidate gene region SNPs; 0 if SNP is selected from analysis of pooled SNPs
39. comments: additional comments regarding the SNP

LENGTHY TABLES

The patent contains a lengthy table section. A copy of the table is available in electronic form from the USPTO web site (http://seqdata.uspto.gov/?pageRequest=docDetail&DocID=US08080371B2). An electronic copy of the table will also be available from the USPTO upon request and payment of the fee set forth in 37 CFR 1.19(b)(3).

The machine format for the duplicate compact disks is IBM-PC, and the operating system compatibility is MS-Windows.

BACKGROUND OF THE INVENTION

The impact of nicotine addiction in terms of morbidity, mortality, and economic costs to society is enormous. Tobacco kills more than 430,000 U.S. citizens each year, more than alcohol, cocaine, heroin, homicide, suicide, car accidents, fire, and AIDS combined. Tobacco use is the leading preventable cause of death in the United States.

Economically, an estimated $80 billion of total U.S. health care costs each year is attributable to smoking. However, this cost is well below the total cost to society because it does not include burn care from smoking-related fires, perinatal care for low-birth-weight infants of mothers who smoke, and medical care costs associated with disease caused by secondhand smoke. Taken together, the direct and indirect costs of smoking are estimated at $138 billion per year.

Nicotine is one of thousands of chemicals found in the smoke from tobacco products such as cigarettes, cigars, pipes and smokeless tobacco products, such as snuff and chewing tobacco. Nicotine is one of the most frequently used addictive drugs. First identified in the early 1800s, nicotine is the primary component in tobacco that acts on the brain, and has been shown to have a number of complex and sometimes unpredictable effects on the brain and the body.

Addiction is characterized by compulsive drug-seeking and use, even in the face of negative health consequences. The majority of cigarette smokers identify tobacco as harmful and express a desire to reduce or stop using it, but less than 7 percent of the nearly 35 million of those who make a serious attempt to quit each year succeed. Several factors also serve as determinants for first use and, ultimately, addiction, such as its high level of availability, the small number of legal and social consequences of tobacco use, and the sophisticated marketing and advertising methods used by tobacco companies.

Research has shown how nicotine increases the levels of dopamine in the brain circuitry that regulates feelings of pleasure, the so-called reward pathways, and this is of primary importance to its addictive nature. Nicotine's pharmacokinetic properties have been found also to enhance its abuse potential. Cigarette smoking produces a rapid distribution of nicotine to the brain, with drug levels peaking within 10 seconds of inhalation. The acute effects of nicotine dissipate in a few minutes, causing the smoker to continue dosing frequently throughout the day to maintain the drug's pleasurable effects and prevent withdrawal.

SUMMARY OF THE INVENTION

The present invention provides a number of new genetic correlations between nicotine addiction and various polymorphic alleles, providing the basis for early detection of susceptible individuals, as well as an improved understanding of nicotine addiction and related disorders at the molecular and cellular level. These and other features of the invention will be apparent upon review of the following.

Accordingly, this invention provides previously unknown correlations between various polymorphisms and addiction phenotypes, e.g., susceptibility to nicotine addiction. The detection of these polymorphisms (or loci linked thereto), accordingly, provides robust and precise methods and systems for identifying patients that are at risk for nicotine addiction and related disorders. In addition, the identification of these polymorphisms provides high-throughput systems and methods for identifying modulators of addiction phenotypes. Table 1 provides descriptions of the polymorphisms. Descriptions of the polymorphisms also include a polymorphism of Table 21, a polymorphism of an alpha 5 nicotinic receptor gene, rs16969968 or a polymorphism in linkage disequilibrium with such or any haplotype comprising such as illustrated in FIG. 22, a polymorphism of Table 17, a polymorphism of Table 18, a polymorphism of NRXN1 of Table 18, a polymorphism of VPS13A of Table 18, a polymorphism of VPS13A, a polymorphism of TRPC7, a polymorphism of CTNNA3, a polymorphism of CLCA1, a polymorphism of Table 6, a polymorphism of CHRNB3 and/or CHRNA3, a polymorphism of a gene selected from CHRNB3, CHRNA3, KCNJ6, CHRNA5, GABRA4, CHRNA3, and PIP5K2A, a polymorphism selected from rs6474413, rs10958726, rs578766, rs6517442, rs16969968, rs3762611, rs1051730 and rs10508649, or a polymorphism of Table 9.

Accordingly, in a first aspect, methods of identifying an addiction phenotype for an organism or biological sample derived therefrom are provided. The method includes detecting, in the organism or biological sample, a polymorphism of a gene or at a locus closely linked thereto. Example genes include those listed in Table 1, in which the polymorphism is associated with an addiction phenotype. Similarly, detecting a polymorphism of Table 1, or a locus closely linked thereto, can be used to identify a polymorphism associated with an addiction phenotype. In either case, presence of the relevant polymorphism is correlated to an addiction phenotype, thereby identifying the relevant addiction phenotype. Any of the phenotypes related to addiction can constitute an addiction phenotype, e.g., the phenotype can include an increased susceptibility to nicotine addiction, etc. Such aspects also include wherein the polymorphisms a polymorphism of Table 21, a polymorphism of an alpha 5 nicotinic receptor gene, rs16969968 or a polymorphism in linkage disequilibrium with such or any haplotype comprising such as illustrated in FIG. 22, a polymorphism of Table 17, a polymorphism of Table 18, a polymorphism of NRXN1 of Table 18, a polymorphism of VPS13A of Table 18, a polymorphism of VPS13A, a polymorphism of TRPC7, a polymorphism of CTNNA3, a polymorphism of CLCA1, a polymorphism of Table 6, a polymorphism of CHRNB3 and/or CHRNA3, a polymorphism of a gene selected from CHRNB3, CHRNA3, KCNJ6, CHRNA5, GABRA4, CHRNA3, and PIP5K2A, a polymorphism selected from rs6474413, rs10958726, rs578766, rs6517442, rs16969968, rs3762611, rs1051730 and rs10508649, or a polymorphism of Table 9.

The organism or the biological sample can be, or can be derived from, a mammal. For example, the organism can be a human patient, or the biological sample can be derived from a human patient (blood, lymph, skin, tissue, saliva, primary or secondary cell cultures derived therefrom, etc.).

Detecting the polymorphism can include amplifying the polymorphism or a sequence associated therewith and detecting the resulting amplicon. For example, amplifying the polymorphism can include admixing an amplification primer or amplification primer pair with a nucleic acid template isolated from the organism or biological sample. The primer or primer pair is typically complementary or partially complementary to at least a portion of the gene or other polymorphism, or to a proximal sequence thereto, and is capable of initiating nucleic acid polymerization by a polymerase on the nucleic acid template. The amplification can also include extending the primer or primer pair in a DNA polymerization reaction using a polymerase and the template nucleic acid to generate the amplicon. The amplicon can be detected by hybridizing the amplicon to an array, digesting the amplicon with a restriction enzyme, real-time PCR analysis, sequencing of the amplicon, or the like. Optionally, amplification can include performing a polymerase chain reaction (PCR), reverse transcriptase PCR (RT-PCR), or ligase chain reaction (LCR) using nucleic acid isolated from the organism or biological sample as a template in the PCR, RT-PCR, or LCR. Optionally, amplification can include performing a whole-genome amplification, such as that described in, e.g., U.S. Ser. No. 11/173,309, filed Jun. 30, 2005, entitled "Hybridization of Genomic Nucleic Acid without Complexity Reduction." Other formats can include allele specific hybridization, single nucleotide extension, or the like.

The polymorphism can be any detectable polymorphism, e.g., a SNP. For example, the allele can be any of those noted in Table 1. The alleles can positively correlate to one or more addiction phenotypes, or can correlate negatively. Examples of each are described in Table 1. Additional examples include a polymorphism of Table 21, a polymorphism of an alpha 5 nicotinic receptor gene, rs16969968 or a polymorphism in linkage disequilibrium with such or any haplotype comprising such as illustrated in FIG. 22, a polymorphism of Table 17, a polymorphism of Table 18, a polymorphism of NRXN1 of Table 18, a polymorphism of VPS13A of Table 18, a polymorphism of VPS13A, a polymorphism of TRPC7, a polymorphism of CTNNA3, a polymorphism of CLCA1, a polymorphism of Table 6, a polymorphism of CHRNB3 and/or CHRNA3, a polymorphism of a gene selected from CHRNB3, CHRNA3, KCNJ6, CHRNA5, GABRA4, CHRNA3, and PIP5K2A, a polymorphism selected from rs6474413, rs10958726, rs578766, rs6517442, rs16969968, rs3762611, rs1051730 and rs10508649, or a polymorphism of Table 9

Polymorphisms closely linked to the genes listed in Table 1, and/or any polymorphism of Table 1 can be used as markers for an addiction phenotype. Such closely linked markers are typically about 20 cM or less, e.g., 15 cM or less, often 10 cM or less and, in certain preferred embodiments, 5 cM or less from the gene or other polymorphism of interest (e.g., an allelic marker locus in Table 1). The linked markers can, of course be closer than 5 cM, e.g., 4, 3, 2, 1, 0.5, 0.25, 0.1 cM or less from the gene or marker locus of Table 1. In general, the closer the linkage (or association), the more predictive the linked marker is of an allele of the gene or given marker locus (or association). Here too, other polymorphisms are optionally used, e.g., a polymorphism of Table 21, a polymorphism of an alpha 5 nicotinic receptor gene, rs16969968 or a polymorphism in linkage disequilibrium with such or any haplotype comprising such as illustrated in FIG. 22, a polymorphism of Table 17, a polymorphism of Table 18, a polymorphism of NRXN1 of Table 18, a polymorphism of VPS13A of Table 18, a polymorphism of VPS13A, a polymorphism of TRPC7, a polymorphism of CTNNA3, a polymorphism of CLCA1, a polymorphism of Table 6, a polymorphism of CHRNB3 and/or CHRNA3, a polymorphism of a gene selected from CHRNB3, CHRNA3, KCNJ6, CHRNA5, GABRA4, CHRNA3, and PIP5K2A, a polymorphism selected from rs6474413, rs10958726, rs578766, rs6517442, rs16969968, rs3762611, rs1051730 and rs10508649, or a polymorphism of Table 9.

In one typical embodiment, correlating the polymorphism is performed by referencing a look up table that comprises correlations between alleles of the polymorphism and the phenotype. This table can be, e.g., a paper or electronic database comprising relevant correlation information. In one aspect, the database can be a multidimensional database comprising multiple correlations and taking multiple correlation relationships into account, simultaneously. Accessing the look up table can include extracting correlation information through a table look-up or can include more complex statistical analysis, such as principle component analysis (PCA), heuristic algorithms that track and/or update correlation information (e.g., neural networks), hidden Markov modeling, or the like.

Correlation information is useful for determining susceptibility (e.g., patient susceptibility to addiction, e.g., nicotine addiction), and prognosis (e.g., likelihood that conventional methods to quit smoking will be effective in light of patient genotype).

Kits that comprise, e.g., probes for identifying the markers herein, e.g., packaged in suitable containers with instructions for correlating detected alleles to a addiction phenotype, e.g., increased susceptibility to addiction, etc. are a feature of the invention as well.

In an additional aspect, methods of identifying modulators of an addiction phenotype are provided. The methods include contacting a potential modulator to a gene or gene product, such as a gene product corresponding to those listed in Table 1, and/or any gene product in Table 1, and/or a gene corresponding to any of these gene products. An effect of the potential modulator on the gene or gene product is detected, thereby identifying whether the potential modulator modulates the addiction phenotype. All of the features described above for the alleles, genes, markers, etc., are applicable to these methods as well. Such methods also include polymorphisms such as a polymorphism of Table 21, a polymorphism of an alpha 5 nicotinic receptor gene, rs16969968 or a polymorphism in linkage disequilibrium with such or any haplotype comprising such as illustrated in FIG. 22, a polymorphism of Table 17, a polymorphism of Table 18, a polymorphism of NRXN1 of Table 18, a polymorphism of VPS13A of Table 18, a polymorphism of VPS13A, a polymorphism of TRPC7, a polymorphism of CTNNA3, a polymorphism of CLCA1, a polymorphism of Table 6, a polymorphism of CHRNB3 and/or CHRNA3, a polymorphism of a gene selected from CHRNB3, CHRNA3, KCNJ6, CHRNA5, GABRA4, CHRNA3, and PIP5K2A, a polymorphism selected from rs6474413, rs10958726, rs578766, rs6517442, rs16969968, rs3762611, rs1051730 and rs10508649, or a polymorphism of Table 9.

Effects of interest for which one may screen include: (a) increased or decreased expression of any gene of Table 1, and/or any protein encoded by these genes, in the presence of the modulator; (b) a change in the timing or location of expression of any gene of Table 1, and/or any protein encoded by these genes, in the presence of the modulator; (c) a change in any activity of any gene product encoded by any gene of Table 1, in the presence of the modulator; and/or (d) a change in localization of proteins encoded by the genes in Table 1 in the presence of the modulator. Here too the polymorphisms can comprise a polymorphism of Table 21, a polymorphism of an alpha 5 nicotinic receptor gene, rs16969968 or a polymorphism in linkage disequilibrium with such or any haplotype comprising such as illustrated in FIG. 22, a polymorphism of Table 17, a polymorphism of Table 18, a polymorphism of NRXN1 of Table 18, a polymorphism of VPS13A of Table 18, a polymorphism of VPS13A, a polymorphism of TRPC7, a polymorphism of CTNNA3, a polymorphism of CLCA1, a polymorphism of Table 6, a polymorphism of CHRNB3 and/or CHRNA3, a polymorphism of a gene selected from CHRNB3, CHRNA3, KCNJ6, CHRNA5, GABRA4, CHRNA3, and PIP5K2A, a polymorphism selected from rs6474413, rs10958726, rs578766, rs6517442, rs16969968, rs3762611, rs1051730 and rs10508649, or a polymorphism of Table 9.

The invention also includes kits for treatment of a addiction phenotype. In one aspect, the kit comprises a modulator identified by the method above and instructions for administering the compound to a patient to treat the addiction phenotype.

In an additional aspect, systems for identifying an addiction phenotype for an organism or biological sample derived therefrom are provided. Such systems include, e.g., a set of marker probes and/or primers configured to detect at least one allele of one or more gene or linked locus associated with the addiction phenotype, wherein the gene comprises or encodes any gene or gene product of Table 1. Typically, the set of marker probes or primers can include or detect a nucleotide sequence of Table 1, or an allele closely linked thereto. The system typically also includes a detector that is configured to detect one or more signal outputs (e.g., light emissions) from the set of marker probes and/or primers, or an amplicon produced from the set of marker probes and/or primers, thereby identifying the presence or absence of the allele. System instructions that correlate the presence or absence of the allele with the predicted addiction phenotype, thereby identifying the addiction phenotype for the organism or biological sample derived therefrom are also a feature of the system. The instructions can include at least one look-up table that includes a correlation between the presence or absence of the one or more alleles and the addiction predisposition. The system can further include a sample, which is typically derived from a mammal, including e.g., a genomic DNA, an amplified genomic DNA, a cDNA, an amplified cDNA, RNA, or an amplified RNA. The systems herein can also include a polymorphism of Table 21, a polymorphism of an alpha 5 nicotinic receptor gene, rs16969968 or a polymorphism in linkage disequilibrium with such or any haplotype comprising such as illustrated in FIG. 22, a polymorphism of Table 17, a polymorphism of Table 18, a polymorphism of NRXN1 of Table 18, a polymorphism of VPS13A of Table 18, a polymorphism of VPS13A, a polymorphism of TRPC7, a polymorphism of CTNNA3, a polymorphism of CLCA1, a polymorphism of Table 6, a polymorphism of CHRNB3 and/or CHRNA3, a polymorphism of a gene selected from CHRNB3, CHRNA3, KCNJ6, CHRNA5, GABRA4, CHRNA3, and PIP5K2A, a polymorphism selected from rs6474413, rs10958726, rs578766, rs6517442, rs16969968, rs3762611, rs1051730 and rs10508649, or a polymorphism of Table 9.

It will be appreciated that the methods, systems and kits above can all be used together in various combinations and that features of the methods can be reflected in the systems and kits, and vice-versa.

BRIEF DESCRIPTION OF THE DRAWINGS

The patent or application file contains at least one drawing executed in color. Copies of this patent or patent application with color drawing(s) will be provided by the Patent and Trademark Office upon request and payment of the necessary fee.

FIG. 23 shows comparative sequence analysis of the alpha 5 nicotinic receptor across species. The human sequence is designated SEQ ID NO:8, the chimpanzee sequence is designated SEQ ID NO:9, the Bolivian squirrel monkey sequence is designated SEQ ID NO:10, the cattle sequence is designated SEQ ID NO:11, the rat sequence is designated SEQ ID NO:12, the mouse sequence is designated SEQ ID NO:13, the Gallus gallus (chicken) sequence is designated SEQ ID NO:14.

DETAILED DESCRIPTION

Figure 1:
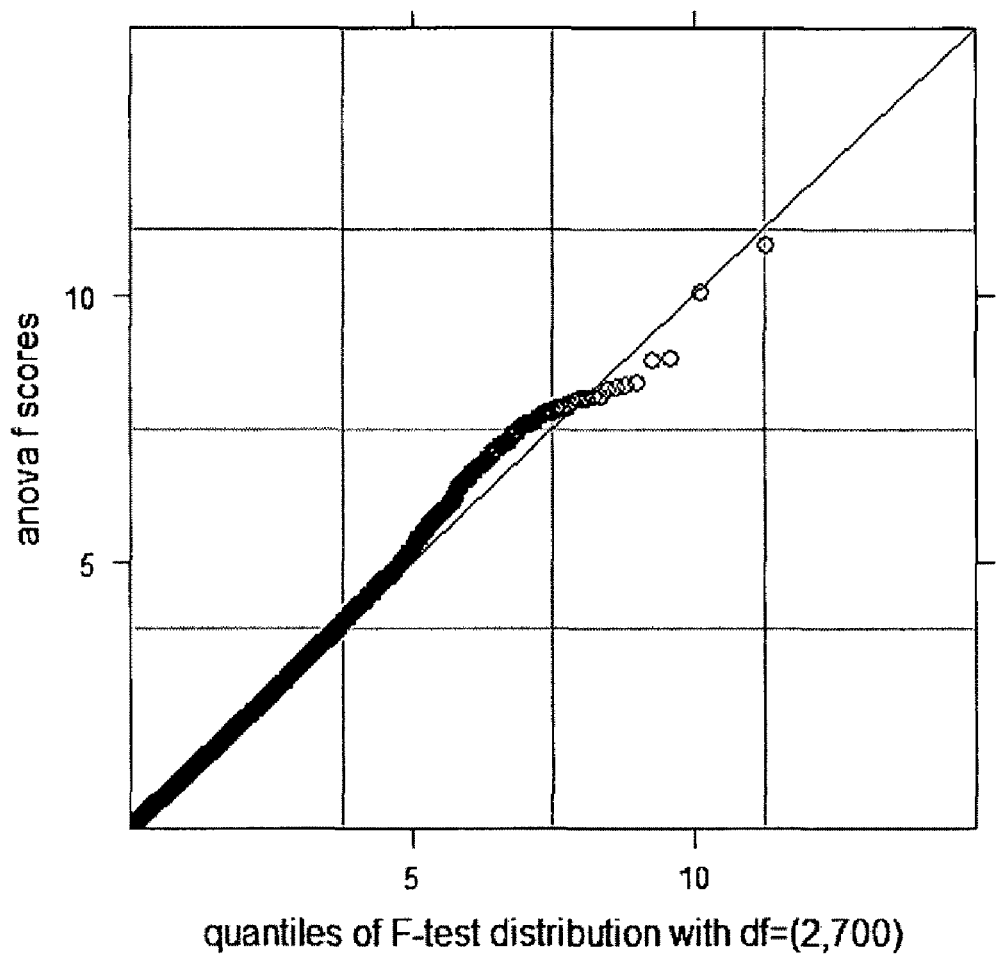
FIGS. 1-6 show Q-Q plots for round 1 sets in Example 1.
Figure 2:
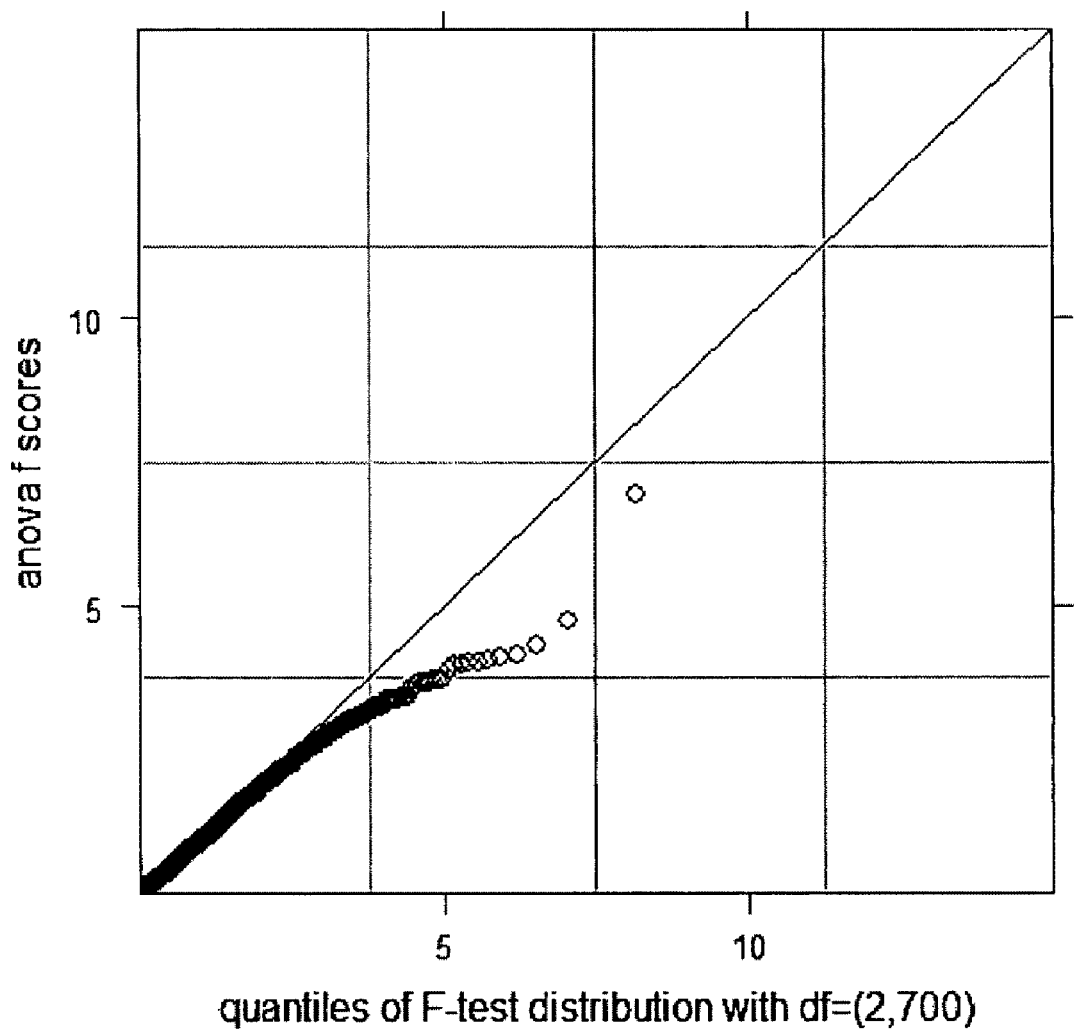
Figure 3:
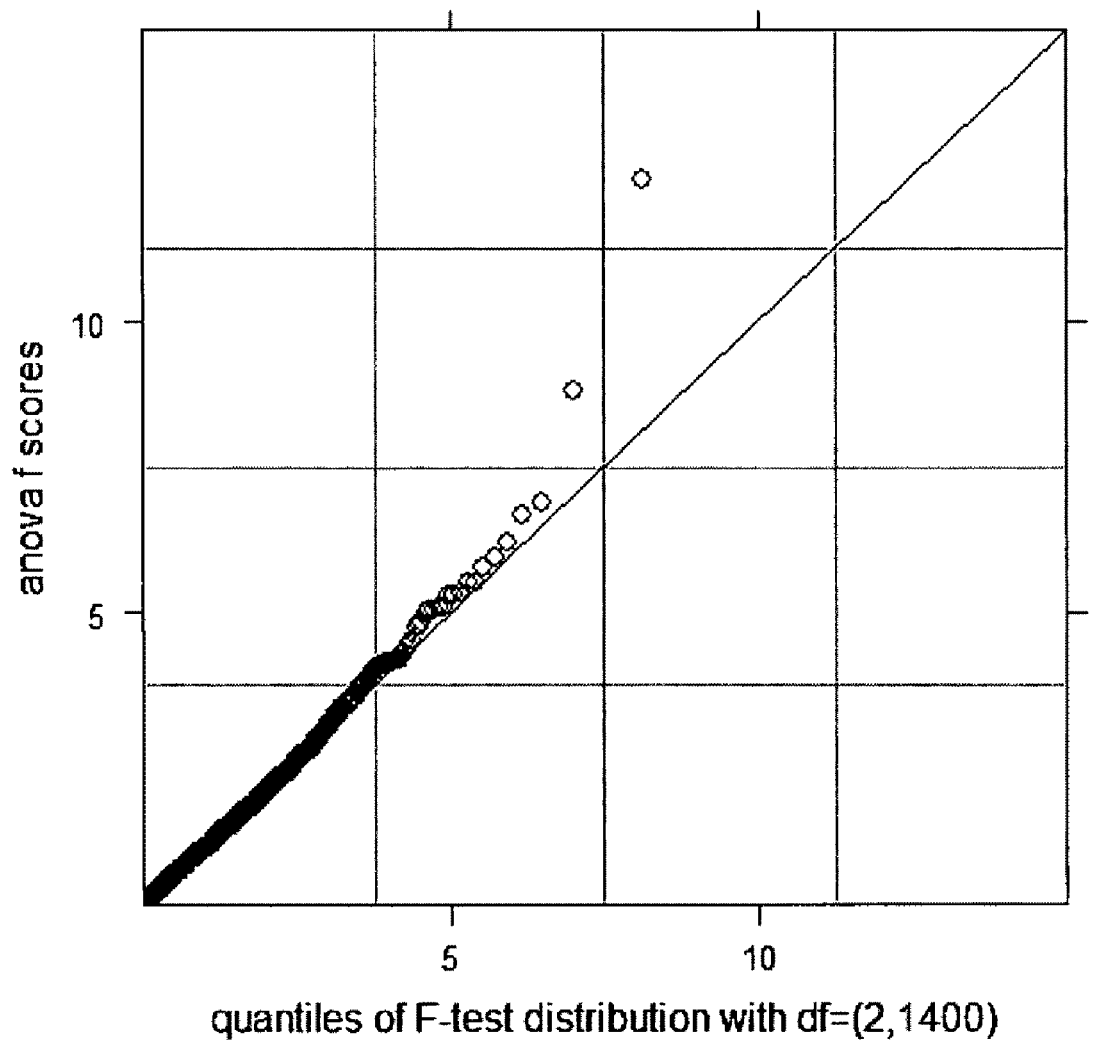
Figure 4:
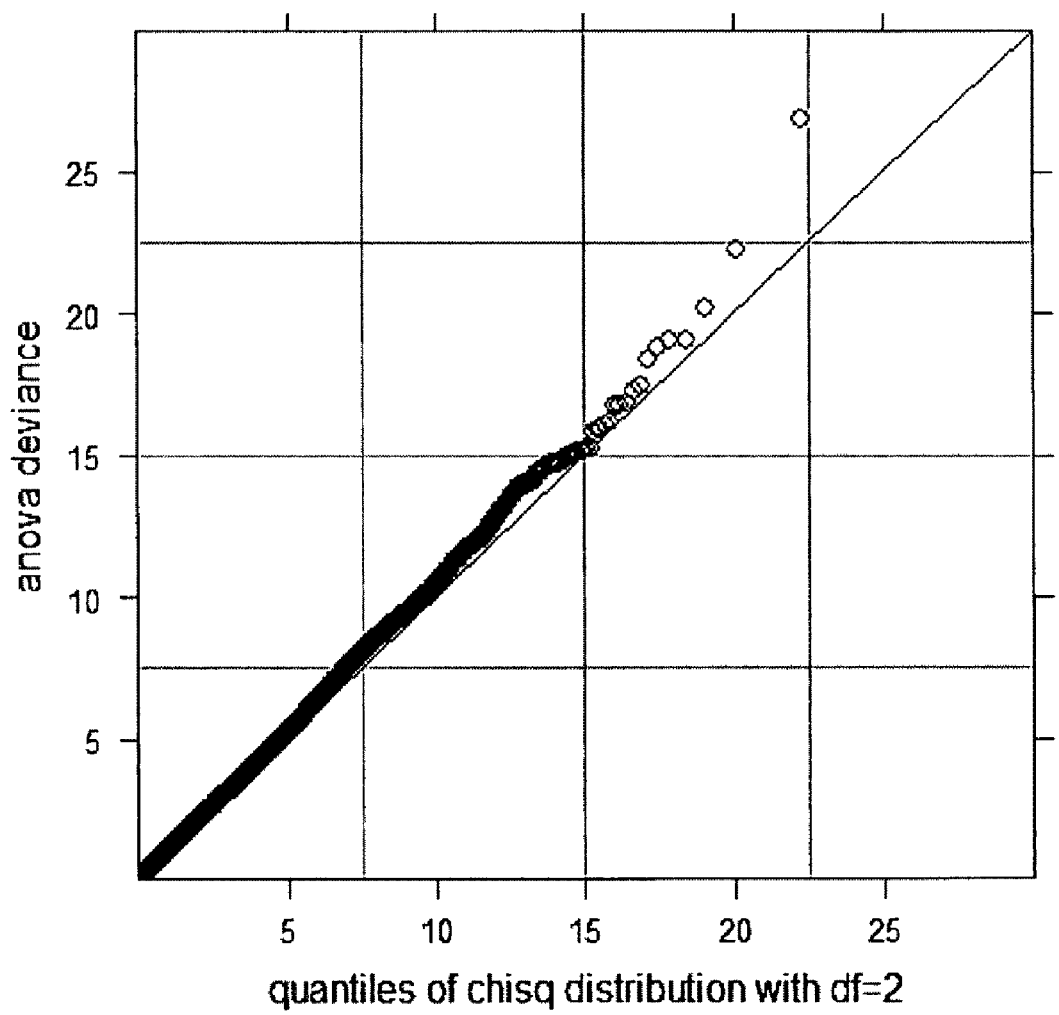
Figure 5:
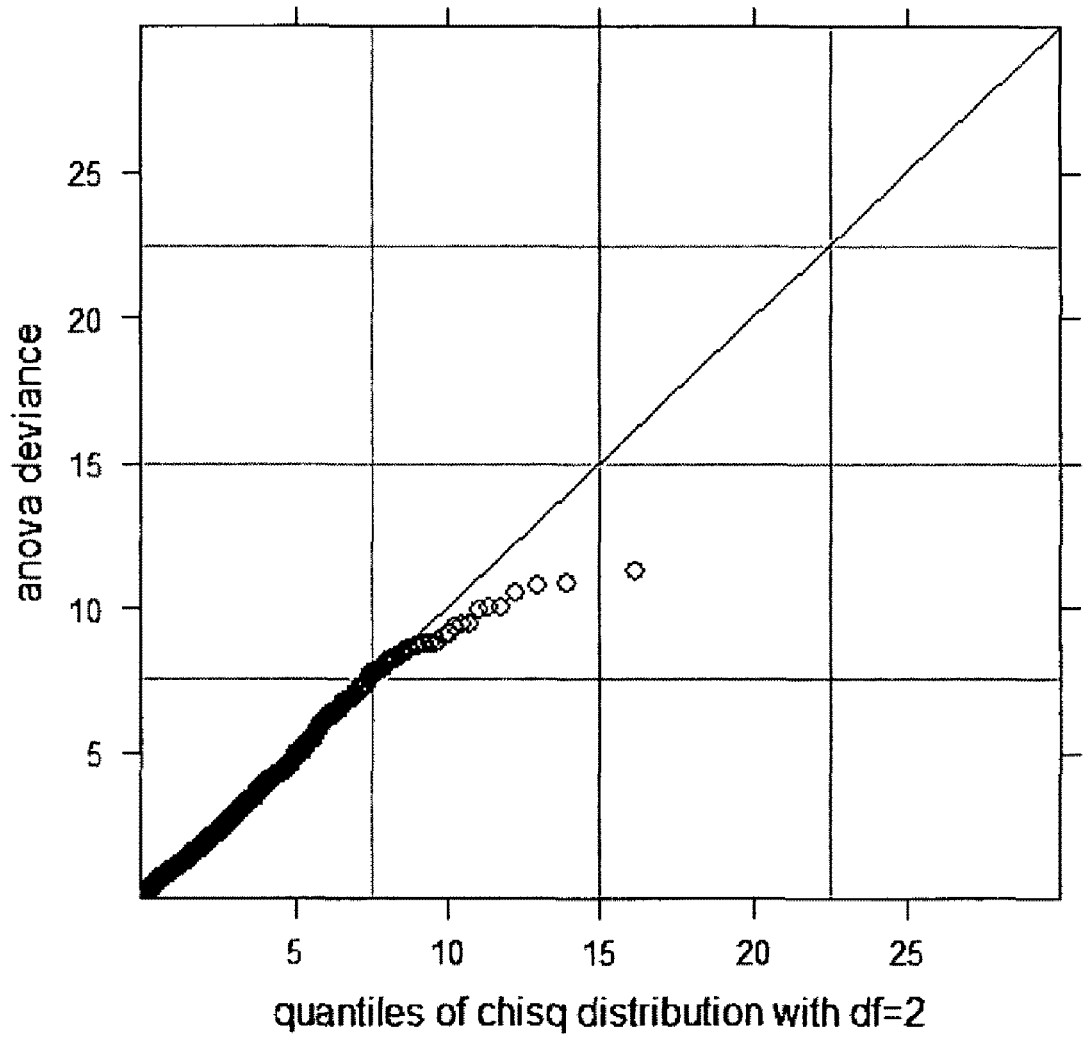
Figure 6:
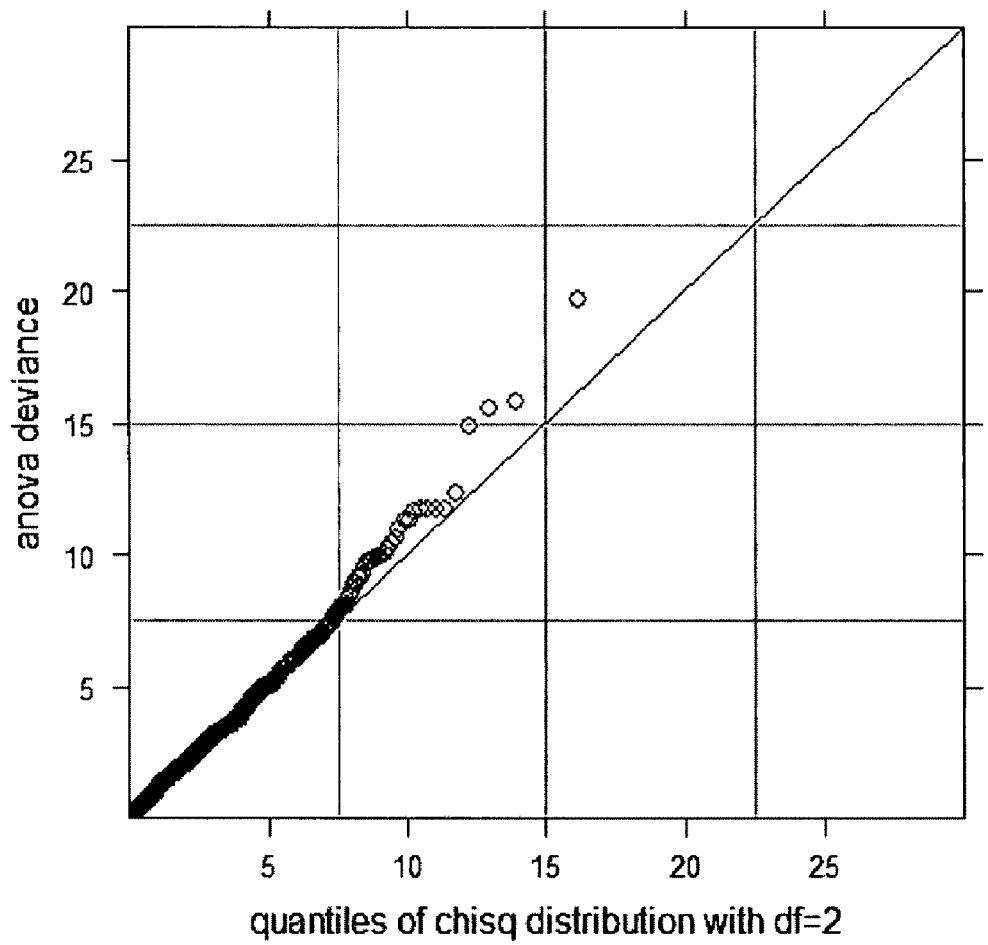

The present invention provides correlations between polymorphisms in or proximal to the genes or loci in Table 1 and addiction phenotypes. Thus, detection of particular polymorphisms in these loci, genes or gene products (e.g., RNA or protein products) provides methods for identifying patients that have or are at risk for addiction, e.g., nicotine addiction, etc. Systems for detecting and correlating alleles to addiction phenotypes, e.g., for practicing the methods, are also a feature of the invention. In addition, the identification of these polymorphisms provides high-throughput systems and methods for identifying modulators of addiction phenotypes.

The following definitions are provided to more clearly identify aspects of the present invention. They should not be imputed to any other related or unrelated application or patent.

Definitions

It is to be understood that this invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a," "an," and "the," for example, optionally include plural referents unless the context clearly dictates otherwise. Thus, for example, reference to "a probe" optionally includes a plurality of probe molecules; similarly, depending on the context, use of the term "a nucleic acid" optionally includes, as a practical matter, many copies of that nucleic acid molecule. Letter designations for genes or proteins can refer to the gene form, the RNA form, and/or the protein form, depending on context. One of skill is fully able to relate the nucleic acid and amino acid forms of the relevant biological molecules by reference to the sequences herein, known sequences and the genetic code.

Unless otherwise indicated, nucleic acids are written left to right in a 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

A "phenotype" is a trait or collection of traits that is/are observable in an individual or population. The trait can be quantitative (a quantitative trait, or QTL) or qualitative. For example, susceptibility to addiction is a phenotype that can be monitored according to the methods, compositions and systems herein.

An "addiction phenotype" is a phenotype that displays a predisposition towards developing addiction or a phenotype that displays an increased susceptibility to addiction in an individual. A phenotype that displays a predisposition for addiction, can, for example, show a higher likelihood that addiction will occur in an individual with the phenotype than in members of the general population under a given set of environmental conditions. Addiction phenotypes include, for example, the existence of, medical history of, susceptibility to, or decreased resistance to addiction, such as nicotine addiction or addiction to other substances such as cocaine, heroine, alcohol, methamphetamines, etc. Addiction phenotypes also include responses to treatments (whether prophylactic or not) for any of the above phenotypes, including efficacious responses as well as side effects.

A "polymorphism" is a locus that is variable; that is, within a population, the nucleotide sequence at a polymorphism has more than one version or allele. The term "allele" refers to one of two or more different nucleotide sequences that occur or are encoded at a specific locus, or two or more different polypeptide sequences encoded by such a locus. For example, a first allele can occur on one chromosome, while a second allele occurs on a second homologous chromosome, e.g., as occurs for different chromosomes of a heterozygous individual, or between different homozygous or heterozygous individuals in a population. One example of a polymorphism is a "single nucleotide polymorphism" (SNP), which is a polymorphism at a single nucleotide position in a genome (the nucleotide at the specified position varies between individuals or populations).

An allele "positively" correlates with a trait when it is linked to it and when presence of the allele is an indictor that the trait or trait form will occur in an individual comprising the allele. An allele "negatively" correlates with a trait when it is linked to it and when presence of the allele is an indicator that a trait or trait form will not occur in an individual comprising the allele.

A marker polymorphism or allele is "correlated" with a specified phenotype (addiction susceptibility, etc.) when it can be statistically linked (positively or negatively) to the phenotype. This correlation is often inferred as being causal in nature, but it need not be—simple genetic linkage to (association with) a locus for a trait that underlies the phenotype is sufficient.

A "favorable allele" is an allele at a particular locus that positively correlates with a desirable phenotype, e.g., resistance to addiction, or that negatively correlates with an undesirable phenotype e.g., an allele that negatively correlates with predisposition to addiction. A favorable allele of a linked marker is a marker allele that segregates with the favorable allele. A favorable allelic form of a chromosome segment is a chromosome segment that includes a nucleotide sequence that positively correlates with the desired phenotype, or that negatively correlates with the unfavorable phenotype at one or more genetic loci physically located on the chromosome segment.

An "unfavorable allele" is an allele at a particular locus that negatively correlates with a desirable phenotype, or that correlates positively with an undesirable phenotype, e.g., positive correlation to addiction susceptibility. An unfavorable allele of a linked marker is a marker allele that segregates with the unfavorable allele. An unfavorable allelic form of a chromosome segment is a chromosome segment that includes a nucleotide sequence that negatively correlates with the desired phenotype, or positively correlates with the undesirable phenotype at one or more genetic loci physically located on the chromosome segment.

"Allele frequency" refers to the frequency (proportion or percentage) at which an allele is present at a locus within an individual, within a line, or within a population of lines. For example, for an allele "A," diploid individuals of genotype "AA," "Aa," or "aa" have allele frequencies of 1.0, 0.5, or 0.0, respectively. One can estimate the allele frequency within a line or population by averaging the allele frequencies of a sample of individuals from that line or population. Similarly, one can calculate the allele frequency within a population of lines by averaging the allele frequencies of lines that make up the population.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

A "locus" is a chromosomal position or region. For example, a polymorphic locus is a position or region where a polymorphic nucleic acid, trait determinant, gene or marker is located. In a further example, a "gene locus" is a specific chromosome location in the genome of a species where a specific gene can be found. Similarly, the term "quantitative trait locus" or "QTL" refers to a locus with at least two alleles that differentially affect the expression or alter the variation of a quantitative or continuous phenotypic trait in at least one genetic background, e.g., in at least one breeding population or progeny.

A "marker," "molecular marker" or "marker nucleic acid" refers to a nucleotide sequence or encoded product thereof (e.g., a protein) used as a point of reference when identifying a locus or a linked locus. A marker can be derived from genomic nucleotide sequence or from expressed nucleotide sequences (e.g., from an RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Nucleic acids are "complementary" when they specifically hybridize in solution, e.g., according to Watson-Crick base pairing rules. A "marker locus" is a locus that can be used to track the presence of a second linked locus, e.g., a linked or correlated locus that encodes or contributes to the population variation of a phenotypic trait. For example, a marker locus can be used to monitor segregation of alleles at a locus, such as a QTL, that are genetically or physically linked to the marker locus. Thus, a "marker allele," alternatively an "allele of a marker locus" is one of a plurality of polymorphic nucleotide sequences found at a marker locus in a population that is polymorphic for the marker locus. In one aspect, the present invention provides marker loci correlating with a phenotype of interest, e.g., addiction susceptibility/resistance. Each of the identified markers is expected to be in close physical and genetic proximity (resulting in physical and/or genetic linkage) to a genetic element, e.g., a QTL, that contributes to the relevant phenotype. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of allele specific hybridization (ASH), detection of single nucleotide extension, detection of amplified variable sequences of the genome, detection of self-sustained sequence replication, detection of simple sequence repeats (SSRs), detection of single nucleotide polymorphisms (SNPs), or detection of amplified fragment length polymorphisms (AFLPs).

A "genetic map" is a description of genetic linkage (or association) relationships among loci on one or more chromosomes (or linkage groups) within a given species, generally depicted in a diagrammatic or tabular form. "Mapping" is the process of defining the linkage relationships of loci through the use of genetic markers, populations segregating for the markers, and standard genetic principles of recombination frequency. A "map location" is an assigned location on a genetic map relative to linked genetic markers where a specified marker can be found within a given species. The term "chromosome segment" designates a contiguous linear span of genomic DNA that resides on a single chromosome. Similarly, a "haplotype" is a set of genetic loci found in the heritable material of an individual or population (the set can be a contiguous or non-contiguous). In the context of the present invention genetic elements such as one or more alleles herein and one or more linked marker alleles can be located within a chromosome segment and are also, accordingly, genetically linked, a specified genetic recombination distance of less than or equal to 20 centimorgan (cM) or less, e.g., 15 cM or less, often 10 cM or less, e.g., about 9, 8, 7, 6, 5, 4, 3, 2, 1, 0.75, 0.5, 0.25, or 0.1 CM or less. That is, two closely linked genetic elements within a single chromosome segment undergo recombination during meiosis with each other at a frequency of less than or equal to about 20%, e.g., about 19%, 18%, 17%, 16%, 15%, 14%, 13%, 12%, 11%, 10%, 9%, 8%, 7%, 6%, 5%, 4%, 3%, 2%, 1%, 0.75%, 0.5%, 0.25%, or 0.1% or less.

A "genetic recombination frequency" is the frequency of a recombination event between two genetic loci. Recombination frequency can be observed by following the segregation of markers and/or traits during meiosis. In the context of this invention, a marker locus is "associated with" another marker locus or some other locus (for example, an addiction susceptibility locus), when the relevant loci are part of the same linkage group due to association and are in linkage disequilibrium. This occurs when the marker locus and a linked locus are found together in progeny more frequently than if the loci segregate randomly. Similarly, a marker locus can also be associated with a trait, e.g., a marker locus can be "associated with" a given trait (addiction resistance or susceptibility) when the marker locus is in linkage disequilibrium with the trait. The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random frequency (in the case of co-segregating traits, the loci that underlie the traits are in sufficient proximity to each other). Linked loci co-segregate more than 50% of the time, e.g., from about 51% to about 100% of the time. Advantageously, the two loci are located in close proximity such that recombination between homologous chromosome pairs does not occur between the two loci during meiosis with high frequency, e.g., such that closely linked loci co-segregate at least about 80% of the time, more preferably at least about 85% of the time, still more preferably at least 90% of the time, e.g., 91%, 92%, 93%, 94%, 95%, 96%, 97%, 98%, 99%, 99.5%, 99.75%, or 99.90% or more of the time.

The phrase "closely linked," in the present application, means that recombination between two linked loci (e.g., a SNP such as one identified in Table 1 herein and a second linked allele) occurs with a frequency of equal to or less than about 20%. Put another way, the closely (or "tightly") linked loci co-segregate at least 80% of the time. Marker loci are especially useful in the present invention when they are closely linked to target loci (e.g., QTL for addiction, or, alternatively, simply other addiction marker loci). The more closely a marker is linked to a target locus, the better an indicator for the target locus that the marker is. Thus, in one embodiment, tightly linked loci such as a marker locus and a second locus display an inter-locus recombination frequency of about 20% or less, e.g., 15% or less, e.g., 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus such as a QTL) display a recombination frequency of about 1% or less, e.g., about 0.75% or less, more preferably about 0.5% or less, or yet more preferably about 0.25% or less, or still more preferably about 0.1% or less. Two loci that are localized to the same chromosome, and at such a distance that recombination between the two loci occurs at a frequency of less than about 20%, e.g., 15%, more preferably 10% (e.g., about 9%, 8%, 7%, 6%, 5%, 4%, 3%, 2%, 1%, 0.75%, 0.5%, 0.25%, 0.1% or less) are also said to be "proximal to" each other. When referring to the relationship between two linked genetic elements, such as a genetic element contributing to a trait and a proximal marker, "coupling" phase linkage indicates the state where the "favorable" allele at the trait locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for addiction susceptibility) is physically associated on the same chromosome strand as an "unfavorable" allele at the proximal marker locus, and the two "favorable" alleles are not inherited together (i.e., the two loci are "out of phase" with each other).

The term "amplifying" in the context of nucleic acid is any process whereby additional copies of a selected nucleic acid (or those transcribed form thereof) are produced. Typical amplification methods include various polymerase based replication methods, including the polymerase chain reaction (PCR) and whole genome amplification, ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like).

A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, enhancer regions, etc.) and/or non-translated sequences (e.g., introns), whereas spliced RNA/cDNA typically do not have non-transcribed sequences or introns. A "template genomic nucleic acid" is a genomic nucleic acid that serves as a template in an amplification reaction (e.g., a polymerase based amplification reaction such as PCR, whole genome amplification, a ligase mediated amplification reaction such as LCR, a transcription reaction, or the like).

An "exogenous nucleic acid" is a nucleic acid that is not native to a specified system (e.g., a germplasm, cell, individual, etc.), with respect to sequence, genomic position, or both. As used herein, the terms "exogenous" or "heterologous" as applied to polynucleotides or polypeptides typically refers to molecules that have been artificially supplied to a biological system (e.g., a cell, an individual, etc.) and are not native to that particular biological system. The terms can indicate that the relevant material originated from a source other than a naturally occurring source, or can refer to molecules having a non-natural configuration, genetic location or arrangement of parts.

The term "introduced" when referring to translocating a heterologous or exogenous nucleic acid into a cell refers to the incorporation of the nucleic acid into the cell using any methodology. The term encompasses such nucleic acid introduction methods as "transfection," "transformation" and "transduction."

As used herein, the term "vector" is used in reference to polynucleotides or other molecules that transfer nucleic acid segment(s) into a cell. The term "vehicle" is sometimes used interchangeably with "vector." A vector optionally comprises parts which mediate vector maintenance and enable its intended use (e.g., sequences necessary for replication, genes imparting drug or antibiotic resistance, a multiple cloning site, operably linked promoter/enhancer elements which enable the expression of a cloned gene, etc.). Vectors are often derived from plasmids, bacteriophages, or plant or animal viruses. A "cloning vector" or "shuttle vector" or "subcloning vector" contains operably linked parts that facilitate subcloning steps (e.g., a multiple cloning site containing multiple restriction endonuclease sites).

The term "expression vector" as used herein refers to a vector comprising operably linked polynucleotide sequences that facilitate expression of a coding sequence in a particular host organism (e.g., a bacterial expression vector or a mammalian cell expression vector). Polynucleotide sequences that facilitate expression in prokaryotes typically include, e.g., a promoter, an operator (optional), and a ribosome binding site, often along with other sequences. Eukaryotic cells can use promoters, enhancers, termination and polyadenylation signals and other sequences that are generally different from those used by prokaryotes. In one optional embodiment, a gene corresponding to a loci herein is cloned into an expression vector and expressed, with the gene product(s) to be used in the methods and systems herein for modulator identification.

A specified nucleic acid is "derived from" a given nucleic acid when it is constructed using the given nucleic acid's sequence, or when the specified nucleic acid is constructed using the given nucleic acid.

A "gene" is one or more sequence(s) of nucleotides in a genome that together encode one or more expressed molecule, e.g., an RNA, or polypeptide. The gene can include coding sequences that are transcribed into RNA which may then be translated into a polypeptide sequence, and can include associated structural or regulatory sequences that aid in replication or expression of the gene. Genes of interest in the present invention include those that include or are closely linked to the loci of Table 1.

A "genotype" is the genetic constitution of an individual (or group of individuals) at one or more genetic loci. Genotype is defined by the allele(s) of one or more known loci of the individual, typically, the compilation of alleles inherited from its parents. A "haplotype" is the genotype of an individual at a plurality of genetic loci on a single DNA strand. Typically, the genetic loci described by a haplotype are physically and genetically linked, i.e., on the same chromosome strand.

A "set" of markers or probes refers to a collection or group of markers or probes, or the data derived therefrom, used for a common purpose, e.g., identifying an individual with a specified phenotype (e.g., addiction resistance or susceptibility). Frequently, data corresponding to the markers or probes, or derived from their use, is stored in an electronic medium. While each of the members of a set possess utility with respect to the specified purpose, individual markers selected from the set as well as subsets including some, but not all of the markers, are also effective in achieving the specified purpose.

A "look up table" is a table that correlates one form of data to another, or one or more forms of data with a predicted outcome to which the data is relevant. For example, a look up table can include a correlation between allele data and a predicted trait that an individual comprising one or more given alleles is likely to display. These tables can be, and typically are, multidimensional, e.g., taking multiple alleles into account simultaneously, and, optionally, taking other factors into account as well, such as genetic background, e.g., in making a trait prediction.

A "computer readable medium" is an information storage media that can be accessed by a computer using an available or custom interface. Examples include memory (e.g., ROM or RAM, flash memory, etc.), optical storage media (e.g., CD-ROM), magnetic storage media (computer hard drives, floppy disks, etc.), punch cards, and many others that are commercially available. Information can be transmitted between a system of interest and the computer, or to or from the computer to or from the computer readable medium for storage or access of stored information. This transmission can be an electrical transmission, or can be made by other available methods, such as an IR link, a wireless connection, or the like.

"System instructions" are instruction sets that can be partially or fully executed by the system. Typically, the instruction sets are present as system software.

A "translation product" is a product (typically a polypeptide) produced as a result of the translation of a nucleic acid. A "transcription product" is a product (e.g., an RNA, optionally including mRNA, or, e.g., a catalytic or biologically active RNA) produced as a result of transcription of a nucleic acid (e.g., a DNA).

An "array" is an assemblage of elements. The assemblage can be spatially ordered (a "patterned array") or disordered (a "randomly patterned" array). The array can form or comprise one or more functional elements (e.g., a probe region on a microarray) or it can be non-functional.

As used herein, the term "SNP" or "single nucleotide polymorphism" refers to a genetic variation between individuals; e.g., a single nitrogenous base position in the DNA of organisms that is variable. As used herein, "SNPs" is the plural of SNP. Of course, when one refers to DNA herein, such reference may include derivatives of the DNA such as amplicons, RNA transcripts thereof, etc.

Overview

The invention includes new correlations between the polymorphisms of Table 1 (and genes that include or are proximal to the polymorphisms) and one or more addiction phenotypes (e.g., predisposition to addiction). Certain alleles in, and linked to, these genes or gene products are predictive of the likelihood that an individual possessing the relevant alleles will develop addiction or a addiction phenotype. Accordingly, detection of these alleles, by any available method, can be used for diagnostic purposes such as early detection of an addiction phenotype, diagnosis of susceptibility to an addiction phenotype, prognosis for patients that present with an addiction phenotype, and for determining an appropriate treatment or prophylactic for patients presenting with or at risk of developing a addiction phenotype.

The identification that the polymorphisms, genes or gene products of Table 1 are correlated with addiction phenotypes also provides a platform for screening potential modulators of addiction disorders. Modulators of the activity of any genes or encoded proteins corresponding to the polymorphisms of Table 1 are expected to have an effect on addiction phenotypes. Thus, methods of screening, systems for screening and the like, are features of the invention. Modulators identified by these screening approaches are also a feature of the invention.

Kits for the diagnosis and treatment of addiction phenotypes, e.g., comprising probes to identify relevant alleles, packaging materials, and instructions for correlating detection of relevant alleles to addiction phenotypes are also a feature of the invention. These kits can also include modulators of addiction phenotypes and/or instructions for treating patients using conventional methods.

Methods of Identifying Addiction Predisposition

As noted, the invention provides the discovery that certain genes or other loci of Table 1 are linked to addiction phenotypes. Thus, by detecting markers (e.g., the SNPs in Table 1 or loci closely linked thereto) that correlate, positively or negatively, with the relevant phenotypes, it can be determined whether an individual or population is likely to comprise these phenotypes. This provides enhanced early detection options to identify patients that are at risk of developing an addiction phenotype (e.g., nicotine addiction, etc.), making it possible, in some cases, to prevent actual development of the addiction phenotype, e.g., by taking early preventative action. Furthermore, knowledge of whether there is a molecular basis for the disorder can also assist in determining patient prognosis, e.g., by providing an indication of how likely it is that a patient can respond to conventional therapy for addiction. Disease treatment can also be targeted based on what type of molecular disorder the patient displays.

In addition, use of the various markers herein also adds certainty to existing diagnostic techniques for identifying whether a patient is suffering from or will develop a particular addiction phenotype. For specific methods of using markers for risk assessment, diagnostics, prognostics and theranostics, see, e.g., U.S. Ser. No. 10/956,224, filed Sep. 30, 2004, entitled "Methods for Genetic Analysis," and PCT application no. US2005/007375, filed Mar. 3, 2005, entitled "Methods for Genetic Analysis."

Determination of whether an individual or population is likely to comprise one or more addiction phenotypes may involve detecting the markers (e.g., the SNPs in Table 1 or loci closely linked thereto) that correlate, positively or negatively, with the relevant phenotypes in combination with other tests to provide additional risk stratification. (For methods of using genotypes in combination with phenotypes, see, e.g., U.S. Ser. No. 11/043,689, filed Jan. 24, 2005, entitled "Associations using Genotypes and Phenotypes").

Detection methods for detecting relevant alleles can include any available method, e.g., amplification technologies. For example, detection can include amplifying the polymorphism or a sequence associated therewith and detecting the resulting amplicon. This can include admixing an amplification primer or amplification primer pair with a nucleic acid template isolated from the organism or biological sample (e.g., comprising the SNP or other polymorphism), e.g., where the primer or primer pair is complementary or partially complementary to at least a portion of the gene or tightly linked polymorphism, or to a sequence proximal thereto. The primer is typically capable of initiating nucleic acid polymerization by a polymerase on the nucleic acid template. The primer or primer pair is extended, e.g., in a DNA polymerization reaction (PCR, RT-PCR, etc.) comprising a polymerase and the template nucleic acid to generate the amplicon. The amplicon is detected by any available detection process, e.g., sequencing, hybridizing the amplicon to an array (or affixing the amplicon to an array and hybridizing probes to it), digesting the amplicon with a restriction enzyme (e.g., RFLP), real-time PCR analysis, single nucleotide extension, allele-specific hybridization, or the like.

The correlation between a detected polymorphism and a trait can be performed by any method that can identify a relationship between an allele and a phenotype. Most typically, these methods involve referencing a look up table that comprises correlations between alleles of the polymorphism and the phenotype. The table can include data for multiple allele-phenotype relationships and can take account of additive or other higher order effects of multiple allele-phenotype relationships, e.g., through the use of statistical tools such as principle component analysis, heuristic algorithms, etc.

Within the context of these methods, the following discussion first focuses on how markers and alleles are linked and how this phenomenon can be used in the context of methods for identifying addiction phenotypes, and then focuses on marker detection methods. Additional sections below discuss data analysis.

Markers, Linkage And Alleles

In traditional linkage (or association) analysis, no direct knowledge of the physical relationship of genes on a chromosome is required. Mendel's first law is that factors of pairs of characters are segregated, meaning that alleles of a diploid trait separate into two gametes and then into different offspring. Classical linkage analysis can be thought of as a statistical description of the relative frequencies of cosegregation of different traits. Linkage analysis is the well characterized descriptive framework of how traits are grouped together based upon the frequency with which they segregate together. That is, if two non-allelic traits are inherited together with a greater than random frequency, they are said to be "linked." The frequency with which the traits are inherited together is the primary measure of how tightly the traits are linked, i.e., traits which are inherited together with a higher frequency are more closely linked than traits which are inherited together with lower (but still above random) frequency. Traits are linked because the genes which underlie the traits reside near one another on the same chromosome. The further apart on a chromosome the genes reside, the less likely they are to segregate together, because homologous chromosomes recombine during meiosis. Thus, the further apart on a chromosome the genes reside, the more likely it is that there will be a recombination event during meiosis that will result in two genes segregating separately into progeny.

A common measure of linkage (or association) is the frequency with which traits cosegregate. This can be expressed as a percentage of cosegregation (recombination frequency) or, also commonly, in centiMorgans (cM), which are actually a reciprocal unit of recombination frequency. The cM is named after the pioneering geneticist Thomas Hunt Morgan and is a unit of measure of genetic recombination frequency. One cM is equal to a 1% chance that a trait at one genetic locus will be separated from a trait at another locus due to recombination in a single generation (meaning the traits segregate together 99% of the time). Because chromosomal distance is approximately proportional to the frequency of recombination events between traits, there is an approximate physical distance that correlates with recombination frequency. For example, in humans, 1 cM correlates, on average, to about 1 million base pairs (1 Mbp).

Marker loci are themselves traits and can be assessed according to standard linkage analysis by tracking the marker loci during segregation. Thus, in the context of the present invention, one cM is equal to a 1% chance that a marker locus will be separated from another locus (which can be any other trait, e.g., another marker locus, or another trait locus that encodes a QTL for addiction), due to recombination in a single generation. The markers herein, e.g., those listed in Table 1, can correlate with addiction. This means that the markers comprise or are sufficiently proximal to a QTL for addiction that they can be used as a predictor for the trait itself. This is extremely useful in the context of disease diagnosis.

From the foregoing, it is clear that any marker that is linked to a trait locus of interest (e.g., in the present case, a QTL or identified linked marker locus for addiction, e.g., as in Table 1) can be used as a marker for that trait. Thus, in addition to the markers noted in Table 1, other markers closely linked to the markers itemized in Table 1 can also usefully predict the presence of the marker alleles indicated in Table 1 (and, thus, the relevant phenotypic trait). Such linked markers are particularly useful when they are sufficiently proximal to a given locus so that they display a low recombination frequency with the given locus. In the present invention, such closely linked markers are a feature of the invention. Closely linked loci display a recombination frequency with a given marker of about 20% or less (the given marker is within 20 cM of the given marker). Put another way, closely linked loci co-segregate at least 80% of the time. More preferably, the recombination frequency is 10% or less, e.g., 9%, 8%, 7%, 6%, 5%, 4%, 3%, 2%, 1%, 0.5%, 0.25%, or 0.1% or less. In one typical class of embodiments, closely linked loci are within 5 cM or less of each other.

As one of skill in the art will recognize, recombination frequencies (and, as a result, map positions) can vary depending on the map used (and the markers that are on the map). Additional markers that are closely linked to (e.g., within about 20 cM, or more preferably within about 10 cM of) the markers identified in Table 1 may readily be used for identification of QTL for addiction predisposition.

Marker loci are especially useful in the present invention when they are closely linked to target loci (e.g., QTL for addiction phenotypes, or, alternatively, simply other marker loci that are, themselves linked to such QTL) that they are being used as markers for. The more closely a marker is linked to a target locus that encodes or affects a phenotypic trait, the better an indicator for the target locus that the marker is (due to the reduced cross-over frequency between the target locus and the marker). Thus, in one embodiment, closely linked loci such as a marker locus and a second locus (e.g., a given marker locus of Table 1 and an additional second locus) display an inter-locus cross-over frequency of about 20% or less, e.g., 15% or less, preferably 10% or less, more preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus such as a QTL) display a recombination a frequency of about 1% or less, e.g., about 0.75% or less, more preferably about 0.5% or less, or yet more preferably about 0.25% or 0.1% or less. Thus, the loci are about 20 cM, 19 cM, 18 cM, 17 cM, 16 cM, 15 cM, 14 cM, 13 cM, 12 cM, 11 cM, 10 cM, 9 cM, 8 cM, 7 cM, 6 cM, 5 cM, 4 cM, 3 cM, 2 cM, 1 cM, 0.75 cM, 0.5 cM, 0.25 cM, 0 or 0.1 cM or less apart. Put another way, two loci that are localized to the same chromosome, and at such a distance that recombination between the two loci occurs at a frequency of less than 20% (e.g., about 19%, 18%, 17%, 16%, 15%, 14%, 13%, 12%, 11%, 10%, 9%, 8%, 7%, 6%, 5%, 4%, 3%, 2%, 1%, 0.75%, 0.5%, 0.25%, 0.1% or less) are said to be "proximal to" each other. In one aspect, linked markers are within 100 kb (which correlates in humans to about 0.1 cM, depending on local recombination rate), e.g., 50 kb, or even 20 kb or less of each other.

When referring to the relationship between two genetic elements, such as a genetic element contributing to addiction, and a proximal marker, "coupling" phase linkage indicates the state where the "favorable" allele at the locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for addiction) is physically linked with an "unfavorable" allele at the proximal marker locus, and the two "favorable" alleles are not inherited together (i.e., the two loci are "out of phase" with each other).

In addition to tracking SNP and other polymorphisms in the genome, and in corresponding expressed nucleic acids and polypeptides, expression level differences between individuals or populations for the gene products of Table 1 in either mRNA or protein form, can also correlate to addiction. Accordingly, markers of the invention can include any of, e.g.: genomic loci, transcribed nucleic acids, spliced nucleic acids, expressed proteins, levels of transcribed nucleic acids, levels of spliced nucleic acids, and levels of expressed proteins.

Marker Amplification Strategies

Amplification primers for amplifying markers (e.g., marker loci) and suitable probes to detect such markers or to genotype a sample with respect to multiple marker alleles, are a feature of the invention. In Table 1, specific loci for amplification are provided, along with amplicon sequences that one of skill can easily use (optionally in conjunction with known flanking sequences) in the design of such primers. For example, primer selection for long-range PCR is described in U.S. Pat. No. 6,898,531, issued May 24, 2005, entitled "Algorithms for Selection of Primer Pairs" and U.S. Ser. No. 10/236,480, filed Sep. 5, 2002; for short-range PCR, U.S. Ser. No. 10/341,832, filed Jan. 14, 2003 and provides guidance with respect to primer selection. Also, there are publicly available programs such as "Oligo" available for primer design. With such available primer selection and design software, the publicly available human genome sequence and the polymorphism locations as provided in Table 1, one of skill can design primers to amplify the SNPs of the present invention. Further, it will be appreciated that the precise probe to be used for detection of a nucleic acid comprising a SNP (e.g., an amplicon comprising the SNP) can vary, e.g., any probe that can identify the region of a marker amplicon to be detected can be used in conjunction with the present invention. Further, the configuration of the detection probes can, of course, vary. Thus, the invention is not limited to the sequences recited herein.

Indeed, it will be appreciated that amplification is not a requirement for marker detection—for example, one can directly detect unamplified genomic DNA simply by performing a Southern blot on a sample of genomic DNA. Procedures for performing Southern blotting, standard amplification (PCR, LCR, or the like) and many other nucleic acid detection methods are well established and are taught, e.g., in Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")) and *PCR Protocols A Guide to Methods and Applications* (Innis et al. eds) Academic Press Inc. San Diego, Calif. (1990) (Innis).

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

Typically, molecular markers are detected by any established method available in the art, including, without limitation, allele specific hybridization (ASH), detection of single nucleotide extension, array hybridization (optionally including ASH), or other methods for detecting single nucleotide polymorphisms (SNPs), amplified fragment length polymorphism (AFLP) detection, amplified variable sequence detection, randomly amplified polymorphic DNA (RAPD) detection, restriction fragment length polymorphism (RFLP) detection, self-sustained sequence replication detection, simple sequence repeat (SSR) detection, single-strand conformation polymorphisms (SSCP) detection, isozyme marker detection, northern analysis (where expression levels are used as markers), quantitative amplification of mRNA or cDNA, or the like. While the exemplary markers provided in the figures and tables herein are SNP markers, any of the aforementioned marker types can be employed in the context of the invention to identify linked loci that correlate with an addiction phenotype.

Example Techniques For Marker Detection

The invention provides molecular markers that comprise or are linked to QTL for addiction phenotypes. The markers find use in disease predisposition diagnosis, prognosis, treatment, etc. It is not intended that the invention be limited to any particular method for the detection of these markers.

Markers corresponding to genetic polymorphisms between members of a population can be detected by numerous methods well-established in the art (e.g., PCR-based sequence specific amplification, restriction fragment length polymorphisms (RFLPs), isozyme markers, northern analysis, allele specific hybridization (ASH), array based hybridization, amplified variable sequences of the genome, self-sustained sequence replication, simple sequence repeat (SSR), single nucleotide polymorphism (SNP), random amplified polymorphic DNA ("RAPD") or amplified fragment length polymorphisms (AFLP). In one additional embodiment, the presence or absence of a molecular marker is determined simply through nucleotide sequencing of the polymorphic marker region. Any of these methods are readily adapted to high throughput analysis.

Some techniques for detecting genetic markers utilize hybridization of a probe nucleic acid to nucleic acids corresponding to the genetic marker (e.g., amplified nucleic acids produced using genomic DNA as a template). Hybridization formats, including, but not limited to: solution phase, solid phase, mixed phase, or in situ hybridization assays are useful for allele detection. An extensive guide to the hybridization of nucleic acids is found in Tijssen (1993) *Laboratory Techniques in Biochemistry and Molecular Biology—Hybridization with Nucleic Acid Probes* Elsevier, N.Y., as well as in Sambrook, Berger and Ausubel.

For example, markers that comprise restriction fragment length polymorphisms (RFLP) are detected, e.g., by hybridizing a probe which is typically a sub-fragment (or a synthetic oligonucleotide corresponding to a sub-fragment) of the nucleic acid to be detected to restriction digested genomic DNA. The restriction enzyme is selected to provide restriction fragments of at least two alternative (or polymorphic) lengths in different individuals or populations. Determining one or more restriction enzyme that produces informative fragments for each allele of a marker is a simple procedure, well known in the art. After separation by length in an appropriate matrix (e.g., agarose or polyacrylamide) and transfer to a membrane (e.g., nitrocellulose, nylon, etc.), the labeled probe is hybridized under conditions which result in equilibrium binding of the probe to the target followed by removal of excess probe by washing.

Nucleic acid probes to the marker loci can be cloned and/or synthesized. Any suitable label can be used with a probe of the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and colorimetric labels. Other labels include ligands which bind to antibodies labeled with fluorophores, chemiluminescent agents, and enzymes. A probe can also constitute radiolabelled PCR primers that are used to generate a radiolabelled amplicon. Labeling strategies for labeling nucleic acids and corresponding detection strategies can be found, e.g., in Haugland (2003) *Handbook of Fluorescent Probes and Research Chemicals Ninth Edition* by Molecular Probes, Inc. (Eugene Oreg.). Additional details regarding marker detection strategies are found below.

Amplification-Based Detection Methods

PCR, RT-PCR and LCR are in particularly broad use as amplification and amplification-detection methods for amplifying nucleic acids of interest (e.g., those comprising marker loci), facilitating detection of the nucleic acids of interest. Details regarding the use of these and other amplification methods can be found in any of a variety of standard texts, including, e.g., Sambrook, Ausubel, and Berger. Many available biology texts also have extended discussions regarding PCR and related amplification methods. One of skill will appreciate that essentially any RNA can be converted into a double stranded DNA suitable for restriction digestion, PCR expansion and sequencing using reverse transcriptase and a polymerase ("Reverse Transcription-PCR, or "RT-PCR"). See also, Ausubel, Sambrook and Berger, above. These methods can also be used to quantitatively amplify mRNA or corresponding cDNA, providing an indication of expression levels of mRNA that correspond to, e.g., the genes or gene products of Table 1 in an individual. Differences in expression levels for these genes between individuals, families, lines and/or populations can be used as markers for addiction phenotypes.

Real Time Amplification/Detection Methods

In one aspect, real time PCR or LCR is performed on the amplification mixtures described herein, e.g., using molecular beacons or TaqMan™ probes. A molecular beacon (MB) is an oligonucleotide or PNA which, under appropriate hybridization conditions, self-hybridizes to form a stem and loop structure. The MB has a label and a quencher at the termini of the oligonucleotide or PNA; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, e.g., to a region of an amplicon during amplification), the MB label is unquenched. Details regarding standard methods of making and using MBs are well established in the literature and MBs are available from a number of commercial reagent sources. See also, e.g., Leone et al. (1995) "Molecular beacon probes combined with amplification by NASBA enable homogenous real-time detection of RNA." *Nucleic Acids Res.* 26:2150-2155; Tyagi and Kramer (1996) "Molecular beacons: probes that fluoresce upon hybridization" *Nature Biotechnology* 14:303-308; Blok and Kramer (1997) "Amplifiable hybridization probes containing a molecular switch" *Mol Cell Probes* 11:187-194; Hsuih et al. (1997) "Novel, ligation-dependent PCR assay for detection of hepatitis C in serum" *J Clin Microbiol* 34:501-507; Kostrikis et al. (1998) "Molecular beacons: spectral genotyping of human alleles" *Science* 279:1228-1229; Sokol et al. (1998) "Real time detection of DNA:RNA hybridization in living cells" *Proc. Natl. Acad. Sci. U.S.A.* 95:11538-11543; Tyagi et al. (1998) "Multicolor molecular beacons for allele discrimination" *Nature Biotechnology* 16:49-53; Bonnet et al. (1999) "Thermodynamic basis of the chemical specificity of structured DNA probes" *Proc. Natl. Acad. Sci. U.S.A.* 96:6171-6176; Fang et al. (1999) "Designing a novel molecular beacon for surface-immobilized DNA hybridization studies" J. Am. Chem. Soc. 121:2921-2922; Marras et al. (1999) "Multiplex detection of single-nucleotide variation using molecular beacons" *Genet. Anal. Biomol. Eng.* 14:151-156; and Vet et al. (1999) "Multiplex detection of four pathogenic retroviruses using molecular beacons" *Proc. Natl. Acad. Sci. U.S.A.* 96:6394-6399. Additional details regarding MB construction and use is found in the patent literature, e.g., U.S. Pat. No. 5,925,517 (Jul. 20, 1999) to Tyagi et al. entitled "Detectably labeled dual conformation oligonucleotide probes, assays and kits;" U.S. Pat. No. 6,150,097 to Tyagi et al. (Nov. 21, 2000) entitled "Nucleic acid detection probes having non-FRET fluorescence quenching and kits and assays including such probes" and U.S. Pat. No. 6,037,130 to Tyagi et al. (Mar. 14, 2000), entitled "Wavelength-shifting probes and primers and their use in assays and kits."

PCR detection and quantification using dual-labeled fluorogenic oligonucleotide probes, commonly referred to as TaqMan™ probes, can also be performed according to the present invention. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. Accordingly, TaqMan™ probes are oligonucleotides that have a label and a quencher, where the label is released during amplification by the exonuclease action of the polymerase used in amplification. This provides a real time measure of amplification during synthesis. A variety of TaqMan™ reagents are commercially available, e.g., from Applied Biosystems (Division Headquarters in Foster City, Calif.) as well as from a variety of specialty vendors such as Biosearch Technologies (e.g., black hole quencher probes). Further details regarding dual-label probe strategies can be found, e.g., in WO92/02638.

Other similar methods include e.g. fluorescence resonance energy transfer between two adjacently hybridized probes, e.g., using the "LightCycler®" format described in U.S. Pat. No. 6,174,670.

Array-Based Marker Detection

Array-based detection can be performed using commercially available arrays, e.g., from Affymetrix (Santa Clara, Calif.) or other manufacturers. Reviews regarding the operation of nucleic acid arrays include Sapolsky et al. (1999) "High-throughput polymorphism screening and genotyping with high-density oligonucleotide arrays." *Genetic Analysis: Biomolecular Engineering* 14:187-192; Lockhart (1998) "Mutant yeast on drugs" *Nature Medicine* 4:1235-1236; Fodor (1997) "Genes, Chips and the Human Genome." *FASEB Journal* 11:A879; Fodor (1997) "Massively Parallel Genomics." *Science* 277: 393-395; and Chee et al. (1996) "Accessing Genetic Information with High-Density DNA Arrays." *Science* 274:610-614. Array based detection is a preferred method for identification markers of the invention in samples, due to the inherently high-throughput nature of array based detection.

A variety of probe arrays have been described in the literature and can be used in the context of the present invention for detection of markers that can be correlated to the phenotypes noted herein. For example, DNA probe array chips or larger DNA probe array wafers (from which individual chips would otherwise be obtained by breaking up the wafer) are used in one embodiment of the invention. DNA probe array wafers generally comprise glass wafers on which high density arrays of DNA probes (short segments of DNA) have been placed. Each of these wafers can hold, for example, approximately 60 million DNA probes that are used to recognize longer sample DNA sequences (e.g., from individuals or populations, e.g., that comprise markers of interest). The recognition of sample DNA by the set of DNA probes on the glass wafer takes place through DNA hybridization. When a DNA sample hybridizes with an array of DNA probes, the sample binds to those probes that are complementary to the sample DNA sequence. By evaluating to which probes the sample DNA for an individual hybridizes more strongly, it is possible to determine whether a known sequence of nucleic acid is present or not in the sample, thereby determining whether a marker found in the nucleic acid is present. One can also use this approach to perform ASH, by controlling the hybridization conditions to permit single nucleotide discrimination, e.g., for SNP identification and for genotyping a sample for one or more SNPs.

The use of DNA probe arrays to obtain allele information typically involves the following general steps: design and manufacture of DNA probe arrays, preparation of the sample, hybridization of sample DNA to the array, detection of hybridization events and data analysis to determine sequence. Preferred wafers are manufactured using a process adapted from semiconductor manufacturing to achieve cost effectiveness and high quality, and are available, e.g., from Affymetrix, Inc of Santa Clara, Calif.

For example, probe arrays can be manufactured by light-directed chemical synthesis processes, which combine solid-phase chemical synthesis with photolithographic fabrication techniques as employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays can be synthesized simultaneously on a large glass wafer. This parallel process enhances reproducibility and helps achieve economies of scale.

Once fabricated, DNA probe arrays can be used to obtain data regarding presence and/or expression levels for markers of interest. The DNA samples may be tagged with biotin and/or a fluorescent reporter group by standard biochemical methods. The labeled samples are incubated with an array, and segments of the samples bind, or hybridize, with complementary sequences on the array. The array can be washed and/or stained to produce a hybridization pattern. The array is then scanned and the patterns of hybridization are detected by emission of light from the fluorescent reporter groups. Additional details regarding these procedures are found in the examples below. Because the identity and position of each probe on the array is known, the nature of the DNA sequences in the sample applied to the array can be determined. When these arrays are used for genotyping experiments, they can be referred to as genotyping arrays.

The nucleic acid sample to be analyzed is isolated, amplified and, typically, labeled with biotin and/or a fluorescent reporter group. The labeled nucleic acid sample is then incubated with the array using a fluidics station and hybridization oven. The array can be washed and or stained or counter-stained, as appropriate to the detection method. After hybridization, washing and staining, the array is inserted into a scanner, where patterns of hybridization are detected. The hybridization data are collected as light emitted from the fluorescent reporter groups already incorporated into the labeled nucleic acid, which is now bound to the probe array. Probes that most clearly match the labeled nucleic acid produce stronger signals than those that have mismatches. Since the sequence and position of each probe on the array are known, by complementarity, the identity of the nucleic acid sample applied to the probe array can be identified.

In one embodiment, two DNA samples may be differentially labeled and hybridized with a single set of the designed genotyping arrays. In this way two sets of data can be obtained from the same physical arrays. Labels that can be used include, but are not limited to, cychrome, fluorescein, or biotin (later stained with phycoerythrin-streptavidin after hybridization). Two-color labeling is described in U.S. Pat. No. 6,342,355, incorporated herein by reference in its entirety. Each array may be scanned such that the signal from both labels is detected simultaneously, or may be scanned twice to detect each signal separately.

Intensity data is collected by the scanner for all the markers for each of the individuals that are tested for presence of the marker. The measured intensities are a measure indicative of the amount of a particular marker present in the sample for a given individual (expression level and/or number of copies of the allele present in an individual, depending on whether genomic or expressed nucleic acids are analyzed). This can be used to determine whether the individual is homozygous or heterozygous for the marker of interest. The intensity data is processed to provide corresponding marker information for the various intensities.

Additional Details Regarding Amplified Variable Sequences, SSR, AFLP ASH, SNPs and Isozyme Markers Amplified variable sequences refer to amplified sequences of the genome which exhibit high nucleic acid residue variability between members of the same species. All organisms have variable genomic sequences and each organism (with the exception of a clone, e.g., a cloned cell) has a different set of variable sequences. Once identified, the presence of specific variable sequence can be used to predict phenotypic traits. Preferably, DNA from the genome serves as a template for amplification with primers that flank a variable sequence of DNA. The variable sequence is amplified and then sequenced.

Alternatively, self-sustained sequence replication can be used to identify genetic markers. Self-sustained sequence replication refers to a method of nucleic acid amplification using target nucleic acid sequences which are replicated exponentially, in vitro, under substantially isothermal conditions by using three enzymatic activities involved in retroviral replication: (1) reverse transcriptase, (2) Rnase H, and (3) a DNA-dependent RNA polymerase (Guatelli et al. (1990) *Proc Natl Acad Sci USA* 87:1874). By mimicking the retroviral strategy of RNA replication by means of cDNA intermediates, this reaction accumulates cDNA and RNA copies of the original target.

Amplified fragment length polymorphisms (AFLP) can also be used as genetic markers (Vos et al. (1995) *Nucl Acids Res* 23:4407). The phrase "amplified fragment length polymorphism" refers to selected restriction fragments which are amplified before or after cleavage by a restriction endonuclease. The amplification step allows easier detection of specific restriction fragments. AFLP allows the detection large numbers of polymorphic markers and has been used for genetic mapping (Becker et al. (1995) *Mol Gen Genet* 249:65; and Meksem et al. (1995) *Mol Gen Genet* 249:74).

Allele-specific hybridization (ASH) can be used to identify the genetic markers of the invention. ASH technology is based on the stable annealing of a short, single-stranded, oligonucleotide probe to a completely complementary single-strand target nucleic acid. Detection may be accomplished via an isotopic or non-isotopic label attached to the probe.

For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridization. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613, the ASH probe sequence may be bound to a membrane.

In one embodiment, ASH data are typically obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Single nucleotide polymorphisms (SNP) are markers that consist of a shared sequence differentiated on the basis of a single nucleotide. Typically, this distinction is detected by differential migration patterns of an amplicon comprising the SNP on e.g., an acrylamide gel. However, alternative modes of detection, such as hybridization, e.g., ASH, or RFLP analysis are also appropriate.

Isozyme markers can be employed as genetic markers, e.g., to track isozyme markers linked to the markers herein. Isozymes are multiple forms of enzymes that differ from one another in their amino acid, and therefore their nucleic acid sequences. Some isozymes are multimeric enzymes contain slightly different subunits. Other isozymes are either multimeric or monomeric but have been cleaved from the proenzyme at different sites in the amino acid sequence. Isozymes can be characterized and analyzed at the protein level, or alternatively, isozymes which differ at the nucleic acid level can be determined. In such cases any of the nucleic acid based methods described herein can be used to analyze isozyme markers.

Additional Details Regarding Nucleic Acid Amplification

As noted, nucleic acid amplification techniques such as PCR and LCR are well known in the art and can be applied to the present invention to amplify and/or detect nucleic acids of interest, such as nucleic acids comprising marker loci. Examples of techniques sufficient to direct persons of skill through such in vitro methods, including the polymerase chain reaction (PCR), the ligase chain reaction (LCR), Qβ-replicase amplification and other RNA polymerase mediated techniques (e.g., NASBA), are found in the references noted above, e.g., Innis, Sambrook, Ausubel, and Berger. Additional details are found in Mullis et al. (1987) U.S. Pat. No. 4,683,202; Arnheim & Levinson (Oct. 1, 1990) *C&EN* 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564. Improved methods of amplifying large nucleic acids by PCR, which is useful in the context of positional cloning, are further summarized in Cheng et al. (1994) *Nature* 369: 684, and the references therein, in which PCR amplicons of up to 40 kb are generated. Methods for long-range PCR are disclosed, for example, in U.S. Pat. No. 6,898,531, issued May 24, 2005, entitled "Algorithms for Selection of Primer Pairs"; U.S. patent application Ser. No. 10/236,480, filed Sep. 9, 2002, entitled "Methods for Amplification of Nucleic Acids"; and U.S. Pat. No. 6,740,510, issued May 25, 2004, entitled "Methods for Amplification of Nucleic Acids". U.S. Ser. No. 10/341,832 (filed Jan. 14, 2003) also provides details regarding primer picking methods for performing short range PCR.

Detection of Protein Expression Products

Proteins such as those encoded by the genes noted in Table 1 are encoded by nucleic acids, including those comprising markers that are correlated to the phenotypes of interest herein. For a description of the basic paradigm of molecular biology, including the expression (transcription and/or translation) of DNA into RNA into protein, see, Alberts et al. (2002) *Molecular Biology of the Cell, 4$^{th}$ Edition* Taylor and Francis, Inc., ISBN: 0815332181 ("Alberts"), and Lodish et al. (1999) *Molecular Cell Biology, 4$^{th}$ Edition* W H Freeman & Co, ISBN: 071673706X ("Lodish"). Accordingly, proteins corresponding to the genes in Table 1 can be detected as markers, e.g., by detecting different protein isotypes between individuals or populations, or by detecting a differential presence, absence or expression level of such a protein of interest (e.g., a gene product of the genes in Table 1).

A variety of protein detection methods are known and can be used to distinguish markers. In addition to the various references noted supra, a variety of protein manipulation and detection methods are well known in the art, including, e.g., those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods, $2^{nd}$ Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification Principles and Practice $3^{rd}$ Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein. Additional details regarding protein purification and detection methods can be found in Satinder Ahuja ed., *Handbook of Bioseparations*, Academic Press (2000).

"Proteomic" detection methods, which detect many proteins simultaneously have been described. These can include various multidimensional electrophoresis methods (e.g., 2-d gel electrophoresis), mass spectrometry based methods (e.g., SELDI, MALDI, electrospray, etc.), or surface plasmon resonance methods. For example, in MALDI, a sample is usually mixed with an appropriate matrix, placed on the surface of a probe and examined by laser desorption/ionization. The technique of MALDI is well known in the art. See, e.g., U.S. Pat. No. 5,045,694 (Beavis et al.), U.S. Pat. No. 5,202,561 (Gleissmann et al.), and U.S. Pat. No. 6,111,251 (Hillenkamp). Similarly, for SELDI, a first aliquot is contacted with a solid support-bound (e.g., substrate-bound) adsorbent. A substrate is typically a probe (e.g., a biochip) that can be positioned in an interrogatable relationship with a gas phase ion spectrometer. SELDI is also a well known technique, and has been applied to diagnostic proteomics. See, e.g. Issaq et al. (2003) "SELDI-TOF MS for Diagnostic Proteomics" *Analytical Chemistry* 75:149A-155A.

In general, the above methods can be used to detect different forms (alleles) of proteins and/or can be used to detect different expression levels of the proteins (which can be due to allelic differences) between individuals, families, lines, populations, etc. Differences in expression levels, when controlled for environmental factors, can be indicative of different alleles at a QTL for the gene of interest, even if the encoded differentially expressed proteins are themselves identical. This occurs, for example, where there are multiple allelic forms of a gene in non-coding regions, e.g., regions such as promoters or enhancers that control gene expression. Thus, detection of differential expression levels can be used as a method of detecting allelic differences.

In other aspect of the present invention, a gene comprising, in linkage disequilibrium with, or under the control of a nucleic acid associated with a addiction phenotype may exhibit differential allelic expression. "Differential allelic expression" as used herein refers to both qualitative and quantitative differences in the allelic expression of multiple alleles of a single gene present in a cell. As such, a gene displaying differential allelic expression may have one allele expressed at a different time or level as compared to a second allele in the same cell/tissue. For example, an allele associated with a addiction phenotype may be expressed at a higher or lower level than an allele that is not associated with the addiction phenotype, even though both are alleles of the same gene and are present in the same cell/tissue. Differential allelic expression and analysis methods are disclosed in detail in U.S. patent application Ser. No. 10/438,184, filed May 13, 2003 and U.S. patent application Ser. No. 10/845,316, filed May 12, 2004, both of which are entitled "Allele-specific expression patterns." Detection of a differential allelic expression pattern of one or more nucleic acids, or fragments, derivatives, polymorphisms, variants or complements thereof, associated with a addiction phenotype is a prognostic and diagnostic for susceptibility/resistance to a addiction phenotype; likewise, detection of a differential allelic expression pattern of one or more nucleic acids, or fragments, derivatives, polymorphisms, variants or complements thereof, associated with a addiction phenotype is a prognostic and diagnostic of a addiction phenotype and/or a addiction treatment outcome.

Additional Details Regarding Types of Markers Appropriate for Screening

The biological markers that are screened for correlation to the phenotypes herein can be any of those types of markers that can be detected by screening, e.g., genetic markers such as allelic variants of a genetic locus (e.g., as in SNPs), expression markers (e.g., presence or quantity of mRNAs and/or proteins), and/or the like.

The nucleic acid of interest to be amplified, transcribed, translated and/or detected in the methods of the invention can be essentially any nucleic acid, though nucleic acids derived from human sources are especially relevant to the detection of markers associated with disease diagnosis and clinical applications. The sequences for many nucleic acids and amino acids (from which nucleic acid sequences can be derived via reverse translation) are available, including for the genes/proteins of Table 1. Common sequence repositories for known nucleic acids include GenBank® EMBL, DDBJ and the NCBI. Other repositories can easily be identified by searching the internet. The nucleic acid to be amplified, transcribed, translated and/or detected can be an RNA (e.g., where amplification includes RT-PCR or LCR, the Van-Gelder Eberwine reaction or Ribo-SPIA) or DNA (e.g., amplified DNA, cDNA or genomic DNA), or even any analogue thereof (e.g., for detection of synthetic nucleic acids or analogues thereof, e.g., where the sample of interest includes or is used to derive or synthesize artificial nucleic acids). Any variation in a nucleic acid sequence or expression level between individuals or populations can be detected as a marker, e.g., a mutation, a polymorphism, a single nucleotide polymorphism (SNP), an allele, an isotype, expression of an RNA or protein, etc. One can detect variation in sequence, expression levels or gene copy numbers as markers that can be correlated to a addiction phenotype.

For example, the methods of the invention are useful in screening samples derived from patients for a marker nucleic acid of interest, e.g., from bodily fluids (blood, saliva, urine etc.), tissue, and/or waste from the patient. Thus, stool, sputum, saliva, blood, lymph, tears, sweat, urine, vaginal secretions, ejaculatory fluid or the like can easily be screened for nucleic acids by the methods of the invention, as can essentially any tissue of interest that contains the appropriate nucleic acids. These samples are typically taken, following informed consent, from a patient by standard medical laboratory methods.

Prior to amplification and/or detection of a nucleic acid comprising a marker, the nucleic acid is optionally purified from the samples by any available method, e.g., those taught in Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2001 ("Sambrook"); and/or *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")). A plethora of kits are also commercially available for the purification of nucleic acids from cells or other samples (see, e.g., EasyPrep™, FlexiPrep™, both from Pharmacia Biotech; StrataClean™, from Stratagene; and, QIAprep™ from Qiagen). Alternately, samples can simply be directly subjected to amplification or detection, e.g., following aliquotting and/or dilution.

Examples of markers can include polymorphisms, single nucleotide polymorphisms, presence of one or more nucleic acids in a sample, absence of one or more nucleic acids in a sample, presence of one or more genomic DNA sequences, absence or one or more genomic DNA sequences, presence of one or more mRNAs, absence of one or more mRNAs, expression levels of one or more mRNAs, presence of one or more proteins, expression levels of one or more proteins, and/or data derived from any of the preceding or combinations thereof. Essentially any number of markers can be detected, using available methods, e.g., using array technologies that provide high density, high throughput marker mapping. Thus, at least about 10, 100, 1,000, 10,000, or even 100,000 or more genetic markers can be tested, simultaneously or in a serial fashion (or combination thereof), for correlation to a relevant phenotype, in the first and/or second population. Combinations of markers can also be desirably tested, e.g., to identify genetic combinations or combinations of expression patterns in populations that are correlated to the phenotype.

As noted, the biological marker to be detected can be any detectable biological component. Commonly detected markers include genetic markers (e.g., DNA sequence markers present in genomic DNA or expression products thereof) and expression markers (which can reflect genetically coded factors, environmental factors, or both). Where the markers are expression markers, the methods can include determining a first expression profile for a first individual or population (e.g., of one or more expressed markers, e.g., a set of expressed markers) and comparing the first expression profile to a second expression profile for the second individual or population. In this example, correlating expression marker(s) to a particular phenotype can include correlating the first or second expression profile to the phenotype of interest.

Probe/Primer Synthesis Methods

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described by Beaucage and Caruthers (1981), *Tetrahedron Letts.*, 22(20): 1859-1862, e.g., using a commercially available automated synthesizer, e.g., as described in Needham-VanDevanter et al. (1984) *Nucleic Acids Res.*, 12:6159-6168. Oligonucleotides, including modified oligonucleotides can also be ordered from a variety of commercial sources known to persons of skill. There are many commercial providers of oligo synthesis services, and thus this is a broadly accessible technology. Any nucleic acid can be custom ordered from any of a variety of commercial sources, such as The Midland Certified Reagent Company (mcrc@oligos.com), The Great American Gene Company (www.genco.com), ExpressGen Inc. (www.expressgen.com), Operon Technologies Inc. (Alameda, Calif.) and many others. Similarly, PNAs can be custom ordered from any of a variety of sources, such as PeptidoGenic (pkim@ccnet.com), HTI Bio-products, inc. (htibio.com), BMA Biomedicals Ltd (U.K.), Bio-Synthesis, Inc., and many others.

In Silico Marker Detection

In some embodiments, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST, or even simple word processors. The entire human genome has been sequenced and, thus, sequence information can be used to identify marker regions, flanking nucleic acids, etc.

Amplification Primers for Marker Detection

In some preferred embodiments, the molecular markers of the invention are detected using a suitable PCR-based detection method, where the size or sequence of the PCR amplicon is indicative of the absence or presence of the marker (e.g., a particular marker allele). In these types of methods, PCR primers are hybridized to the conserved regions flanking the polymorphic marker region.

It will be appreciated that suitable primers to be used with the invention can be designed using any suitable method. It is not intended that the invention be limited to any particular primer or primer pair. For example, primers can be designed using any suitable software program, such as LASERGENE®, e.g., taking account of publicly available sequence information.

In some embodiments, the primers of the invention are radiolabelled, or labeled by any suitable means (e.g., using a non-radioactive fluorescent tag), to allow for rapid visualization of the different size amplicons following an amplification reaction without any additional labeling step or visualization step. In some embodiments, the primers are not labeled, and the amplicons are visualized following their size resolution, e.g., following agarose or acrylamide gel electrophoresis. In some embodiments, ethidium bromide staining of the PCR amplicons following size resolution allows visualization of the different size amplicons.

It is not intended that the primers of the invention be limited to generating an amplicon of any particular size. For example, the primers used to amplify the marker loci and alleles herein are not limited to amplifying the entire region of the relevant locus. The primers can generate an amplicon of any suitable length. In some embodiments, marker amplification produces an amplicon at least 20 nucleotides in length, or alternatively, at least 50 nucleotides in length, or alternatively, at least 100 nucleotides in length, or alternatively, at least 200 nucleotides in length.

Detection of Markers for Positional Cloning

In some embodiments, a nucleic acid probe is used to detect a nucleic acid that comprises a marker sequence. Such probes can be used, for example, in positional cloning to isolate nucleotide sequences linked to the marker nucleotide sequence. It is not intended that the nucleic acid probes of the invention be limited to any particular size. In some embodiments, nucleic acid probe is at least 20 nucleotides in length, or alternatively, at least 50 nucleotides in length, or alternatively, at least 100 nucleotides in length, or alternatively, at least 200 nucleotides in length.

A hybridized probe is detected using, autoradiography, fluorography or other similar detection techniques depending on the label to be detected. Examples of specific hybridization protocols are widely available in the art, see, e.g., Berger, Sambrook, and Ausubel, all herein.

Generation of Transgenic Cells

The present invention also provides cells which are transformed with nucleic acids corresponding to QTL identified according to the invention. For example, such nucleic acids include chromosome intervals (e.g., genomic fragments), ORFs and/or cDNAs that encode genes that correspond or are linked to QTL for addiction phenotypes. Additionally, the invention provides for the production of polypeptides that influence addiction phenotypes. This is useful, e.g., to prevent, predict or treat addictions, and for the generation of transgenic cells. These cells provide commercially useful cell lines having defined genes that influence the relevant phenotype, thereby providing a platform for screening potential modulators of phenotype, as well as basic research into the mechanism of action for each of the genes of interest. In addition, gene therapy can be used to introduce desirable genes into individuals or populations thereof. Such gene therapies may be used to provide a treatment for a disorder exhibited by an individual, or may be used as a preventative measure to prevent the development of such a disorder in an individual at risk. Knock-out animals, such as knock-out mice, can be produced for any of the genes noted herein, to further identify phenotypic effects of the genes. Similarly, recombinant mice or other animals can be used as models for human disease, e.g., by knocking out any natural gene herein and introduction (e.g., via homologous recombination) of the human (or other species) gene into the animal. The effects of modulators on the heterologous human genes and gene products can then be monitored in the resulting in vivo model animal system.

General texts which describe molecular biological techniques for the cloning and manipulation of nucleic acids and production of encoded polypeptides include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2001 ("Sambrook") and *Current Protocols in Molecular Biology*, F. M. Ausubel et al., eds., *Current Protocols*, a joint venture between Greene Publishing Associates, Inc. and John Wiley & Sons, Inc., (supplemented through 2004 or later) ("Ausubel")). These texts describe mutagenesis, the use of vectors, promoters and many other relevant topics related to, e.g., the generation of clones that comprise nucleic acids of interest, e.g., genes, marker loci, marker probes, QTL that segregate with marker loci, etc.

Host cells are genetically engineered (e.g., transduced, transfected, transformed, etc.) with the vectors of this invention (e.g., vectors, such as expression vectors which comprise an ORF derived from or related to a QTL) which can be, for example, a cloning vector, a shuttle vector or an expression vector. Such vectors are, for example, in the form of a plasmid, a phagemid, an *agrobacterium*, a virus, a naked polynucleotide (linear or circular), or a conjugated polynucleotide. Vectors can be introduced into bacteria, especially for the purpose of propagation and expansion. Additional details regarding nucleic acid introduction methods are found in Sambrook, Berger and Ausubel, infra. The method of introducing a nucleic acid of the present invention into a host cell is not critical to the instant invention, and it is not intended that the invention be limited to any particular method for introducing exogenous genetic material into a host cell. Thus, any suitable method, e.g., including but not limited to the methods provided herein, which provides for effective introduction of a nucleic acid into a cell or protoplast can be employed and finds use with the invention.

The engineered host cells can be cultured in conventional nutrient media modified as appropriate for such activities as, for example, activating promoters or selecting transformants. In addition to Sambrook, Berger and Ausubel, all infra, Atlas and Parks (eds) *The Handbook of Microbiological Media* (1993) CRC Press, Boca Raton, Fla. and available commercial literature such as the *Life Science Research Cell Culture Catalogue* (2004) from Sigma-Aldrich, Inc (St Louis, Mo.) ("Sigma-LSRCCC") provide additional details.

Making Knock-Out Animals and Transgenics

Transgenic animals are a useful tool for studying gene function and testing putative gene or gene product modulators. Human (or other selected species) genes herein can be introduced in place of endogenous genes of a laboratory animal, making it possible to study function of the human (or other, e.g., livestock) gene or gene product in the easily manipulated and studied laboratory animal.

It will be appreciated that there is not always a precise correspondence for responses to modulators between homologous gene in different animals, making the ability to study the human or other species of interest in a laboratory animal particularly useful. Although similar genetic manipulations can be performed in tissue culture, the interaction of genes and gene products in the context of an intact organism provides a more complete and physiologically relevant picture of such genes and gene products than can be achieved in simple cell-based screening assays. Accordingly, one feature of the invention is the creation of transgenic animals comprising heterologous genes of interest, e.g., the genes in Table 1.

In general, such a transgenic animal is simply an animal that has had appropriate genes (or partial genes, e.g., comprising coding sequences coupled to a promoter) introduced into one or more of its cells artificially. This is most commonly done in one of two ways. First, a DNA can be integrated randomly by injecting it into the pronucleus of a fertilized ovum. In this case, the DNA can integrate anywhere in the genome. In this approach, there is no need for homology between the injected DNA and the host genome. Second, targeted insertion can be accomplished by introducing the (heterologous) DNA into embryonic stem (ES) cells and selecting for cells in which the heterologous DNA has undergone homologous recombination with homologous sequences of the cellular genome. Typically, there are several kilobases of homology between the heterologous and genomic DNA, and positive selectable markers (e.g., antibiotic resistance genes) are included in the heterologous DNA to provide for selection of transformants. In addition, negative selectable markers (e.g., "toxic" genes such as bamase) can be used to select against cells that have incorporated DNA by non-homologous recombination (random insertion).

One common use of targeted insertion of DNA is to make knock-out mice. Typically, homologous recombination is used to insert a selectable gene driven by a constitutive promoter into an essential exon of the gene that one wishes to disrupt (e.g., the first coding exon). To accomplish this, the selectable marker is flanked by large stretches of DNA that match the genomic sequences surrounding the desired insertion point. Once this construct is electroporated into ES cells, the cells' own machinery performs the homologous recombination. To make it possible to select against ES cells that incorporate DNA by non-homologous recombination, it is common for targeting constructs to include a negatively selectable gene outside the region intended to undergo recombination (typically the gene is cloned adjacent to the shorter of the two regions of genomic homology). Because DNA lying outside the regions of genomic homology is lost during homologous recombination, cells undergoing homologous recombination cannot be selected against, whereas cells undergoing random integration of DNA often can. A commonly used gene for negative selection is the herpes virus thymidine kinase gene, which confers sensitivity to the drug gancyclovir.

Following positive selection and negative selection if desired, ES cell clones are screened for incorporation of the construct into the correct genomic locus. Typically, one designs a targeting construct so that a band normally seen on a Southern blot or following PCR amplification becomes replaced by a band of a predicted size when homologous recombination occurs. Since ES cells are diploid, only one allele is usually altered by the recombination event so, when appropriate targeting has occurred, one usually sees bands representing both wild type and targeted alleles.

The embryonic stem (ES) cells that are used for targeted insertion are derived from the inner cell masses of blastocysts (early mouse embryos). These cells are pluripotent, meaning they can develop into any type of tissue.

Once positive ES clones have been grown up and frozen, the production of transgenic animals can begin. Donor females are mated, blastocysts are harvested, and several ES cells are injected into each blastocyst. Blastocysts are then implanted into a uterine horn of each recipient. By choosing an appropriate donor strain, the detection of chimeric offspring (i.e., those in which some fraction of tissue is derived from the transgenic ES cells) can be as simple as observing hair and/or eye color. If the transgenic ES cells do not contribute to the germline (sperm or eggs), the transgene cannot be passed on to offspring.

Correlating Markers to Phenotypes

One aspect of the invention is a description of correlations between polymorphisms noted in Table 1 and addiction phenotypes. An understanding of these correlations can be used in the present invention to correlate information regarding a set of polymorphisms that an individual or sample is determined to possess and a phenotype that they are likely to display. Further, higher order correlations that account for combinations of alleles in one or more different genes can also be assessed for correlations to phenotype.

These correlations can be performed by any method that can identify a relationship between an allele and a phenotype, or a combination of alleles and a combination of phenotypes. For example, alleles in one or more of the genes or loci in Table 1 can be correlated with one or more addiction phenotypes. Most typically, these methods involve referencing a look up table that comprises correlations between alleles of the polymorphism and the phenotype. The table can include data for multiple allele-phenotype relationships and can take account of additive or other higher order effects of multiple allele-phenotype relationships, e.g., through the use of statistical tools such as principle component analysis, heuristic algorithms, etc.

Correlation of a marker to a phenotype optionally includes performing one or more statistical tests for correlation. Many statistical tests are known, and most are computer-implemented for ease of analysis. A variety of statistical methods of determining associations/correlations between phenotypic traits and biological markers are known and can be applied to the present invention. For an introduction to the topic, see, Hartl (1981) *A Primer of Population Genetics* Washington University, Saint Louis Sinauer Associates, Inc. Sunderland, M A ISBN: 0-087893-271-2. A variety of appropriate statistical models are described in Lynch and Walsh (1998) *Genetics and Analysis of Quantitative Traits*, Sinauer Associates, Inc. Sunderland M A ISBN 0-87893-481-2. These models can, for example, provide for correlations between genotypic and phenotypic values, characterize the influence of a locus on a phenotype, sort out the relationship between environment and genotype, determine dominance or penetrance of genes, determine maternal and other epigenetic effects, determine principle components in an analysis (via principle component analysis, or "PCA"), and the like. The references cited in these texts provides considerable further detail on statistical models for correlating markers and phenotype.

In addition to standard statistical methods for determining correlation, other methods that determine correlations by pattern recognition and training, such as the use of genetic algorithms, can be used to determine correlations between markers and phenotypes. This is particularly useful when identifying higher order correlations between multiple alleles and multiple phenotypes. To illustrate, neural network approaches can be coupled to genetic algorithm-type programming for heuristic development of a structure-function data space model that determines correlations between genetic information and phenotypic outcomes. For example, NNUGA (Neural Network Using Genetic Algorithms) is an available program (e.g., on the world wide web at the website for the Department of Computer Science at Ben Gurion University) which couples neural networks and genetic algorithms. An introduction to neural networks can be found, e.g., in Kevin Gurney, An Introduction to Neural Networks, UCL Press (1999) and on the world wide web at the website for the University of Sheffield. Additional useful neural network references include those noted above in regard to genetic algorithms and, e.g., Bishop, Neural Networks for Pattern Recognition, Oxford University Press (1995), and Ripley et al., Pattern Recognition and Neural Networks, Cambridge University Press (1995). Two tables showing exemplary data sets including certain statistical analyses are shown in Appendix 1. Specifically, Table 1 shows data for an association study designed to identify genetic loci associated with addiction, and Table 2 shows data from the association study correlating various addiction phenotypes with "case status," i.e., at least one incidence of addiction. These data are discussed further infra.

Additional references that are useful in understanding data analysis applications for using and establishing correlations, principle components of an analysis, neural network modeling and the like, include, e.g., Hinchliffe, *Modeling Molecular Structures*, John Wiley and Sons (1996), Gibas and Jambeck, *Bioinformatics Computer Skills*, O'Reilly (2001), Pevzner, *Computational Molecular Biology and Algorithmic Approach*, The MIT Press (2000), Durbin et al., *Biological Sequence Analysis: Probabilistic Models of Proteins and Nucleic Acids*, Cambridge University Press (1998), and Rashidi and Buehler, *Bioinformatic Basics: Applications in Biological Science and Medicine*, CRC Press LLC (2000).

In any case, essentially any statistical test can be applied in a computer implemented model, by standard programming methods, or using any of a variety of "off the shelf" software packages that perform such statistical analyses, including, for example, those noted above and those that are commercially available, e.g., from Partek Incorporated (St. Peters, Mo.; www.partek.com), e.g., that provide software for pattern recognition (e.g., which provide Partek Pro 2000 Pattern Recognition Software) which can be applied to genetic algorithms for multivariate data analysis, interactive visualization, variable selection, neural network & statistical modeling, etc. Relationships can be analyzed, e.g., by Principal Components Analysis (PCA) mapped scatterplots and biplots, Multi-Dimensional Scaling (MDS) Multi-Dimensional Scaling (MDS) mapped scatterplots, star plots, etc. Available software for performing correlation analysis includes SAS, R and MathLab.

The marker(s), whether polymorphisms or expression patterns, can be used for any of a variety of genetic analyses. For example, once markers have been identified, as in the present case, they can be used in a number of different assays for association studies. For example, probes can be designed for microarrays that interrogate these markers. Other exemplary assays include, e.g., the Taqman assays and molecular beacon assays described supra, as well as conventional PCR and/or sequencing techniques. Once the markers are identified (e.g., SNPs are genotyped) in a population, the information may be used for multiple association studies. Such use may be facilitated by storage of the marker and phenotype information in a database that may be accessed at a later date for additional analysis.

Additional details regarding association studies can be found in U.S. Pat. No. 6,969,589, issued Nov. 29, 2005, entitled "Methods for Genomic Analysis;" U.S. Pat. No. 6,897,025, issued May 24, 2005, entitled "Genetic Analysis Systems and Methods;" U.S. Ser. No. 10/286,417, filed Oct. 31, 2002, entitled "Methods for Genomic Analysis;" U.S. Ser. No. 10/768,788, filed Jan. 30, 2004, entitled "Apparatus and Methods for Analyzing and Characterizing Nucleic Acid Sequences;" U.S. Ser. No. 10/447,685, filed May 28, 2003, entitled "Liver Related Disease Compositions and Methods;" U.S. Ser. No. 10/970,761, filed Oct. 20, 2004, entitled "Analysis Methods and Apparatus for Individual Genotyping;" U.S. Ser. No. 10/956,224, filed Sep. 30, 2004, entitled "Methods for Genetic Analysis;" and U.S. Ser. No. 60/722,357, filed Sep. 30, 2005, entitled "Methods and Compositions for Screening and Treatment of Disorders of Blood Glucose Regulation."

In some embodiments, the marker data is used to perform association studies to show correlations between markers and phenotypes. This can be accomplished by determining marker characteristics in individuals with the phenotype of interest (i.e., individuals or populations displaying the phenotype of interest) and comparing the allele frequency or other characteristics (expression levels, etc.) of the markers in these individuals to the allele frequency or other characteristics in a control group of individuals. Such marker determinations can be conducted on a genome-wide basis, or can be focused on specific regions of the genome (e.g., haplotype blocks of interest). In one embodiment, markers that are linked to the genes or loci in Table 1 are assessed for correlation to one or more specific phenotypes.

In addition to the other embodiments of the methods of the present invention disclosed herein, the methods additionally allow for the "dissection" of a phenotype. That is, a particular phenotypes can result from two or more different genetic bases. For example, a susceptibility phenotype in one individual may be the result of a "defect" (or simply a particular allele—"defect" with respect to a susceptibility phenotype is context dependent, e.g., whether the phenotype is desirable or undesirable in the individual in a given environment) in a gene for in Table 1, while the same basic phenotype in a different individual may be the result of multiple "defects" in multiple genes in Table 1. Thus, scanning a plurality of markers (e.g., as in genome or haplotype block scanning) allows for the dissection of varying genetic bases for similar (or graduated) phenotypes. In one aspect, such a dissection allows more individualized treatment, since two different patients with the same clinical phenotypes may have different genetic profiles that underlie differential response to treatment. As such, diagnosis of an individual that comprises analysis of their genotype can be used to determine an appropriate treatment regimen. For example, a first set of individuals with a given phenotype (e.g., a history of addiction) and a particular genotype at one or more of the SNPs in Table 1 or SNPs closely linked thereto may have a highly efficacious response to a medical treatment (e.g., comprising administration of "drug X"), while a second set of individuals with the same phenotype but a different genotype at one or more of the SNPs in Table 1 instead experiences a negative side effect (e.g., insomnia, weight gain, depression, etc.) in response to the treatment. The markers of the present invention may be used in an association analysis to distinguish between individuals in the first set and individuals in the second set prior to treatment, thereby allowing those who are likely to benefit from the treatment to be treated and identifying those who are likely to experience the side effect for alternative treatments. These methods are discussed in more detail in, e.g., U.S. Ser. No. 10/956,224, filed Sep. 30, 2004, entitled "Methods for Genetic Analysis," and PCT application no. US2005/007375, filed Mar. 3, 2005, entitled "Methods for Genetic Analysis."

As described above, one method of conducting association studies is to compare the allele frequency (or expression level) of markers in individuals with a phenotype of interest ("case group") to the allele frequency in a control group of individuals. In one method, informative SNPs are used to make the SNP haplotype pattern comparison (an "informative SNP" is genetic SNP marker such as a SNP or subset (more than one) of SNPs in a genome or haplotype block that tends to distinguish one SNP or genome or haplotype pattern from other SNPs, genomes or haplotype patterns). The approach of using informative SNPs has an advantage over other whole genome scanning or genotyping methods known in the art, for instead of reading all 3 billion bases of each individual's genome—or even reading the 3-4 million common SNPs that may be found—only informative SNPs from a sample population need to be detected. Reading these particular, informative SNPs provides sufficient information to allow statistically accurate association data to be extracted from specific experimental populations, as described above.

Thus, in an embodiment of one method of determining genetic associations, the allele frequency of informative SNPs is determined for genomes of a control population that do not display the phenotype. The allele frequency of informative SNPs is also determined for genomes of a population that do display the phenotype. The informative SNP allele frequencies are compared. Allele frequency comparisons can be made, for example, by determining the allele frequency (number of instances of a particular allele in a population divided by the total number of alleles) at each informative SNP location in each population and comparing these allele frequencies. The informative SNPs displaying a difference between the allele frequency of occurrence in the control versus case populations/groups are selected for analysis. Once informative SNPs are selected, the SNP haplotype block(s) that contain the informative SNPs are identified, which in turn identifies a genomic region of interest that is correlated with the phenotype. The genomic regions can be analyzed by genetic or any biological methods known in the art e.g., for use as drug discovery targets or as diagnostic markers.

In another embodiment of the present invention, linkage disequilibrium (LD) mapping is used to group SNPs for use in association studies, rather than or in addition to the grouping of SNPs into haplotype blocks and patterns. SNPs in close proximity to one another are often strongly correlated, but this correlation structure, or LD, is complex and varies from one region of the genome to another, as well as between different populations. After identifying "LD bins" containing linked SNPs, it becomes possible to determine the sequence of further individuals by reading (e.g., genotyping) only one or a few SNPs from each LD bin as these SNPs are predictive of the genotypes of other SNPs in the LD bin. As for haplotype pattern-based methods, such predictive SNPs are termed "informative SNPs." Methods for determination and use of patterns of LD are provided, e.g., in Hinds, et al. (2005) "Whole-Genome Patterns of Common DNA Variation in Three Human Populations", *Science* 307:1072-1079.

Systems for Identifying Addiction Phenotypes

Systems for performing the above correlations are also a feature of the invention. Typically, the system will include system instructions that correlate the presence or absence of an allele (whether detected directly or, e.g., through expression levels) with a predicted phenotype. The system instructions can compare detected information as to allele sequence or expression level with a database that includes correlations between the alleles and the relevant phenotypes. As noted above, this database can be multidimensional, thereby including higher-order relationships between combinations of alleles and the relevant phenotypes. These relationships can be stored in any number of look-up tables, e.g., taking the form of spreadsheets (e.g., Excel™ spreadsheets) or databases such as an Access™, SQL™, Oracle™, Paradox™, or similar database. The system includes provisions for inputting sample-specific information regarding allele detection information, e.g., through an automated or user interface and for comparing that information to the look up tables.

Optionally, the system instructions can also include software that accepts diagnostic information associated with any detected allele information, e.g., a diagnosis that a subject with the relevant allele has a particular phenotype. This software can be heuristic in nature, using such inputted associations to improve the accuracy of the look up tables and/or interpretation of the look up tables by the system. A variety of such approaches, including neural networks, Markov modeling, and other statistical analysis are described above.

The invention provides data acquisition modules for detecting one or more detectable genetic marker(s) (e.g., one or more array comprising one or more biomolecular probes, detectors, fluid handlers, or the like). The biomolecular probes of such a data acquisition module can include any that are appropriate for detecting the biological marker, e.g., oligonucleotide probes, proteins, aptamers, antibodies, etc. These can include sample handlers (e.g., fluid handlers), robotics, microfluidic systems, nucleic acid or protein purification modules, arrays (e.g., nucleic acid arrays), detectors, thermocyclers or combinations thereof, e.g., for acquiring samples, diluting or aliquoting samples, purifying marker materials (e.g., nucleic acids or proteins), amplifying marker nucleic acids, detecting amplified marker nucleic acids, and the like.

For example, automated devices that can be incorporated into the systems herein have been used to assess a variety of biological phenomena, including, e.g., expression levels of genes in response to selected stimuli (Service (1998) "Microchips Arrays Put DNA on the Spot" *Science* 282:396-399), high throughput DNA genotyping (Zhang et al. (1999) "Automated and Integrated System for High-Throughput DNA Genotyping Directly from Blood" *Anal. Chem.* 71:1138-1145) and many others. Similarly, integrated systems for performing mixing experiments, DNA amplification, DNA sequencing and the like are also available. See, e.g., Service (1998) "Coming Soon: the Pocket DNA Sequencer" *Science* 282: 399-401. A variety of automated system components are available, e.g., from Caliper Technologies (Hopkinton, Mass.), which utilize various Zymate systems, which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). Similarly, commercially available microfluidic systems that can be used as system components in the present invention include those from Agilent technologies and Caliper Technologies. Furthermore, the patent and technical literature includes numerous examples of microfluidic systems, including those that can interface directly with microwell plates for automated fluid handling.

Any of a variety of liquid handling and/or array configurations can be used in the systems herein. One common format for use in the systems herein is a microtiter plate, in which the array or liquid handler includes a microtiter tray. Such trays are commercially available and can be ordered in a variety of well sizes and numbers of wells per tray, as well as with any of a variety of functionalized surfaces for binding of assay or array components. Common trays include the ubiquitous 96 well plate, with 384 and 1536 well plates also in common use. Samples can be processed in such trays, with all of the processing steps being performed in the trays. Samples can also be processed in microfluidic apparatus, or combinations of microtiter and microfluidic apparatus.

In addition to liquid phase arrays, components can be stored in or analyzed on solid phase arrays. These arrays fix materials in a spatially accessible pattern (e.g., a grid of rows and columns) onto a solid substrate such as a membrane (e.g., nylon or nitrocellulose), a polymer or ceramic surface, a glass or modified silica surface, a metal surface, or the like. Components can be accessed, e.g., by hybridization, by local rehydration (e.g., using a pipette or other fluid handling element) and fluidic transfer, or by scraping the array or cutting out sites of interest on the array.

The system can also include detection apparatus that is used to detect allele information, using any of the approaches noted herein. For example, a detector configured to detect real-time PCR products (e.g., a light detector, such as a fluorescence detector) or an array reader can be incorporated into the system. For example, the detector can be configured to detect a light emission from a hybridization or amplification reaction comprising an allele of interest, wherein the light emission is indicative of the presence or absence of the allele. Optionally, an operable linkage between the detector and a computer that comprises the system instructions noted above is provided, allowing for automatic input of detected allele-specific information to the computer, which can, e.g., store the database information and/or execute the system instructions to compare the detected allele specific information to the look up table.

Probes that are used to generate information detected by the detector can also be incorporated within the system, along with any other hardware or software for using the probes to detect the amplicon. These can include thermocycler elements (e.g., for performing PCR or LCR amplification of the allele to be detected by the probes), arrays upon which the probes are arrayed and/or hybridized, or the like. The fluid handling elements noted above for processing samples, can be used for moving sample materials (e.g., template nucleic acids and/or proteins to be detected) primers, probes, amplicons, or the like into contact with one another. For example, the system can include a set of marker probes or primers configured to detect at least one allele of one or more genes or linked loci associated with a phenotype, where the gene encodes a polymorphism in Table 1 (e.g., in a gene listed in Table 1). The detector module is configured to detect one or more signal outputs from the set of marker probes or primers, or an amplicon produced from the set of marker probes or primers, thereby identifying the presence or absence of the allele.

The sample to be analyzed is optionally part of the system, or can be considered separate from it. The sample optionally includes e.g., genomic DNA, amplified genomic DNA, cDNA, amplified cDNA, RNA, amplified RNA, proteins, etc., as noted herein. In one aspect, the sample is derived from a mammal such as a human patient.

Optionally, system components for interfacing with a user are provided. For example, the systems can include a user viewable display for viewing an output of computer-implemented system instructions, user input devices (e.g., keyboards or pointing devices such as a mouse) for inputting user commands and activating the system, etc. Typically, the system of interest includes a computer, wherein the various computer-implemented system instructions are embodied in computer software, e.g., stored on computer readable media.

Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or SequeI™, Oracle™, Paradox™) can be adapted to the present invention by inputting a character string corresponding to an allele herein, or an association between an allele and a phenotype. For example, the systems can include software having the appropriate character string information, e.g., used in conjunction with a user interface (e.g., a GUI in a standard operating system such as a Windows, Macintosh or LINUX system) to manipulate strings of characters. Specialized sequence alignment programs such as BLAST can also be incorporated into the systems of the invention for alignment of nucleic acids or proteins (or corresponding character strings) e.g., for identifying and relating multiple alleles.

As noted, systems can include a computer with an appropriate database and an allele sequence or correlation of the invention. Software for aligning sequences, as well as data sets entered into the software system comprising any of the sequences herein can be a feature of the invention. The computer can be, e.g., a PC (Intel x86 or Pentium chip-compatible DOS™, OS2™ WINDOWS™ WINDOWS NT™, WINDOWS95™, WINDOWS98™, WINDOWS2000, WINDOWSME, or LINUX based machine, a MACINTOSH™, Power PC, or a UNIX based (e.g., SUN™ work station or LINUX based machine) or other commercially common computer which is known to one of skill. Software for entering and aligning or otherwise manipulating sequences is available, e.g., BLASTP and BLASTN, or can easily be constructed by one of skill using a standard programming language such as Visualbasic, Fortran, Basic, Java, or the like.

Methods of Identifying Modulators

In addition to providing various diagnostic and prognostic markers for identifying addiction predisposition, etc., the invention also provides methods of identifying modulators of addiction phenotypes. In the methods, a potential modulator is contacted to a relevant protein corresponding to a loci in Table 1, or to a nucleic acid that encodes such a protein. An effect of the potential modulator on the gene or gene product is detected, thereby identifying whether the potential modulator modulates the underlying molecular basis for the phenotype.

In addition, the methods can include, e.g., administering one or more putative modulator to an individual that displays a relevant phenotype and determining whether the putative modulator modulates the phenotype in the individual, e.g., in the context of a clinical trial or treatment. This, in turn, determines whether the putative modulator is clinically useful.

The gene or gene product that is contacted by the modulator can include any allelic form noted herein. Allelic forms, whether genes, RNAs or proteins, that positively correlate to undesirable phenotypes are preferred targets for modulator screening.

Effects of interest that can be screened for include: (a) increased or decreased expression of a gene or gene product in Table 1 in the presence of the modulator; (b) a change in the timing or location of expression, or otherwise altered expression pattern of a gene in Table 1 and/or RNA or protein products thereof; (c) increased or decreased activity of the gene product of a gene in Table 1 in the presence of the modulator; (d) or a change in localization, or otherwise altered expression pattern of the RNA and/or proteins encoded by the loci of Table 1 in the presence of the modulator.

The precise format of the modulator screen will, of course, vary, depending on the effect(s) being detected and the equipment available. Northern analysis, quantitative RT-PCR and/or array-based detection formats can be used to distinguish expression levels or patterns of genes noted above. Protein expression levels can also be detected using available methods, such as western blotting, ELISA analysis, antibody hybridization, BIAcore, or the like. Any of these methods can be used to distinguish changes in expression levels of the loci of Table 1 or the RNA or proteins encoded therein that result from a potential modulator.

Accordingly, one may screen for potential modulators of the genes of Table 1 and/or the RNA and protein encoded therein for activity or expression. For example, potential modulators (small molecules, RNAs (e.g., RNAi), organic molecules, inorganic molecules, proteins, hormones, transcription factors, or the like) can be contacted to a cell comprising an allele of interest and an effect on activity or expression (or both) of a gene, RNA or protein corresponding to a loci in Table 1. For example, expression of any of the genes of Table 1 can be detected, e.g., via northern analysis or quantitative (optionally real time) RT-PCR, before and after application of potential expression modulators. Similarly, promoter regions of the various genes (e.g., generally sequences in the region of the start site of transcription, e.g., within 5 KB of the start site, e.g., 1 KB, or less e.g., within 500 BP or 250 BP or 100 BP of the start site) can be coupled to reporter constructs (CAT, beta-galactosidase, luciferase or any other available reporter) and can be similarly be tested for expression activity modulation by the potential modulator. In either case, the assays can be performed in a high-throughput fashion, e.g., using automated fluid handling and/or detection systems, in serial or parallel fashion. Similarly, activity modulators can be tested by contacting a potential modulator to an appropriate cell using any of the activity detection methods herein, regardless of whether the activity that is detected is the result of activity modulation, expression modulation or both. These assays can be in vitro, cell-based, or can be screens for modulator activity performed on laboratory animals such as knock-out transgenic mice comprising a gene of interest.

Biosensors for detecting modulator activity detection are also a feature of the invention. These include devices or systems that comprise a gene or gene product corresponding to a loci of Table 1 coupled to a readout that measures or displays one or more activity of the gene or product. Thus, any of the above described assay components can be configured as a biosensor by operably coupling the appropriate assay components to a readout. The readout can be optical (e.g., to detect cell markers or cell survival) electrical (e.g., coupled to a FET, a BIAcore, or any of a variety of others), spectrographic, or the like, and can optionally include a user-viewable display (e.g., a CRT or optical viewing station). The biosensor can be coupled to robotics or other automation, e.g., microfluidic systems, that direct contact of the putative modulators to the proteins of the invention, e.g., for automated high-throughput analysis of putative modulator activity. A large variety of automated systems that can be adapted to use with the biosensors of the invention are commercially available. For example, automated systems have been made to assess a variety of biological phenomena, including, e.g., expression levels of genes in response to selected stimuli (Service (1998) "Microchips Arrays Put DNA on the Spot" *Science* 282:396-399). Laboratory systems can also perform, e.g., repetitive fluid handling operations (e.g., pipetting) for transferring material to or from reagent storage systems that comprise arrays, such as microtiter trays or other chip trays, which are used as basic container elements for a variety of automated laboratory methods. Similarly, the systems manipulate, e.g., microtiter trays and control a variety of environmental conditions such as temperature, exposure to light or air, and the like. Many such automated systems are commercially available and are described herein, including those described above. These include various Zymate systems, ORCA® robots, microfluidic devices, etc. For example, the LabMicrofluidic device® high throughput screening system (HTS) by Caliper Technologies, Mountain View, Calif. can be adapted for use in the present invention to screen for modulator activity.

In general, methods and sensors for detecting protein expression level and activity are available, including those taught in the various references above, including R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods*, 2$^{nd}$ Edition Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification Principles and Practice* 3$^{rd}$ Edition Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and Satinder Ahuja ed., *Handbook of Bioseparations*, Academic Press (2000). "Proteomic" detection methods, which detect many proteins simultaneously have been described and are also noted above, including various multidimensional electrophoresis methods (e.g., 2-d gel electrophoresis), mass spectrometry based methods (e.g., SELDI, MALDI, electrospray, etc.), or surface plasmon resonance methods. These can also be used to track protein activity and/or expression level.

Similarly, nucleic acid expression levels (e.g., mRNA) can be detected using any available method, including northern analysis, quantitative RT-PCR, or the like. References sufficient to guide one of skill through these methods are readily available, including Ausubel, Sambrook and Berger.

Whole animal assays can also be used to assess the effects of modulators on cells or whole animals (e.g., transgenic knock-out mice), e.g., by monitoring an effect on a cell-based phenomenon, a change in displayed animal phenotype, or the like.

Potential modulator libraries to be screened for effects on expression and/or activity are available. These libraries can be random, or can be targeted. For example, a modulator library may be screened for effects on expression of, e.g., any of the genes of Table 1.

Targeted libraries include those designed using any form of a rational design technique that selects scaffolds or building blocks to generate combinatorial libraries. These techniques include a number of methods for the design and combinatorial synthesis of target-focused libraries, including morphing with bioisosteric transformations, analysis of target-specific privileged structures, and the like. In general, where information regarding structure of Table 1 genes or gene products is available, likely binding partners can be designed, e.g., using flexible docking approaches, or the like. Similarly, random libraries exist for a variety of basic chemical scaffolds. In either case, many thousands of scaffolds and building blocks for chemical libraries are available, including those with polypeptide, nucleic acid, carbohydrate, and other backbones. Commercially available libraries and library design services include those offered by Chemical Diversity (San Diego, Calif.), Affymetrix (Santa Clara, Calif.), Sigma (St. Louis Mo.), ChemBridge Research Laboratories (San Diego, Calif.), TimTec (Newark, Del.), Nuevolution A/S (Copenhagen, Denmark) and many others.

Kits for treatment of addiction phenotypes can include a modulator identified as noted above and instructions for administering the compound to a patient to prevent or treat addiction.

Cell Rescue and Therapeutic Administration

In one aspect, the invention includes rescue of a cell that is defective in function of one or more endogenous genes of Table 1 or gene products thereof (thus conferring the relevant phenotype of interest, e.g., addiction susceptibility or resistance, etc.). This can be accomplished simply by introducing a new copy of the gene (or a heterologous nucleic acid that expresses the relevant protein), i.e., a gene having an allele that is desired, into the cell. Other approaches, such as homologous recombination to repair the defective gene (e.g., via chimeraplasty) can also be performed. In any event, rescue of function can be measured, e.g., in any of the assays noted herein. Indeed, this method can be used as a general method of screening cells in vitro for expression or activity of any gene of Table 1 or gene products thereof. Accordingly, in vitro rescue of function is useful in this context for the myriad in vitro screening methods noted above. The cells that are rescued can include cells in culture, (including primary or secondary cell culture from patients, as well as cultures of well-established cells). Where the cells are isolated from a patient, this has additional diagnostic utility in establishing which gene or gene product is defective in a patient that presents with a relevant phenotype.

In another aspect, the cell rescue occurs in a patient, e.g., a human, e.g., to remedy a defect. Thus, one aspect of the invention is gene therapy to remedy defects. In these applications, the nucleic acids of the invention are optionally cloned into appropriate gene therapy vectors (and/or are simply delivered as naked or liposome-conjugated nucleic acids), which are then delivered, optionally in combination with appropriate carriers or delivery agents. Proteins can also be delivered directly, but delivery of the nucleic acid is typically preferred in applications where stable expression is desired. Similarly, modulators of any defect identified by the methods herein can be used therapeutically.

Compositions for administration, e.g., comprise a therapeutically effective amount of the modulator, gene therapy vector or other relevant nucleic acid, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering gene therapy vectors for topical use are well known in the art and can be applied to administration of the nucleic acids of the invention.

Therapeutic compositions comprising one or more modulator or gene therapy nucleic acid of the invention are optionally tested in one or more appropriate in vitro and/or in vivo animal model of disease, to confirm efficacy, tissue metabolism, and to estimate dosages, according to methods well known in the art. In particular, dosages can initially be determined by activity, stability or other suitable measures of the formulation.

Administration is by any of the routes normally used for introducing a molecule into ultimate contact with cells. Modulators and/or nucleic acids that encode a relevant sequence (e.g., any gene of Table 1) can be administered in any suitable manner, optionally with one or more pharmaceutically acceptable carriers. Suitable methods of administering such nucleic acids in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention. Compositions can be administered by a number of routes including, but not limited to: oral, intravenous, intraperitoneal, intramuscular, transdermal, subcutaneous, topical, sublingual, or rectal administration. Compositions can be administered via liposomes (e.g., topically), or via topical delivery of naked DNA or viral vectors. Such administration routes and appropriate formulations are generally known to those of skill in the art.

The compositions, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials.

The dose administered to a patient, in the context of the present invention, is sufficient to effect a beneficial prophylactic and/or therapeutic response in the patient over time. The dose is determined by the efficacy of the particular vector, or other formulation, and the activity, stability or serum half-life of the polypeptide or other gene product which is expressed, and the condition of the patient, as well as the body weight or surface area of the patient to be treated. The size of the dose is also determined by the existence, nature, and extent of any adverse side-effects that accompany the administration of a particular vector, formulation, or the like in a particular patient. In determining the effective amount of the vector or formulation to be administered in the treatment of disease (e.g., addiction), the physician evaluates local expression, or circulating plasma levels, formulation toxicities, progression of the relevant disease, and/or where relevant, the production of antibodies to proteins encoded by the polynucleotides. The dose administered, e.g., to a 70 kilogram patient are typically in the range equivalent to dosages of currently-used therapeutic proteins, etc., adjusted for the altered activity or serum half-life of the relevant composition. The vectors of this invention can supplement treatment conditions by any known conventional therapy.

For administration, formulations of the present invention are administered at a rate determined by the LD-50 of the relevant formulation, and/or observation of any side-effects of the vectors of the invention at various concentrations, e.g., as applied to the mass or topical delivery area and overall health of the patient. Administration can be accomplished via single or divided doses.

If a patient undergoing treatment develops fevers, chills, or muscle aches, he/she receives the appropriate dose of aspirin, ibuprofen, acetaminophen or other pain/fever controlling drug. Patients who experience reactions to the compositions, such as fever, muscle aches, and chills are premedicated 30 minutes prior to the future infusions with either aspirin, acetaminophen, or, e.g., diphenhydramine. Meperidine is used for more severe chills and muscle aches that do not quickly respond to antipyretics and antihistamines. Treatment is slowed or discontinued depending upon the severity of the reaction.

EXAMPLES

The following examples are offered to illustrate, but not to limit the claimed invention. One of skill will recognize a variety of non-critical parameters that can be altered within the scope of the invention.

Example 1

Strategies for Identification of Addiction Markers

Introduction: Identifying Common Genetic Variants

The aim of the study was to identify genetic markers and determinants of addiction. There are important applications to public health in the identification of addiction marker alleles. Where genetic variation is due to many loci, risks to individuals vary widely, depending upon the number of high-risk alleles inherited at susceptibility loci. Common genetic variants that confer modest degrees of risk have individually important effects at the population level. Genes that are identified as being correlated to addiction risk can be used for estimation of associated and individual risks. (See, e.g., U.S. Ser. No. 10/956,224, filed Sep. 30, 2004, entitled "Methods for Genetic Analysis," and PCT application no. US2005/007375, filed Mar. 3, 2005, entitled "Methods for Genetic Analysis.") The practical consequences of this risk estimation are substantial. In addition, if the variant indicates a feasible mechanism for intervention, this also provides novel possibilities for targeted prevention.

In addition to these practical outcomes, the identification of addiction susceptibility loci and genes helps to clarify mechanisms of the development of addiction and other related diseases and disorders (e.g., nicotine addiction, etc.) Extending beyond known candidates to a whole genome search has the great advantage that totally novel mechanisms emerge. These mechanisms also provide new therapeutic targets.

Finally, knowledge of susceptibility genes allows clarification of the effects of lifestyle risk factors by studying the effects of genes and these risk factors in combination, using for example the cohort described herein.

Study Design

An efficient design to identify common low risk alleles is a case/control study. Variants that were associated with addiction were identified by their occurrence at a significantly higher frequency in cases than in controls matched for genetic background. In this study, the variants were single nucleotide polymorphisms (SNPs).

The case-control association study approach has been used previously on a "candidate gene" basis. However, there are serious limitations to a candidate gene approach. It is slow and relatively expensive, being dependent on developing assays on a SNP by SNP basis for each gene to be tested; it is incomplete in its coverage even of the candidate genes, in particular ignoring, in most cases, potential regulatory variation; and it is restricted by current knowledge of the biology of the disease. The genome-wide search used in this study, by contrast, had the potential to identify active common variants without any prior knowledge of function or location.

In this study, pooled genotyping for ~2.4 million single nucleotide polymorphisms (SNPs) was performed using 482 "cases" (chronic nicotine users whose Fagerström Test of Nicotine Dependence (FTND) score was at least a 3) and 466 "controls" (chronic nicotine users whose FTND score was 0). Based in part on the results of the pooled genotyping, 44,454 were chosen for individual genotyping in the same set of cases and controls, as well as an additional 568 cases and 413 controls. The positive associations found after individual genotyping are shown in Table 1.

Laboratory Set Up for Sample Collection, Processing and SNP Genotyping.

In brief, the laboratory set up was as follows. All patients read and signed informed consent forms before their samples were used in this study. All samples were barcoded and patient information was entered into an electronic database at the collection site. The samples were uniquely tied to the patients from whom they were collected, and each sample container was uniquely identifiable. The barcoded samples were provided to the genotyping laboratory, and within the laboratory, samples were tracked with a Laboratory Information Management System (Thermo, Altringham UK). Amplification of the whole genome was performed on the sample DNAs, and these samples were subsequently subjected to PCR and pooled and/or individual genotyping as described above. Genotypes were exported to a database and linked to the phenotypic data on each subject. Control genotypes were tested for departure from Hardy-Weinberg equilibrium as a quality control step.

Research Design

The study was organized in phases:

Phase 1. The full set of ~2.4 million SNPs were analyzed in 482 addiction cases and 466 controls using a pooled genotyping methodology.

Phase 2. A set of 44,454 SNPs (e.g., those that showed a significant difference in frequency between the addiction cases and controls in the pooled genotyping) were evaluated in the original cases and controls, as well as in a further 568 addiction cases and 413 controls. Approximately 4000 SNPs were identified as associated with the nicotine addiction phenotype, and these SNPs are listed in Table 1.

Rationale for the Research Design

The phased design was chosen to minimize the amount of genotyping required, while retaining a high power to detect SNPs with a modest effect on risk. Calculations have shown that such a phased design is very efficient compared with genotyping all samples for all SNPs (Satagopan J M et al. (2002) "Two-staged designs for gene-disease association studies." *Biometrics* 58:163-170).

Scan Quality Control

The samples were each genotyped individually on a genome-wide platform of ~2.4 million SNPs tiled on high-density oligonucleotide microarrays. The scans for each sample were subjected to standard quality criteria, which include a high call rate, high consistency in calls across microarrays for overlapping SNPs, and other measures. Good quality data was obtained in this manner.

Individual Genotype Reporting

The majority of the SNPs included on the custom individual genotyping (IG) chip were selected from the pooled genotyping, while other SNPs were added to cover candidate gene regions and for other specific reasons. An additional 311 stratification SNPs and a number of QC SNPs were also tiled on the chip to help estimate population structure and genomic control corrections. Table 2 outlines the counts of SNPs in the different categories in a descending order of exclusion (i.e., if a SNP is already covered by any of the categories above the given category it is not counted in the given category—to prevent double counting of SNPs). Many selection criteria were applied to this set of SNPs to arrive at a set of 35,673 reliable SNPs that were reported together with their genotypes.

TABLE 2

| SNP origin | number of SNPs |
|---|---|
| candidate gene | 4901 |
| from pooled genotyping | 39213 |
| custom chosen | 39 |
| stratification SNPs | 301 |
| QC SNPs | 1888 |

Table 3 shows the split of number of samples between the pooled genotyping (PG) samples (1/0 or Y/N) and replication samples (the additional samples that were individually genotyped, but not subjected to pooled genotyping), case control status and gender:

TABLE 3

| is PG sample | case control status | gender | number of samples |
|---|---|---|---|
| 0 | C | F | 313 |
| 0 | C | M | 255 |
| 0 | T | F | 283 |
| 0 | T | M | 130 |
| 1 | C | F | 272 |
| 1 | C | M | 210 |
| 1 | T | F | 328 |
| 1 | T | M | 138 |

Trend Score Analysis

Trend scores were computed separately for the PG samples (round 1) and replication samples as well as for the combined set. The following outlines the computation of the Armitage's trend score $\chi^2$:

$$\chi^2 = \frac{(\Delta p)^2}{\text{Var}(\Delta p)}$$

$$\text{Var}(\Delta p) = (p_1 + P_{11} - 2p_1^2)\left(\frac{1}{2n_T} + \frac{1}{2n_C}\right)$$

Where $\Delta p$ is the observed allele frequency difference between cases and controls, $p_1$ is the overall population prevalence of the arbitrary designated "1" allele, $P_{11}$ is the fraction of samples that have two copies of allele "1", $n_C$ and $n_T$ are the number of case and control samples, respectively.

GC Correction

The trend scores were corrected using GC correction. The GC correction for both the round 1 samples and the full set of samples was computed over the set of QC and stratification SNPs that were selected independent of the pooled study and the candidate gene regions. These SNPs therefore provide unbiased estimate of the GC correction in the round 1 and in the full set of samples. For replication samples, all the SNPs were used for the GC estimate and the large number of SNPs permitted use of a regression to better distribute the GC correction between SNPs with varying reliability of the allele frequency difference estimate. The reliability of the allele frequency differences of SNPs was estimated by the absolute values of deltas between allele frequency difference between cases and controls computed from filtered and unfiltered genotypes. The larger the delta between the allele frequency difference of unfiltered versus filtered genotypes, the larger is the possible distortion of the allele frequency difference in the filtered genotypes caused by the genotype filtering. The regression of the trend score values against the deltas of the allele frequency differences was done using log link and Gamma distribution. This procedure allows better distribution of the power hit from the GC correction between SNPs based on their reliability of the delta allele frequency between cases and controls. The regression therefore yielded a GC correction specific to each SNP computed from the SNP's delta.

For sex-linked SNPs the GC correction variance inflation factor $\lambda$ was corrected for the smaller number of chromosomes due to the presence of males among the samples:

$$\lambda_{corr,X} = 1 + \frac{\lambda - 1}{R} \cdot R_X$$

$$\lambda_{corr,Y} = 1 + \frac{\lambda - 1}{R} \cdot R_Y$$

Where:

$$R = \frac{1}{\frac{1}{2(n_{C,F} + n_{C,M})} + \frac{1}{2(n_{T,F} + n_{T,M})}}$$

$$R_X = \frac{1}{\frac{1}{2n_{C,F} + n_{C,M}} + \frac{1}{2n_{T,F} + n_{T,M}}}$$

$$R_Y = \frac{1}{\frac{1}{n_{C,M}} + \frac{1}{n_{T,M}}}$$

and where $n_{C,F}$, $n_{C,M}$, $n_{T,F}$, $n_{T,M}$ are number of female cases, number of male cases, number of female controls and number of male controls, respectively. The $\lambda_{corr,X}$ and $\lambda_{corr,Y}$ are the corrected $\lambda$ for chromosome X and chromosome Y sex-linked SNPs, respectively.

Results:

Applied Tests

The round 1 samples yielded GC correction variance inflation factor of 0.881 and therefore no GC correction was applied to the trend scores and their p-values.

The replication samples yielded GC correction variance inflation factor of 1.070, however the individual GC correction variance inflation factors were computed using the regression procedure outlined above. The regression of the trend score values against the deltas of the allele frequency differences using log link and Gamma distribution did yield positive slope, indicating as expected that the larger the delta between the allele frequency difference computed from unfiltered and filtered genotypes, the more inflated the trend scores tend to be. These GC correction variance inflation factors were further corrected for the smaller number of chromosomes for sex-linked SNPs due to the presence on males among the samples as outlined above.

The full sample set yielded GC correction variance inflation factor 1.026 and due to the limited number of SNPs from which the variance inflation factor was estimated the more robust correction procedure that effectively divides each trend score by the variance inflation factor was used.

Another set of p-values was computed using linear and logistic regressions. Different models were evaluated for significance of association with the phenotype. The various complexity models evaluated significance of different covariate inclusions:

TABLE 4

| model | ANOVA evaluated covariate | ANOVA p-value |
|---|---|---|
| gender | gender | 4.26E−10 |
| gender + age | age | 1.48E−03 |
| gender + factor(site) | factor(site) | 4.80E−23 |
| gender + factor(site) + age | age | 7.90E−01 |
| gender + factor(site) + age + gender:factor(site) | gender:factor(site) | 6.30E−01 |

The ANOVA p-values indicate that only gender and site explain significant phenotype variance. Site 3 and 4 turned out to be responsible for most of the association. The significance of the gender and site is expected from the non-homogeneous distribution of cases and controls between different genders and sites. The inclusion of gender and site to the model lowers the possible association of genotype with the phenotype only by the extent of the correlation between the genotype and any of the covariates. There might be some random correlations that will decrease the power to detect genotype associations, but they should not have a great effect. The model also contained an interaction between gender and genotype, because it is conceivable that the genotype effect might have different slopes for different genders (i.e., the strength of association might be different between the two genders). Therefore the following model was fitted using both logistic regression (using the binary case control assignment) and the quantitative FTND trait was fitted using linear regression:

Phenotype~gender+factor(site)+genotype+gender:genotype.

The Q-Q plots in FIGS. 1-6 show that the regressions do yield distributions of statistics corresponding well to the expected null distribution. The statistics for both the round 1 set of samples and the full set of samples were taken only from the stratification and QC SNPs that are expected to be null distributed.

Analysis of Candidate Gene Region

The candidate gene region consisting of 4901 CG SNPs and 39 custom added SNPs was analyzed separately, as agreed from our discussions. The region yielded 4222 reliable SNPs. No SNP in the candidate gene region is strictly significant at the level of 0.05 corrected by Bonferroni for the 4222 tested SNPs (which corresponds to uncorrected p-value of 1.2e-5). However, 8 SNPs show p-values from the linear regression in the e-5 range and 2 SNPs have p-values from the logistic regression in the e-5 range. Bonferroni correction is also likely to be too conservative as there are regions of LD that will lower the effective number of independent tests.

Figure 7:
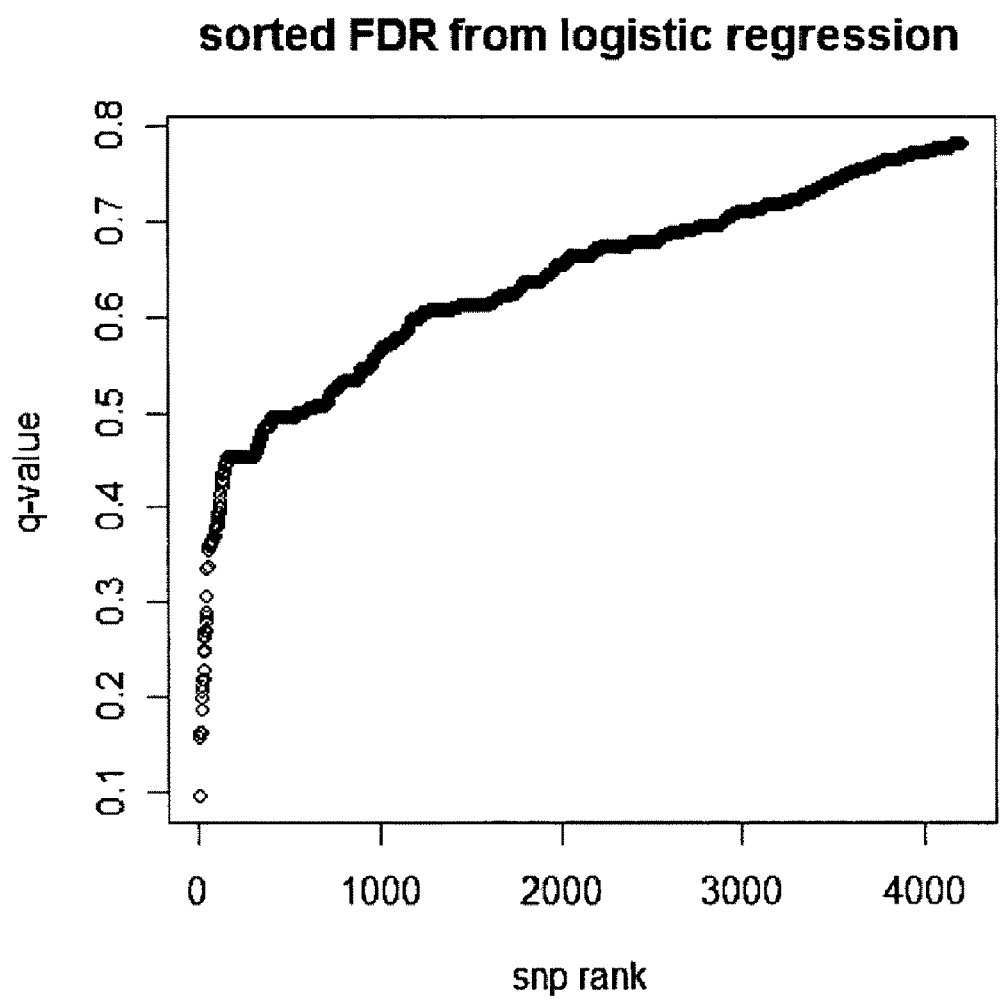
FIG. 7 shows a plot of the FDR q-values in an ordered set of SNPS from Example 1.
Figure 8:
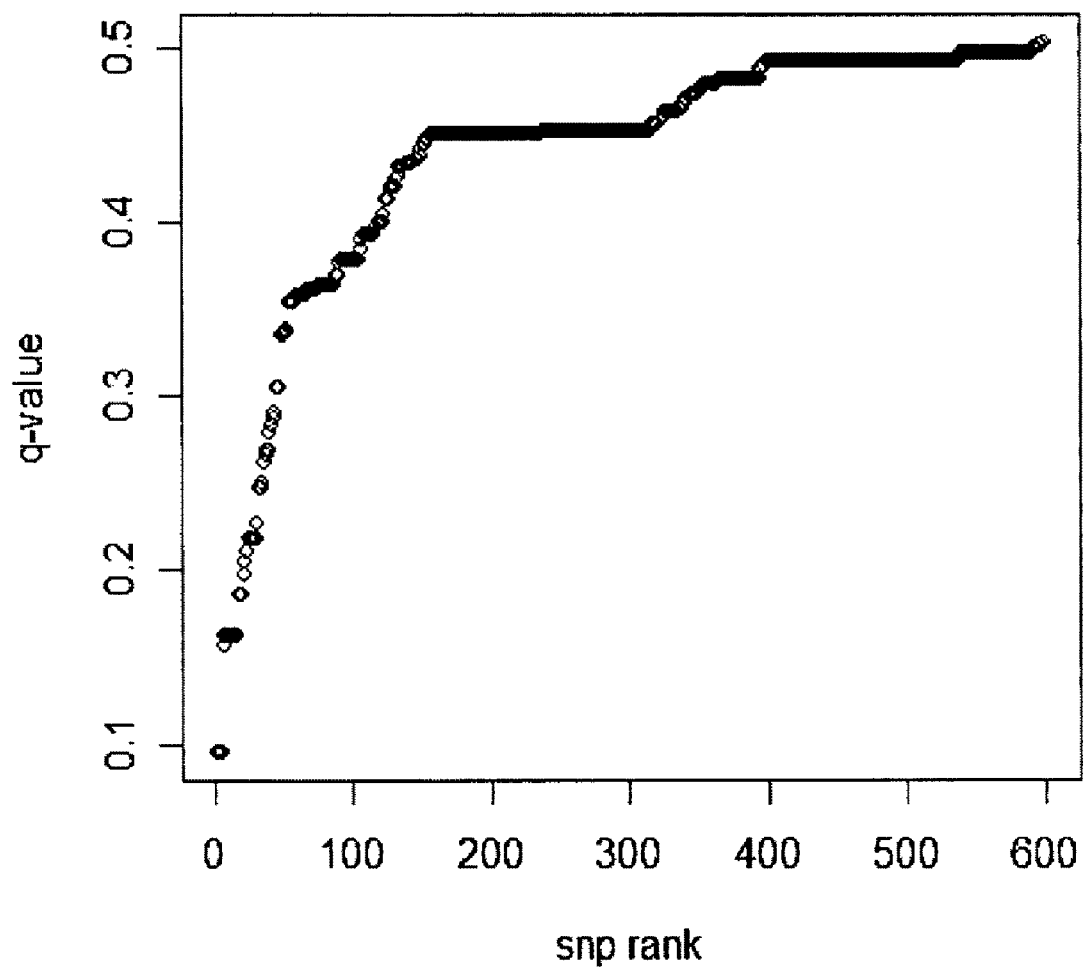
FIG. 8 shows a zoomed-in section of the first 600 SNPs.

False discovery rate (FDR) q-values were computed using Storey procedure separately for the candidate gene region. The FDR q-values were computed from both the p-values obtained from trend scores of the full set of samples and from the p-values from the linear and logistic regressions. The top 6 SNPs in the candidate gene region have q-values computed from the logistic regression <10% and 591 SNPs have q-value <50%. The plot in FIG. 7 shows the FDR q-values in an ordered set of SNPs by their logistic regression p-values. The zoomed-in section of the first 600 SNPs is shown in FIG. 8.

Figure 9:
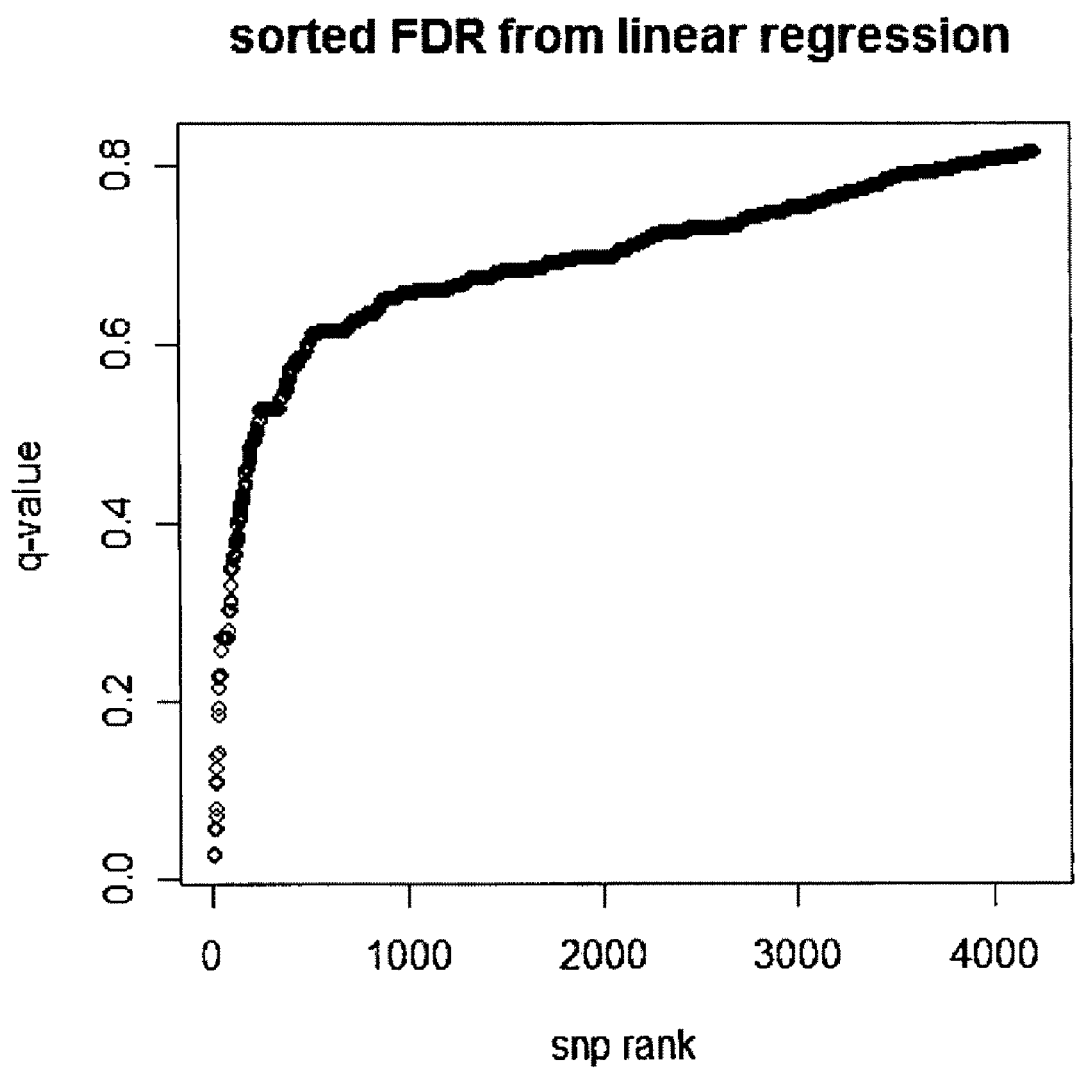
FIG. 9 shows an ordered distribution plot from Example 1.
Figure 10:
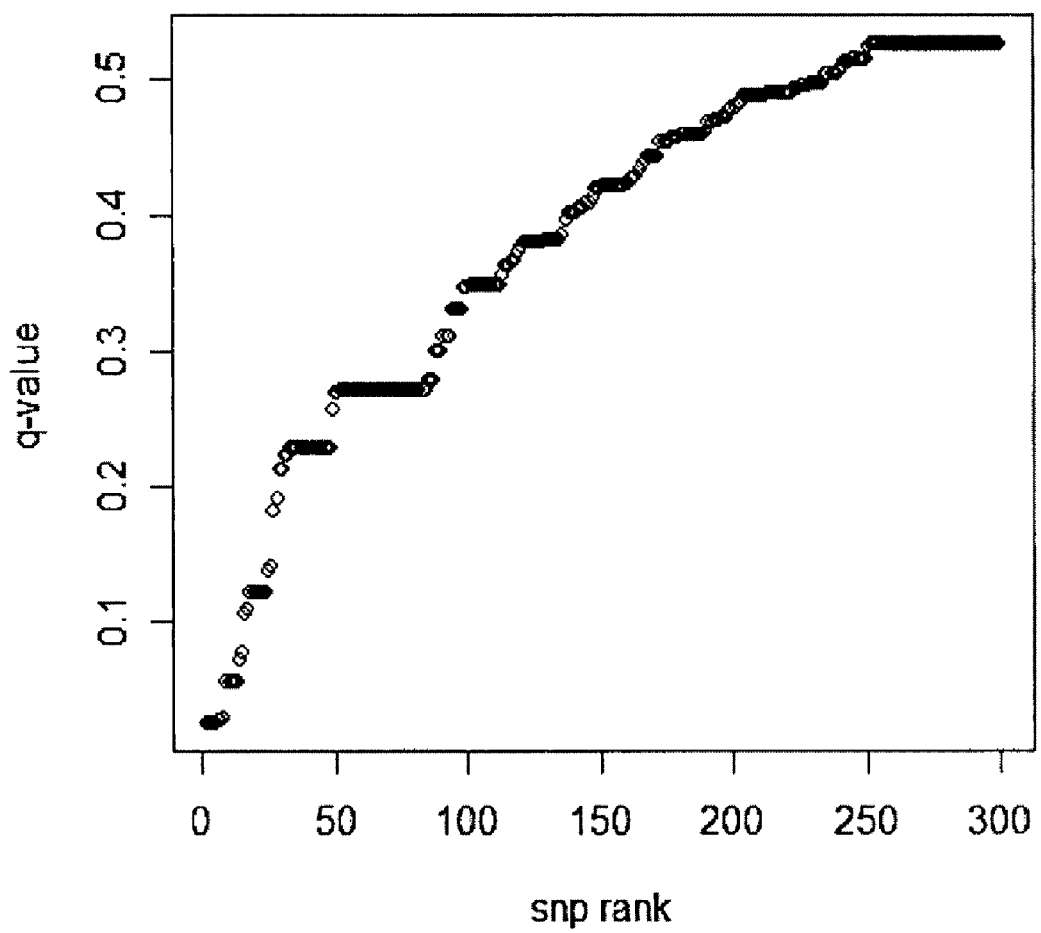
FIG. 10 shows a zoomed in section of the first 300 SNPs.

The linear regression provided 15 SNPs with FDR q-value <10% and 234 SNPs with FDR q-value <50%. The plots in FIGS. 9 and 10 show their ordered distribution, with FIG. 10 depicting the zoomed-in section of the first 300 SNPs.

Analysis of the Pooled SNPs

The pooled SNPs yielded 31,162 reliable SNPs. No SNP showed genome-wide significant p-value from either the logistic or linear regression from the round 1 IG or from the full set of samples. No SNP is also significant in the replication sample set with p-value corrected only for the number of SNPs from PG (p<0.05/31162).

Figure 11:
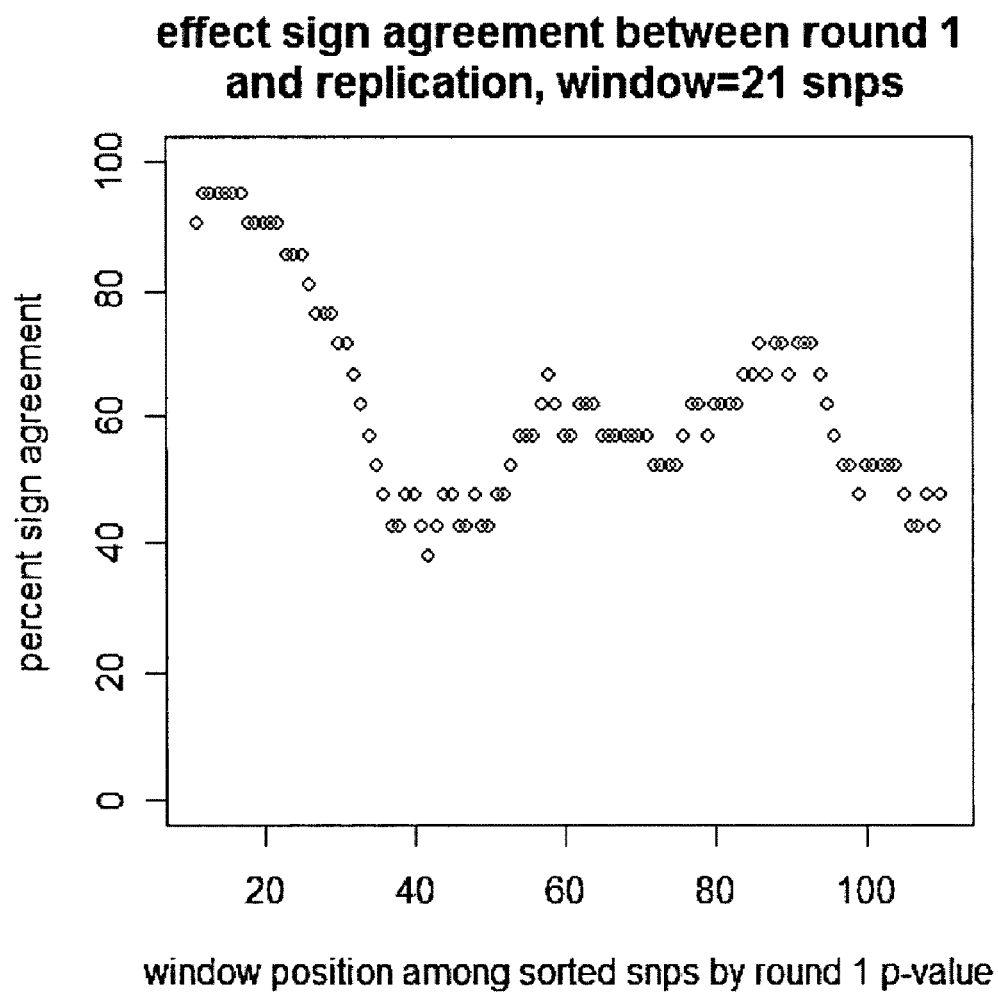
FIG. 11 shows the sign agreement over a sliding window of 21 SNPs in Example 1.
Figure 12:
FIG. 12 shows sign agreement with window size 101 of FIG. 11 in Example 1.

Inspection of the sign agreement between the round 1 allele frequency differences between cases and controls and replication allele frequency differences shows somewhat higher sign agreement among the top SNPs sorted by the round 1 trend score p-values. FIG. 11 shows the sign agreement over a sliding window of 21 SNPs. The first about 20 SNPs do show above average agreement of the delta allele frequency signs, as shown in FIG. 11. The agreement is very significant, as the p-value from binomial distribution of obtaining 19 agreements out of 21 trials is 1.04e-5. Therefore the probability that the first bin composed of the 21 most significant SNPs will have by chance 19 agreements is 1.04e-5. The agreement deteriorates quickly though, as the plot with window size 101 in FIG. 12 shows. From this plot is seems that about first 75 to 100 SNPs are still enriched for agreement between round 1 and replication.

FDR cannot be computed for the pooled SNPs and the samples that were used in the PG as the SNPs are selected from the PG and therefore SNPs showing any population differences between the PG samples that are not related to the phenotype are selected here as well. Therefore the SNPs are expected to be enriched for small p-values that will show in that set of samples. However, there is no such expectation for the replication samples that did not participate in the SNP selection and therefore FDR can be computed from that set. FDR q-values computed from both linear and logistic regression p-values have rather large values—linear regression provides smallest q-value 0.57 and the logistic regression smallest q-value is 0.43.

Example 2

Addiction Markers

The SNPs set forth in Table 1 were identified as being associated with nicotine addiction risk based on the individual genotyping results from the study. Sequences for the given dbSNP rsID numbers are found on the internet at the National Center for Biotechnology Information website. Positions refer to NCBI Build 35 of the human genome. Allele frequencies in cases and controls refer to the frequency of an arbitrarily designated reference allele of the SNP.

The SNPs were selected according to the following criteria: 1) call rate >80%; 2) HWE p-value in cases and in controls >1e-15; 3) SNPs with HWE p-value in either cases or controls between 1e-4 and 1e-15 were inspected visually and bad SNPs were excluded; 4) 3 SNPs that show fixed difference between males and females were excluded. The SNPs were selected as the top SNPs in the two categories (from pooled study or selected for candidate gene region coverage) based on a p-value from Logistic regression ANOVA test, testing for genotype association after excluding the effect of gender and DNA collection site. The columns in Table 1 generally refer to the individual genotyping phase of the study and are described in detail supra.

Example 3

An Amino Acid Substitution in the α5 nAChR Gene Influences Risk for Nicotine Dependence A nonsynonymous SNP in the nicotinic receptor gene CHRNA5 was found to be associated with nicotine dependence and causes a 2-fold increase in risk through a recessive mode of inheritance.

Nicotine dependence is one of the world's leading causes of preventable death. To discover genetic variants that influence risk for nicotine dependence, over three hundred candidate genes were targeted for genotyping and 3,713 single nucleotide polymorphisms (SNPs) in were analyzed in 1,050 cases and 879 controls. The Fagerström test for nicotine dependence (FTND) was used to assess dependence, where cases were required to have an FTND of 4 or more. The control criterion was strict: control subjects must have smoked at least 100 cigarettes in their lifetimes and had an FTND of 0 during the heaviest period of smoking. After correcting for multiple testing by controlling the false discovery rate, several cholinergic nicotinic receptor (nAChR) genes dominated the top signals. The strongest association was from a SNP representing CHRNB3, the beta3 nicotinic receptor subunit gene ($p=9.4\times10^{-5}$). Biologically, the most compelling evidence for a risk variant came from a nonsynonymous SNP in the alpha5 nicotinic receptor subunit gene CHRNA5 ($p=6.4\times10^{-4}$). This SNP exhibited evidence of a recessive mode of inheritance, resulting in individuals having a two-fold increase in risk of developing nicotine dependence once exposed to cigarette smoking. Other genes among the top signals were KCNJ6 and GABRA4. This example represents one of the most powerful and extensive studies of nicotine dependence, and has found novel risk loci which are optionally confirmed by replication studies.

The World Health Organization estimates that if current trends continue the annual number of deaths from tobacco-related diseases will double from 5 million in the year 2000 to 10 million in 2020. (1,2) Nicotine, a naturally occurring alkaloid found in tobacco, mimics acetylcholine, and nicotine's ability to bind to nicotinic cholinergic receptors (nAChRs)

underlies the molecular basis of nicotine dependence (susceptibility to tobacco addiction, [MIM 188890]). Chronic nicotine exposure produces long-lasting behavioral and physiological changes that include increased synaptic strength, altered gene expression, and nAChR up-regulation. (3) Although nAChRs are expressed throughout the central nervous system, the addictive effects of nicotine are thought to be mediated through mesocorticolimbic dopamine (DA) pathways. (4) It is believed that the interplay among glutamate, dopamine, and gamma-aminobutyric acid (GABA) systems is critical for the reinforcing effects of nicotine. (3, 5) Cigarettes are the predominant form of tobacco used worldwide (6), and genetic factors are important to the etiology of nicotine dependence, with estimates of the heritability ranging from 44% to 60% (7).

Efforts to identify susceptibility loci influencing cigarette smoking behavior through association studies have used a candidate gene approach with both case-control and family-based designs. Several candidate genes that may influence smoking have been studied, including nicotinic receptors (8-10), nicotine metabolizing genes (11-13), dopamine system receptors (14-17), GABA receptors (18), and other neurotransmitters and receptors (19-21). There appears to be very little concordance among linkage findings and association findings in candidate genes (reviewed in 22). One genome-wide association study (GWAS) paper to date is by Bierut et al. (23), which was conducted in parallel with the current example study and used the same case-control sample.

The approach of this example was to target an extensive set of candidate genes for SNP genotyping to detect variants associated with nicotine dependence using a case-control design. Over three-hundred genes for genotyping were targeted, with a design that allowed for approximately 4,000 SNPs. These included the gene families encoding nicotinic receptors, dopaminergic receptors and gamma-aminobutyric acid receptors, which are known to be part of the biological pathways involved in dependence. This was done in conjunction with a genome-wide association study (GWAS), see Example 4, and Bierut (23). Both studies used a large sample of cases and controls of European descent. The 1,050 nicotine dependent cases were contrasted with a unique control sample of 879 individuals who are non-dependent smokers. The size of the sample and strict control criteria should provide ample power to detect variants influencing nicotine dependence, but the depth of the coverage of known candidate genes is ambitious and requires delicate handling to deal with the complex issue of multiple testing. The false discovery rate (FDR) was used to limit the effects of multiple testing (23,24), and to report on the top FDR-controlled list of associations.

Results of Example 3

The list of candidate genes of the example initially numbered 448, and was divided into categories "A" and "B." All category 55 "A" genes were targeted for SNP genotyping, but because it was beyond easy resources to target all of the remaining 393 category "B" genes, these were prioritized for SNP genotyping according to the results of the pooled genotyping in a parallel GWAS (see, Bierut (23) and Example 4). Table 5 shows a summary of the results of the pooled genotyping in the candidate genes. Out of the 393 category "B" genes considered for SNP selection, 296 were targeted for individual genotyping in the candidate gene study. These were chosen using the lowest corrected minimum p-values, as defined in Equation 1 (see below), where the cutoff was approximately $p \leq 0.95$. 4,309 SNPs in these candidate genes were individually genotyped, and after quality control filtering, 3,713 SNPs were tested for association. There were 515 SNPs tested for 52 Category A genes and 3,198 SNPs tested for 296 Category B genes.

TABLE 5

| Category | Candidate Genes | Genes Tested | SNPs Tested | Corrected Minimum p-value ($p_{corr}$) | | |
|---|---|---|---|---|---|---|
| | | | | Min | Max | $\mu \pm \sigma^a$ |
| A | 55 | 52 | 1,604 | 0.0017 | 0.94 | 0.33 ± 0.28 |
| B | 393 | 367 | 29,071 | 0.0021 | 0.99 | 0.41 ± 0.28 |
| Total | 448 | 419 | 30,675 | | | |

Table 5 shows results of the pooled genotyping in the candidate genes from the parallel genome-wide association study (GWAS). A total of 2,177,718 SNPs passed quality control (QC) measures and were tested for association. The results were used to rank the category B genes for SNP selection. The "Genes Tested" and "SNPs Tested" columns show the number of genes and number of SNPs in those genes that passed QC and were tested for association. The minimum p-value over all SNPs tested for association in the pooled genotyping within a gene is corrected for the number of tests according to equation (1). $^a$Mean±standard deviation.

In Table 6, top associations with nicotine dependence where the weighted FDR is less than 40% are shown. SNPs from Category "A" genes were weighted 10-fold more heavily than Category "B" genes when estimating FDR. The signals are sorted by the primary 2 degree of freedom p-value of adding the genotype term and the genotype by gender interaction term to the base model in the logistic regression. SNPs with function "FP" are within the footprint of the gene, defined for display purposes as ±10 Kb of the transcribed region. Those labeled "LD BIN" are outside of the footprint and were selected for genotyping for being in LD with SNPs near an exon. Genes in parentheses are the candidate genes for which the SNP was selected. The "LD Bin ID" column identifies LD bins; SNPs with the same LD Bin ID effectively produce a single association signal. This reports the minimum correlation between the tag and other SNPs in the bin in the "Min($r^2$)" column. The rank is determined by the primary p-value in all 3,713 genotyped SNPs. All alleles were reported from the positive strand. The frequency of the risk allele (the allele more frequent in cases than in controls) in cases p and controls q is reported with the notation p/q.

TABLE 6

| SNP | Gene | Function | Category | Chr | Pos (bp) | LD Bin ID | Min($r^2$) | Risk Allele | Primary p-value | Rank | FDR |
|---|---|---|---|---|---|---|---|---|---|---|---|
| rs6474413 | CHRNB3 | FP | A | 8 | 42,670,221 | 8-19 | 0.991 | T (0.81/0.76) | 9.36E−05 | 1 | 0.056 |
| rs10958726 | CHRNB3 | LD BIN | A | 8 | 42,655,066 | 8-19 | 0.991 | T (0.81/0.76) | 1.33E−04 | 2 | 0.056 |
| rs578776 | CHRNA3 | UTR | A | 15 | 76,675,455 | — | — | G (0.78/0.72) | 3.08E−04 | 3 | 0.086 |
| rs6517442 | KCNJ6 | FP | B | 21 | 38,211,816 | — | — | C (0.34/0.28) | 5.62E−04 | 4 | 0.344 |
| rs16969968$^a$ | CHRNA5 | NONSYN | A | 15 | 76,669,980 | 15-13 | 0.989 | A (0.38/0.32) | 6.42E−04 | 5 | 0.134 |

TABLE 6-continued

| SNP | Gene | Function | Category | Chr | Pos (bp) | LD Bin ID | Min($r^2$) | Risk Allele | Primary p-value | Rank | FDR |
|---|---|---|---|---|---|---|---|---|---|---|---|
| rs3762611 | GABRA4 | FP | B | 4 | 46,838,216 | 4-71 | 0.939 | G (0.93/0.91) | 9.22E-04 | 6 | 0.344 |
| rs1051730 | CHRNA3 | SYNON | A | 15 | 76,681,394 | 15-13 | 0.989 | A (0.38/0.32) | 9.93E-04 | 7 | 0.166 |
| rs10508649[b,c] | PIP5K2A | SYNON | B | 10 | 22,902,288 | — | — | T (1.00/0.99) | 1.02E-03 | 8 | 0.344 |
| rs17041074[b] | DAO | INTRON | B | 12 | 107,794,340 | — | — | A (0.27/0.26) | 1.12E-03 | 9 | 0.344 |
| rs3762607[b] | GABRA4 | FP | B | 4 | 46,837,266 | 4-71 | 0.939 | A (0.93/0.91) | 1.22E-03 | 10 | 0.344 |
| rs2767 | CHRND | UTR | A | 2 | 233,225,579 | 2-68 | 0.887 | G (0.39/0.34) | 1.50E-03 | 11 | 0.209 |
| rs6772197[b] | DOCK3 (GRM2) | INTRON | B | 3 | 51,126,839 | 3-46 | 0.923 | A (0.84/0.83) | 1.66E-03 | 12 | 0.384 |
| rs3021529[b] | AVPR1A | UTR | B | 12 | 61,831,947 | 12-10 | 0.842 | G (0.86/0.85) | 1.73E-03 | 13 | 0.384 |
| rs1206549 | CLTCL1 | INTRON | B | 22 | 17,590,414 | 22-5 | 0.996 | G (0.86/0.82) | 1.75E-03 | 14 | 0.384 |
| rs637137 | CHRNA5 | INTRON | A | 15 | 76,661,031 | 15-3 | 0.801 | T (0.81/0.76) | 2.82E-03 | 22 | 0.336 |
| rs3791729 | CHRND | INTRON | A | 2 | 233,220,802 | 2-68 | 0.887 | A (0.36/0.32) | 3.39E-03 | 25 | 0.344 |
| rs4531 | DBH | NONSYN | A | 9 | 133,538,924 | — | — | G (0.93/0.91) | 5.10E-03 | 30 | 0.344 |
| rs3025382[a] | DBH | INTRON | A | 9 | 133,531,875 | — | — | G (0.90/0.88) | 5.14E-03 | 31 | 0.344 |
| rs7877 | FMO1 | UTR | A | 1 | 167,986,548 | 1-60 | 0.890 | C (0.74/0.70) | 6.33E-03 | 38 | 0.344 |
| rs6320[b] | HTR5A | SYNON | A | 7 | 154,300,269 | — | — | T (0.72/0.71) | 6.50E-03 | 39 | 0.344 |
| rs4802100[b] | CYP2B6 | FP | A | 19 | 46,187,865 | 19-4 | 0.995 | G (0.10/0.08) | 6.76E-03 | 41 | 0.344 |
| rs2304297 | CHRNA6 | UTR | A | 8 | 42,727,356 | 8-52 | 0.830 | G (0.79/0.75) | 6.91E-03 | 42 | 0.344 |
| rs3760657 | CYP2B6 | FP | A | 19 | 46,187,273 | 19-4 | 0.995 | G (0.10/0.08) | 6.98E-03 | 43 | 0.344 |
| rs2276560 | CHRNG | LD BIN | A | 2 | 233,276,424 | 2-63 | 0.931 | T (0.77/0.74) | 7.42E-03 | 44 | 0.344 |
| rs742350 | FMO1 | SYNON | A | 1 | 167,981,702 | 1-7 | 0.971 | C (0.87/0.84) | 8.45E-03 | 48 | 0.344 |
| rs684513 | CHRNA5 | INTRON | A | 15 | 76,645,455 | 15-3 | 0.801 | C (0.82/0.78) | 8.72E-03 | 49 | 0.344 |
| rs510769[a] | OPRM1 | INTRON | A | 6 | 154,454,133 | — | — | T (0.27/0.24) | 9.84E-03 | 58 | 0.344 |
| rs4245150[b] | DRD2 | LD BIN | A | 11 | 112,869,857 | 11-8 | 0.998 | G (0.37/0.36) | 1.08E-02 | 61 | 0.344 |
| rs3743078 | CHRNA3 | INTRON | A | 15 | 76,681,814 | 15-3 | 0.801 | G (0.83/0.79) | 1.10E-02 | 63 | 0.344 |
| rs1657273[b] | HTR5A | LD BIN | A | 7 | 154,317,817 | 7-29 | 0.976 | G (0.69/0.68) | 1.11E-02 | 64 | 0.344 |
| rs17602038 | DRD2 | LD BIN | A | 11 | 112,869,901 | 11-8 | 0.998 | C (0.37/0.36) | 1.17E-02 | 69 | 0.344 |
| rs3813567 | CHRNB4 | FP | A | 15 | 76,721,606 | — | — | A (0.83/0.79) | 1.18E-02 | 70 | 0.344 |
| rs893109 | HTR5A | LD BIN | A | 7 | 154,330,522 | 7-29 | 0.976 | G (0.69/0.68) | 1.24E-02 | 73 | 0.344 |
| rs16864387 | FMO1 | UTR | A | 1 | 168,015,501 | 1-7 | 0.971 | T (0.87/0.84) | 1.28E-02 | 74 | 0.344 |
| rs6045733[b] | PDYN | LD BIN | A | 20 | 1,898,858 | 20-32 | 0.810 | G (0.66/0.65) | 1.55E-02 | 84 | 0.384 |
| rs4953 | CHRNB3 | SYNON | A | 8 | 42,706,816 | 8-13 | 1.000 | G (0.97/0.95) | 1.61E-02 | 85 | 0.384 |
| rs4952 | CHRNB3 | SYNON | A | 8 | 42,706,222 | 8-13 | 1.000 | C (0.97/0.95) | 1.63E-02 | 87 | 0.384 |
| rs6749955 | CHRNG | LD BIN | A | 2 | 233,263,422 | 2-63 | 0.931 | T (0.77/0.73) | 1.70E-02 | 91 | 0.384 |
| rs7517376 | FMO1 | SYNON | A | 1 | 167,983,945 | 1-7 | 0.971 | A (0.87/0.84) | 1.80E-02 | 95 | 0.384 |

[a]There is significant evidence for a non-multiplicative model, see Table 8 (which shows one SNP per LD bin);
[b]There is significant evidence for gender-specific risk, see Table 9 (which shows 1 SNP per LD bin);
[c]Very low minor allele frequency.

Table 7 shows details of all category "A" genes and any category "B" genes with SNPs among the top signals (that is, SNPs that appear in Table 6). The column "SNPs tested" refers to the number of SNPs tested for association, and the column "SNPS in Top Signals" refers to the SNPs that appear in Table 6. Some SNPs represent multiple genes, particularly when two genes are near each other; hence there is overlap between genes for the SNPs represented by these two columns. Genes with SNPs in our top signals are shown in boldface.

TABLE 7

| Gene | Chr | 5' Position (Mb) | Size (Kb) | Strand | SNPs Tested | SNPs Tested per Kb | SNPs in Top Signals |
|---|---|---|---|---|---|---|---|
| Category A | | | | | | | |
| ADRBK2 | 22 | 24.286 | 159 | + | 5 | 0.0 | 0 |
| ANKK1 | 11 | 112.764 | 12.6 | + | 23 | 1.8 | 0 |
| ARRB2 | 17 | 4.561 | 11.0 | + | 3 | 0.3 | 0 |
| BDNF | 11 | 27.700 | 66.8 | − | 10 | 0.1 | 0 |
| CCK | 3 | 42.281 | 6.9 | − | 13 | 1.9 | 0 |
| CHRNA1 | 2 | 175.455 | 16.6 | − | 3 | 0.2 | 0 |
| CHRNA10 | 11 | 3.649 | 5.8 | − | 3 | 0.5 | 0 |
| CHRNA2 | 8 | 27.393 | 18.5 | − | 17 | 0.9 | 0 |
| CHRNA3 | 15 | 76.700 | 25.7 | − | 18 | 0.7 | 5 |
| CHRNA4 | 20 | 61.463 | 16.7 | − | 8 | 0.5 | 0 |
| CHRNA5 | 15 | 76.645 | 28.6 | + | 18 | 0.6 | 6 |
| CHRNA6 | 8 | 42.743 | 15.8 | − | 4 | 0.3 | 1 |
| CHRNA7 | 15 | 30.11 | 138.5 | + | 13 | 0.1 | 0 |
| CHRNA9 | 4 | 40.178 | 19.5 | + | 11 | 0.6 | 0 |
| CHRNB1 | 17 | 7.289 | 12.5 | + | 10 | 0.8 | 0 |
| CHRNB2 | 1 | 151.353 | 8.8 | + | 4 | 0.5 | 0 |
| CHRNB3 | 8 | 42.672 | 39.6 | + | 6 | 0.2 | 5 |
| CHRNB4 | 15 | 76.721 | 17.0 | − | 14 | 0.8 | 5 |
| CHRND | 2 | 233.216 | 9.3 | + | 3 | 0.3 | 2 |
| CHRNE | 17 | 4.747 | 5.3 | + | 3 | 0.6 | 0 |
| CHRNG | 2 | 233.23 | 6.0 | + | 6 | 1.0 | 4 |
| CNR1 | 6 | 88.912 | 5.5 | − | 9 | 1.6 | 0 |
| COMT | 22 | 18.304 | 27.2 | + | 13 | 0.5 | 0 |
| CYP2A6 | 19 | 46.048 | 6.9 | − | 3 | 0.4 | 0 |
| CYP2B6 | 19 | 46.189 | 27.1 | + | 14 | 0.5 | 2 |
| DBH | 9 | 133.531 | 23.0 | + | 10 | 0.4 | 2 |
| DDC | 7 | 50.386 | 85.7 | − | 30 | 0.4 | 0 |
| DRD1 | 5 | 174.804 | 3.1 | + | 4 | 1.3 | 0 |
| DRD2 | 11 | 112.851 | 65.6 | − | 29 | 0.4 | 2 |
| DRD3 | 3 | 115.38 | 50.2 | − | 8 | 0.2 | 0 |
| DRD5 | 4 | 9.460 | 2.0 | + | 4 | 2.0 | 0 |
| FAAH | 1 | 46.572 | 19.5 | + | 5 | 0.3 | 0 |
| FMO1 | 1 | 167.949 | 37.5 | + | 14 | 0.4 | 4 |
| FMO3 | 1 | 167.792 | 26.9 | + | 23 | 0.9 | 0 |
| GABRB2 | 5 | 160.908 | 254.3 | − | 14 | 0.1 | 0 |
| GPR51 | 9 | 98.551 | 421.1 | − | 29 | 0.1 | 0 |
| HTR1A | 5 | 63.293 | 1.3 | − | 5 | 3.9 | 0 |
| HTR2A | 13 | 46.368 | 62.7 | − | 20 | 0.3 | 0 |
| HTR5A | 7 | 154.3 | 13.6 | + | 13 | 1.0 | 3 |
| MAOA | 23 | 43.272 | 90.7 | + | 5 | 0.1 | 0 |
| MAOB | 23 | 43.498 | 115.8 | − | 10 | 0.1 | 0 |
| NPY | 7 | 24.097 | 7.7 | + | 22 | 2.9 | 0 |
| OPRD1 | 1 | 28.959 | 51.6 | + | 1 | 0.0 | 0 |

TABLE 7-continued

| Gene | Chr | 5' Position (Mb) | Size (Kb) | Strand | SNPs Tested | SNPs Tested per Kb | SNPs in Top Signals |
|---|---|---|---|---|---|---|---|
| OPRK1 | 8 | 54.327 | 22.2 | − | 12 | 0.5 | 0 |
| OPRM1 | 6 | 154.453 | 80.1 | + | 12 | 0.1 | 1 |
| PDYN | 20 | 1.923 | 15.3 | − | 11 | 0.7 | 1 |
| PENK | 8 | 57.521 | 5.1 | − | 6 | 1.2 | 0 |
| POMC | 2 | 25.303 | 7.7 | − | 2 | 0.3 | 0 |
| SLC6A3 | 5 | 1.499 | 52.6 | − | 5 | 0.1 | 0 |
| SLC6A4 | 17 | 25.587 | 37.8 | − | 8 | 0.2 | 0 |
| TH | 11 | 2.150 | 7.9 | − | 6 | 0.8 | 0 |
| TPH1 | 11 | 18.019 | 19.8 | − | 14 | 0.7 | 0 |
| Category B | | | | | | | |
| AVPR1A | 12 | 61.833 | 6.4 | − | 15 | 2.4 | 1 |
| CLTCL1 | 22 | 17.654 | 112.2 | − | 15 | 0.1 | 1 |
| DAO | 12 | 107.776 | 20.8 | + | 7 | 0.3 | 1 |
| FMO4 | 1 | 168.015 | 27.7 | + | 12 | 0.4 | 4 |
| GABRA4 | 4 | 46.837 | 74.7 | − | 29 | 0.4 | 2 |
| GRM2 | 3 | 51.718 | 9.1 | + | 2 | 0.2 | 1 |
| KCNJ6 | 21 | 38.211 | 291.9 | − | 18 | 0.1 | 1 |
| PIP5K2A | 10 | 23.043 | 177.7 | − | 15 | 0.1 | 1 |

Figure 13:
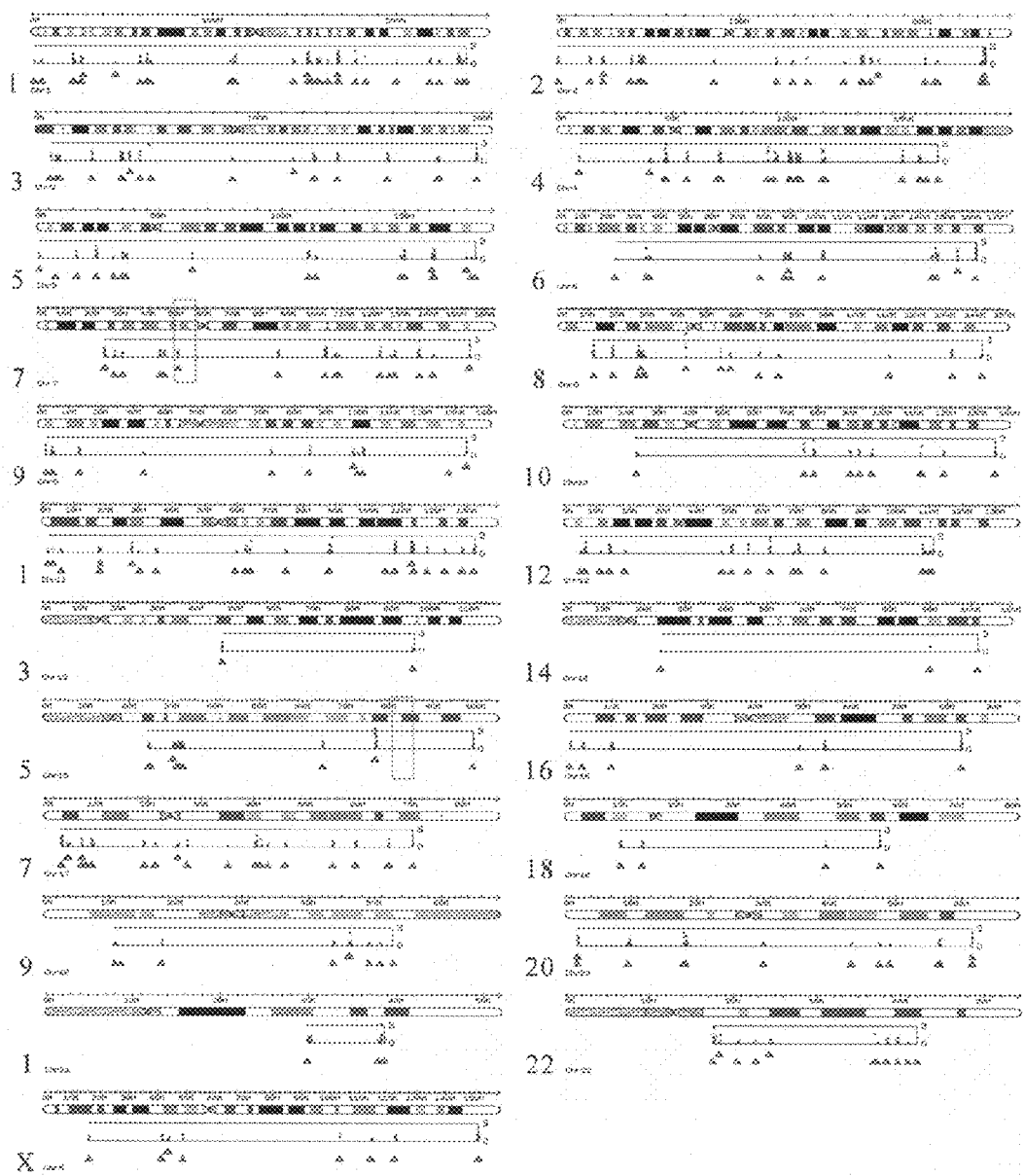
FIG. 13 shows results of the candidate gene association analysis in Example 3.

In the individual genotyping for the candidate genes, the ten smallest p-values from the primary association analysis ranged from $9.36 \times 10^{-5}$ to $1.22 \times 10^{-3}$. There were 39 SNPs with an FDR less than 40%, indicating the presence of about 24 true signals (Tables 5 and 6 and FIG. 13). These top 39 signals were dominated by nicotinic receptor genes (FIGS. 14 and 15). The top 5 FDR values corresponded to the genes CHRNB3, CHRNA3 and CHRNA5 and ranged from 0.056 to 0.166. The best evidence was that four of these five signals were from genuine associations and were not due to random effects. The permutation FDR estimates were roughly the same as the FDR, differing by no more than 0.02, with a minimum permutation FDR of 0.07 at the SNP rs6474413. After selecting a single SNP from each linkage disequilibrium (LD) bin, three of these 39 SNPs showed significant evidence of a non-multiplicative model (Table 8) and several SNPs were found to have a significant gender by genotype interaction (Table 9; also, see Table 14 for a list of all SNPs from Table 6 showing gender by genotype p-values and gender-specific odds ratios). FIG. 13 shows results of the candidate gene association analysis. The p-values from the primary analysis are plotted for each chromosome below an ideogram using the $-\log_{10}(p)$ transformation. The bottom axis is p=1 and the top axis is $p=10^{-3}$. Category "A" genes are shown below the plots in red and Category "B" genes are shown in cyan below the Category "A" genes. Regions on chromosomes 8 and 15, which are shown in more detail in FIG. 14, are highlighted in red. FIG. 15 shows Linkage disequilibrium (LD) between markers in (A) the CHRNB3-CHRNA6 and (B) CHRNA5-CHRNA3-CHRNB4 clusters of nicotinic receptor genes.

Figure 14A:
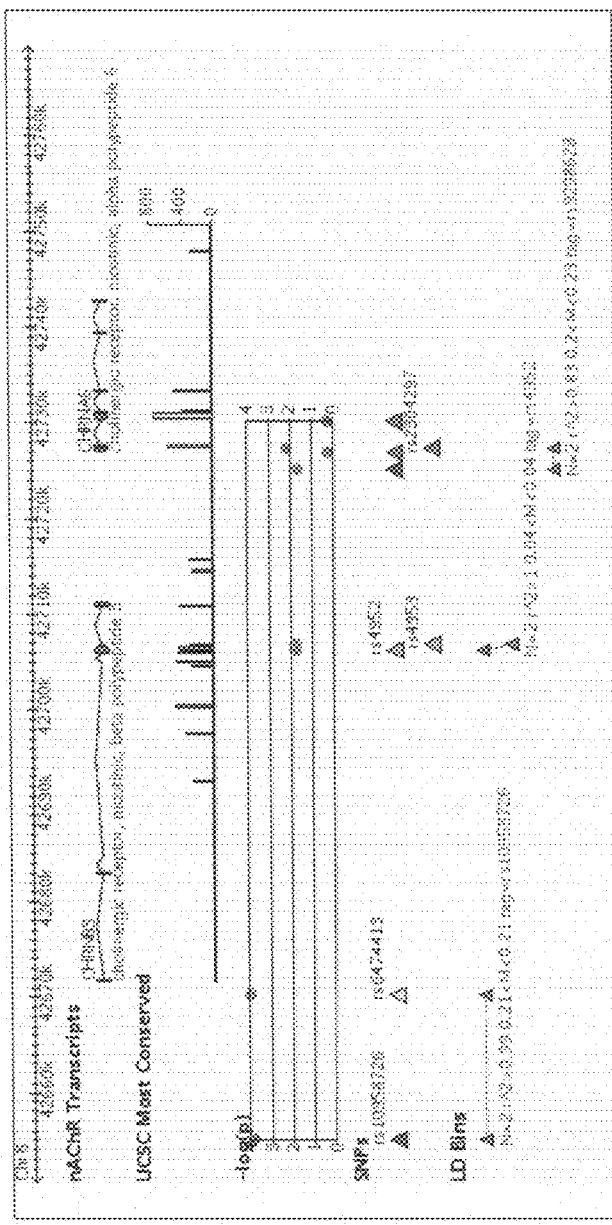
FIG. 14, Panels a-c, shows detailed results for the top association signals in Example 3.

The β3 nicotinic receptor subunit gene CHRNB3, located on chromosome 8, accounted for the two strongest signals from the analysis: rs6474413 and rs10958726 (FIG. 14A). These 2 SNPs effectively contributed a single signal since they were in very high LD with an $r^2$ correlation $\geq 0.99$. They are both in the putative 5' promoter region; the SNP rs6474413 is within 2 Kb of the first 5' promoter and the SNP rs10958726 is an additional 15 Kb upstream. Two other SNPs in CHRNB3, rs4953 and rs4952, were also among the top signals. These are synonymous SNPs in exon 5 and are the only known coding SNPs for CHRNB3 (dbSNP build 125, internet at the National Center for Biotechnology Information website). Again, these represent a single signal as their genotypes were completely correlated. FIG. 14 shows detailed results for the top association signals. (A) The top 2 signals are near the CHRNB3 nicotinic receptor gene on chromosome 8. (B) The nonsynonymous SNP rs16969968 and the CHRNA5-CHRNA3-CHRNB4 cluster of nicotinic receptor genes on chromosome 15. SNPs that appear in Table 6 are labeled with dbSNP rs IDs. The track "UCSC Most Conserved" (on the internet at genome.ucsc.edu, May 2004 build, table "phastConsElements17way") highlights regions conserved between human and other species including the mouse, rat and chicken; the maximum conservation score is 1000. Primary p-values are plotted in red using the $-\log(p)$ transformation. The "LD Bins" track displays the distribution of SNPs from the "SNPs" track into LD bins where all SNPs have $r^2 \geq 0.8$ in both cases and controls with the tag SNP. Only bins with more than 2 SNPs are shown, and bins are annotated with number of SNPs N, the minimum $r^2$ of the tag with the other SNPs in the bin, the range of allele frequencies in the bin, and the tag SNP. (C) A legend indicating the color scheme.

Figure 14B:
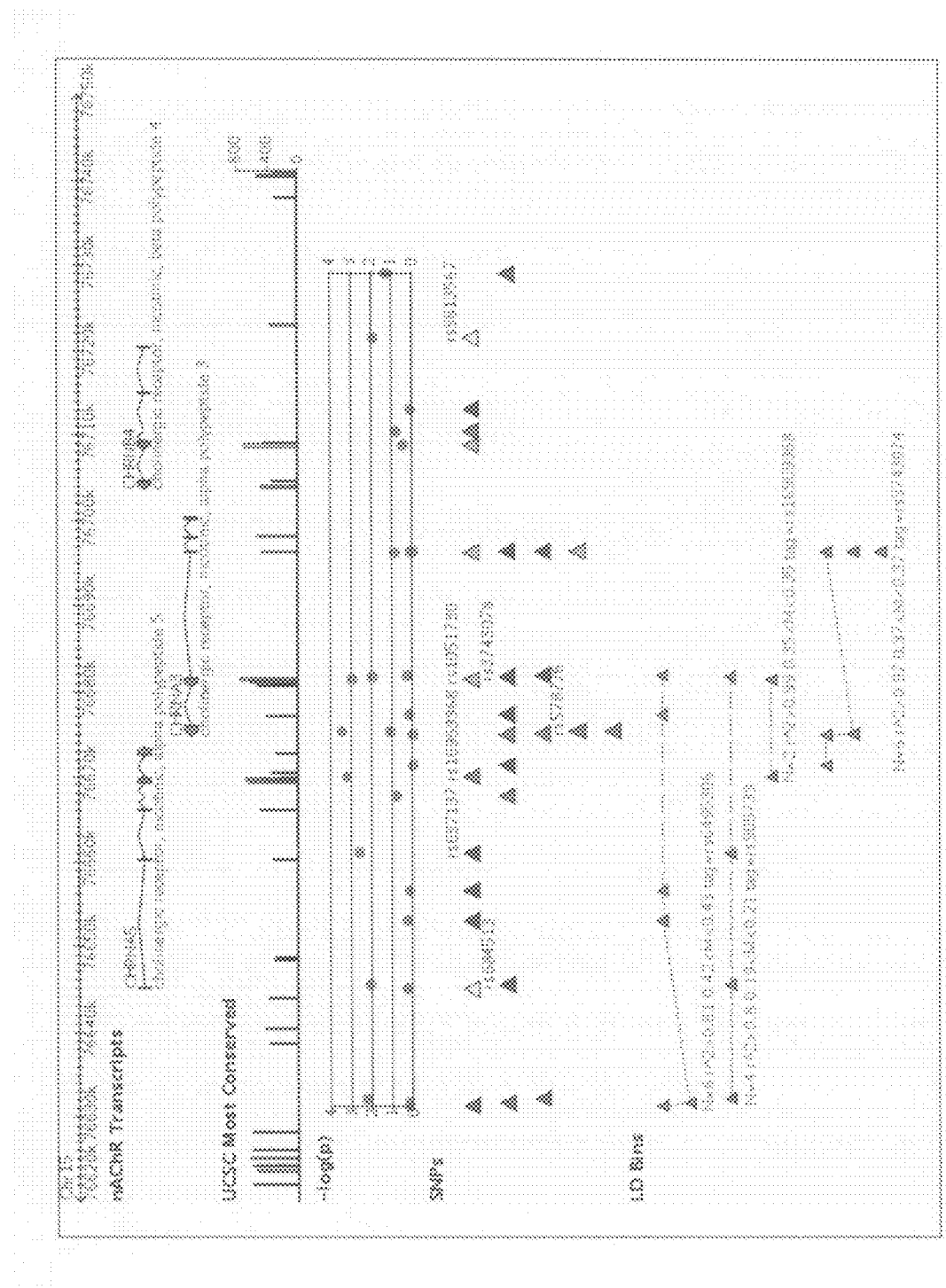
Figure 14C:
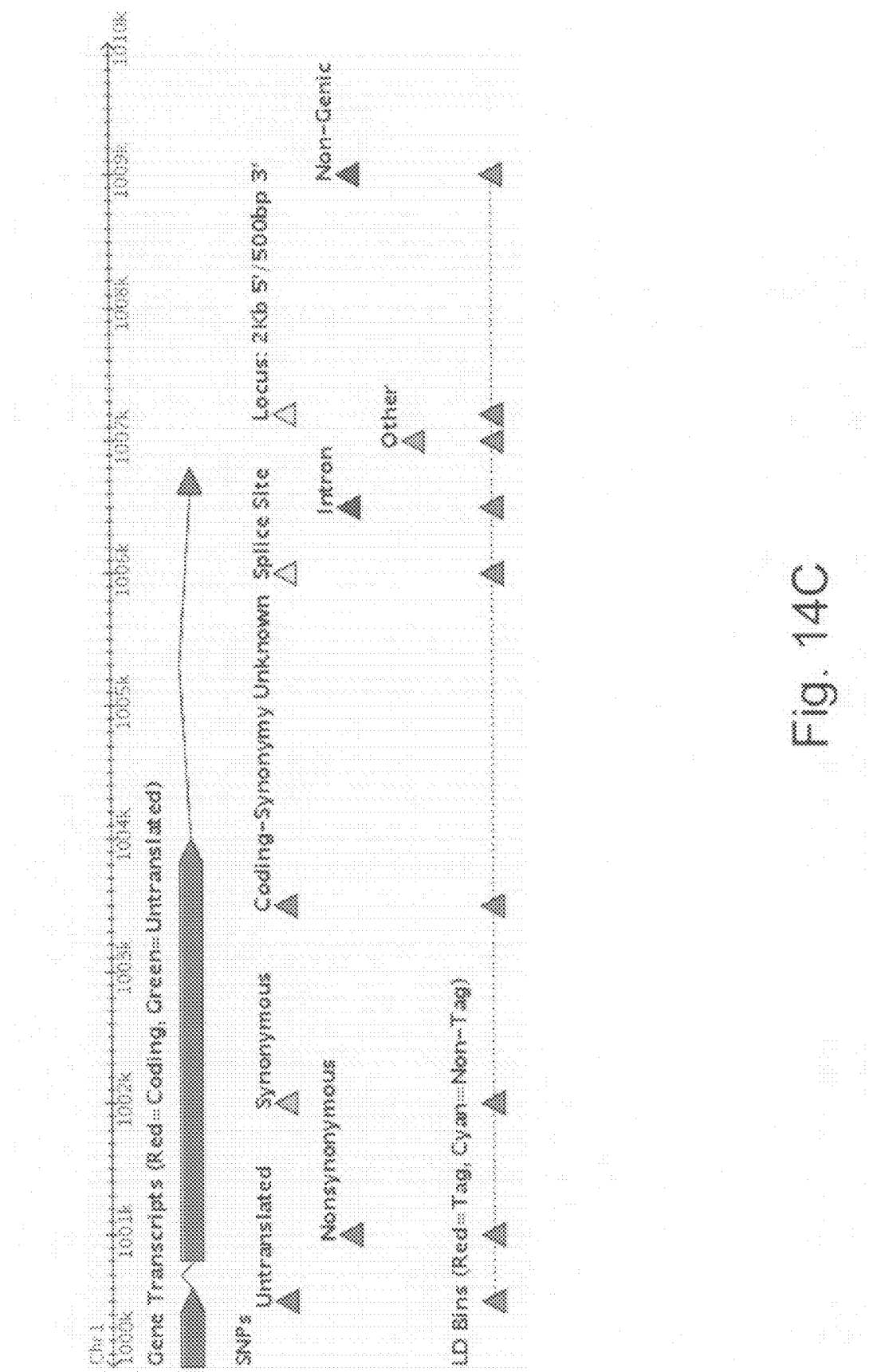
Figure 15A:
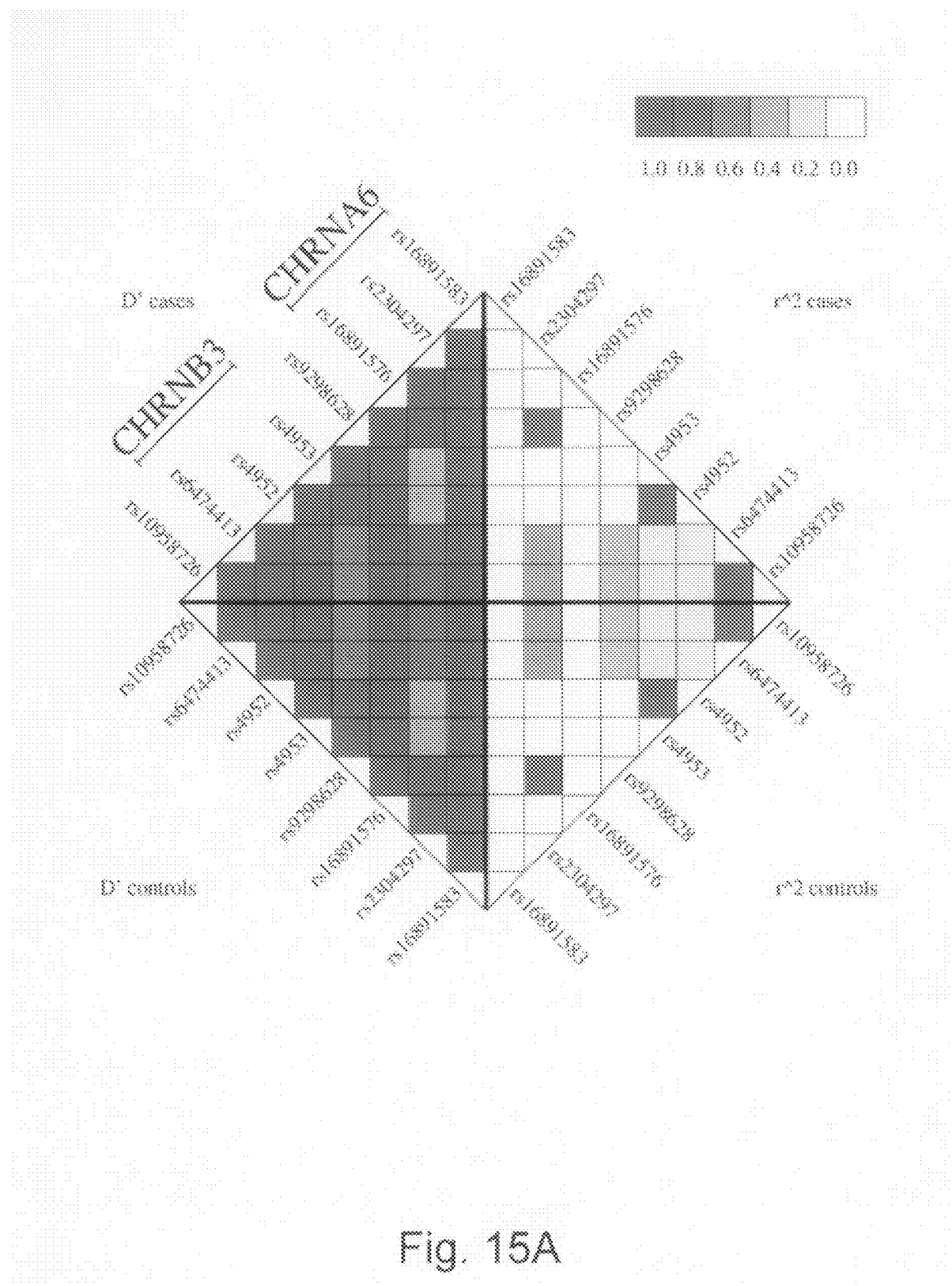
FIG. 15, Panels a and b, shows Linkage disequilibrium (LD) between markers in (A) the CHRNB3-CHRNA6 and (B) CHRNA5-CHRNA3-CHRNB4 clusters of nicotinic receptor genes.
Figure 15B:
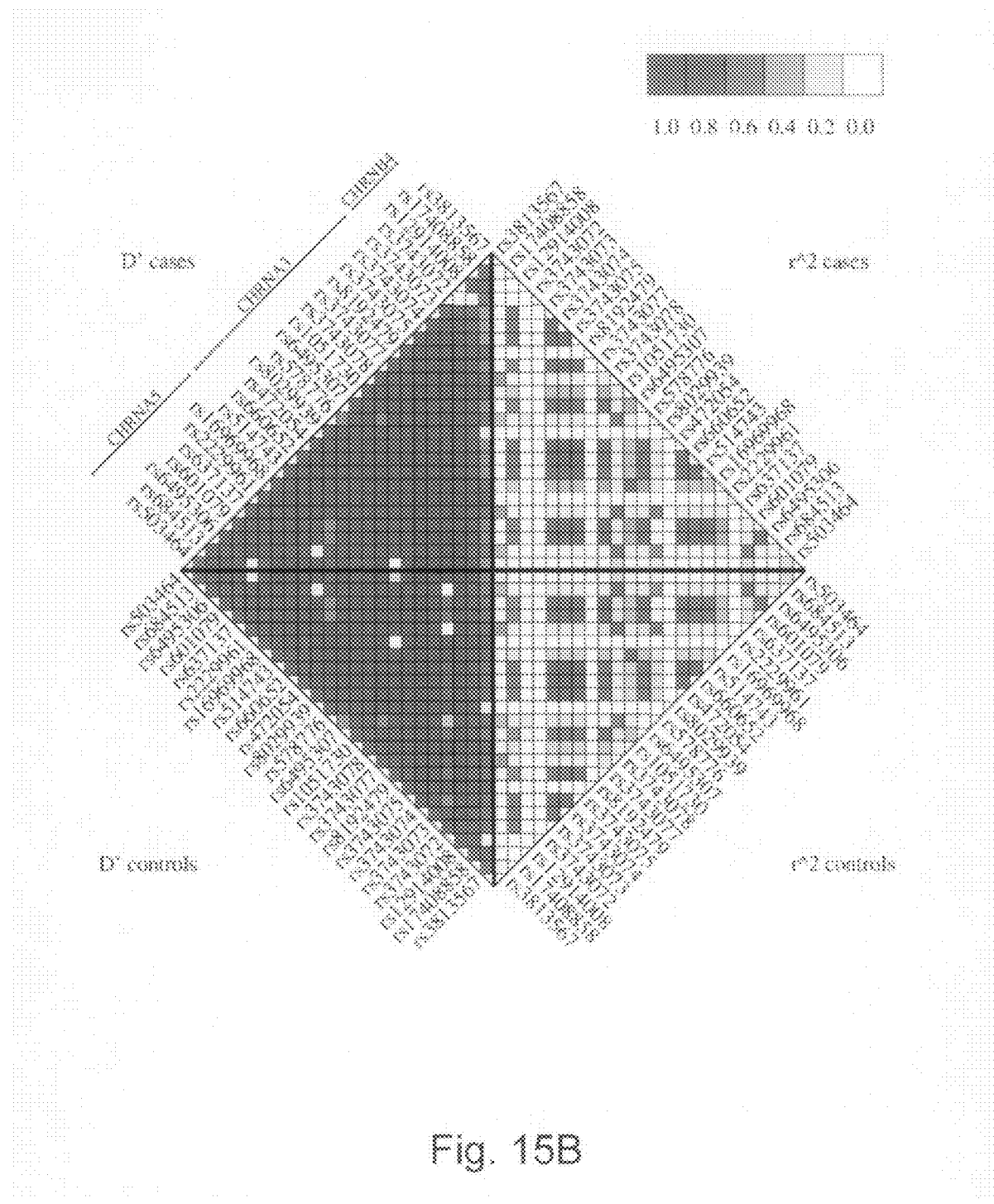

The next group of SNPs among the top signals is in the CHRNA5-CHRNA3-CHRNB4 cluster of nicotinic receptor genes on chromosome 15 (FIG. 14B). The third most significant signal was the SNP rs578776 in the 3' untranslated region (UTR) of CHRNA3, the α3 nicotinic receptor subunit gene (FIG. 14B). Approximately 5 Kb downstream from CHRNA3 is the fifth strongest signal rs16969968, a nonsynonymous coding SNP in exon 5 of CHRNA5, the α5 nicotinic receptor subunit gene. This SNP was in very strong LD with rs1051730, a synonymous coding SNP in CHRNA3, with an $r^2$ correlation $\geq 0.99$.

The most interesting signal appears to be the nonsynonymous SNP rs16969968 in CHRNA5, though as discussed above, it is completely correlated with a SNP in the CHRNA3 gene (FIG. 14B). Allele A of rs16969968 has a frequency of 38% in cases and 32% in controls. There is convincing evidence for a recessive mode of inheritance for this SNP (Table 8). Compared to having no copies, the odds ratio for having 1 copy and 2 copies of the A allele was 1.1 (95% CI 0.9-1.4) and 1.9 (95% CI 1.4-2.6), respectively. That is, compared to individuals with other genotypes, individuals with the AA genotype were nearly twice as likely to have symptoms of nicotine dependence. Table 8 shows SNPs exhibiting significant deviation from a multiplicative genetic model. The SNP with the smallest primary p-value was selected from each LD bin in Table 10. The multiplicative p-value is from the 1 degree of freedom test for the significance of the heterozygote term H in equation (3). We only show SNPs with p<0.05. The last two columns show the odds ratios and 95% confidence intervals for the relative risk between genotypes. The SNP rs16969968 clearly follows a recessive pattern where individuals carrying two copies of the A allele are nearly twice as likely to have symptoms of nicotine dependence compared with those with 0 or 1 copies.

TABLE 8

| SNP | Gene | Non-multiplicative p-value | One Risk Allele Odds Ratio | Two Risk Alleles Odds Ratio |
|---|---|---|---|---|
| rs16969968 | CHRNA5 | 4.04E−02 | 1.1 (0.9-1.4) AG/GG | 1.9 (1.4-2.6) AA/GG |
| rs3025382 | DBH | 2.24E−02 | 0.6 (0.3-1.3) AG/AA | 0.9 (0.4-2.0) GG/AA |
| rs510769 | OPRM1 | 4.16E−04 | 1.5 (1.3-1.9) CT/CC | 1.0 (0.7-1.4) TT/CC |

Discussion of Example 3

Nicotine addiction from tobacco smoking is responsible for over 3 million deaths annually making it the leading cause of preventable mortality in the world (1). In the United States in 2003, 21.6% of adults were smokers, where 24% of men and 19% of women were smokers (26). Previous association studies have been limited to narrowly focused candidate gene studies. This candidate gene study was more extensive, genotyping 3,713 SNPs for 348 candidate in 1,050 nicotine dependent cases and 879 non-dependent smokers, where the control group definition was particularly strict.

The top FDR-controlled findings were dominated by nicotinic receptor genes. The positive association findings for the α5 and β3 nicotinic receptor subunits are novel. Most human genetic and biological studies of the nicotinic receptors and nicotine dependence have focused on the α4 and β2 subunits since they co-occur in high-affinity receptors and are widely expressed in the brain (27). However, mouse studies have demonstrated that of the α4β2 containing receptors that mediate dopamine release, a substantial proportion contain α5 as well (28). This is consistent with the current evidence for an important role of α5 in nicotine dependence susceptibility. Furthermore, in a brain α4β2 receptor, an α5 or β3 subunit can take the fifth position in the pentamer corresponding to β1 of muscle. Although neither α5 nor β3 is thought to participate in forming binding sites, they are able to affect channel properties and influence agonist potency because they participate in the conformational changes associated with activation and desensitization (27).

The most compelling biological evidence of a risk factor for nicotine dependence is from the nonsynonymous SNP rs16969968 in CHRNA5. This SNP causes a change in amino acid 398 from asparagine (encoded by the G allele) to aspartic acid (encoded by A, the risk allele), which results in a change in the charge of the amino acid in the second intracellular loop of the α5 subunit (29). The risk allele appeared to act in a recessive mode, where individuals who were homozygous for the A allele are at a 2 fold risk to develop nicotine dependence. While the α5 subunit has not been studied extensively, and there are no reports of known functional effects of this polymorphism, it is striking that a non-synonymous charge-altering polymorphism in the corresponding intracellular loop of the α4 nAChR subunit has been shown to alter nAChR function in mice in response to nicotine exposure (30-33). This variant is common in the populations of European descent (allele frequency of A allele approximately 42%) but uncommon in populations of Asian or African descent (<5%, data from International HapMap project, on the internet at www.hapmap.org).

Also among the top 39 FDR-controlled signals were the genes KCNJ6 (a.k.a. GIRK2) and GABRA4. These were the only other genes besides nicotinic receptors with SNPs that had p-values less than 0.001. KCNJ6 belongs to the inwardly rectifying potassium channel (GIRK) family of genes. GIRK provides a common link between numerous neurotransmitter receptors and the regulation of synaptic transmission (34). GABA is the major inhibitory neurotransmitter in the mammalian central nervous system, and is critical for the reinforcing effects of nicotine (3,5). Significant evidence was found that the risk due to genotype is much stronger in men than in women (Table 9), where the male odds ratio was 2.2 (95% CI 1.4-3.3).

Previously reported findings in other nicotinic receptors were not among the most significant findings. In prior studies of CHRNA4, nominal association with nicotine dependence measures was reported for the SNPs rs2236196 and rs3787137 in African-American families and rs2273504 and rs1044396 in European Americans, but only rs2236196 in African-Americans remained after multiple testing correction (9). Also in CHRNA4, rs1044396 and rs1044397 were associated with both FTND score and qualitative nicotine dependence in a family-based sample of Asian male smokers (8). In this sample of European descent, 11 SNPs were tested for CHRNA4 including the above mentioned SNPs except rs2273504, which did not pass the stringent quality control standards. The lowest primary p-value across all 11 SNPs was 0.026 for rs2236196 (study-wide rank=132); this particular result may be considered a single test given the specific prior finding for this SNP, and thus provides modest evidence for replication. The remaining four previously reported SNPs that were analyzed showed p-values greater than 0.8. Contrasts in these results are possibly due in part to the different ethnicities of the respective samples.

A recent study of smoking initiation and severity of nicotine dependence in Israeli women (10) analyzed 39 SNPs in 11 nicotinic receptor subunit genes. Their single SNP analyses also did not detect association to SNPs in α4, including rs2236196, rs1044396 and rs1044397, while finding nominal significance in the α7, α9, β2 and β3 subunits. Their study did not include the same SNPs in the β3 subunit and α5-α3-β4 cluster comprising the four strongest associations in nicotinic receptor genes of this example; they did analyze the fifth ranking nicotinic receptor of the example, SNP rs1051730, and found a suggestive p-value of 0.08 when comparing "high" nicotine dependent subjects to "low" nicotine dependent subjects, in a much smaller sample than herein.

This study was unable to corroborate reported association findings of Beuten and colleagues (18) for the β2 subunit of the GABAB receptor GABBR2 (a.k.a. GABABR2, GABAB2 and GPR51). 32 SNPs in GABBR2 were genotyped including five SNPs reported by Beuten and colleagues (18), three of which were the most significant in European Americans by at least one test in that study. The primary p-value in the study herein was greater than 0.07 for all 32 SNPs, and greater than 0.3 for the five previously reported SNPs.

Similarly, no evidence for nominal association was found in the primary test of the 31 SNPs that were genotyped for the DDC gene, which includes a SNP previously reported significant in European-Americans (35). And of the 11 SNPs covering the gene BDNF, three (rs6265, rs2030324, rs7934165) were previously reported as associated in European-American males (21); these three were not significant in the present sample (primary p=0.86, 0.088 and 0.12 respectively), and the lowest primary p-value among the remaining 8 SNPs was 0.02, which does not survive correction for the six LD bins covering the gene. Note that the primary test uses a log-additive model, while previous reports sometimes found their strongest results under other models (e.g., recessive, dominant); however, for these previously reported associations, the present tests for departure from the log-additive model did not find evidence for improvement under alternative modes of inheritance.

The primary association analysis in this example was a two degree of freedom test of the significance of adding genotype and genotype by gender interaction terms to the base predictors sex and site. This approach helps to ensure detection of associations that are significantly influenced by gender. The disadvantage is that the extra degree of freedom makes associations with insignificant gender interaction appear to be less significant overall.

Because the controls herein were highly selected, and could even be considered "protected" against susceptibility to nicotine dependence, interpretation of the results must consider the possibility that an association signal from the study may actually represent protective rather than risk effects. The allele more frequent was used in cases for reporting these data as a convention to facilitate comparison of the odds ratios among SNPs; this should not be viewed as a conclusion of how a particular variant influences the risk for nicotine dependence. The precise determination of the mechanism by which a variant alters risk can only come from functional studies.

Additional tests for association were performed using only the individuals from the United States sample to determine if the primary conclusions still hold in this subset of 797 cases and 813 controls (the Australian sample alone is too small to test for association, with only 253 cases and 66 controls). The same logistic regression method was used as for the entire sample except for the omission of the term "site." The Spearman rank-order correlation of the p-values between the two tests for association was 0.87. Table 15 shows the results of the U.S.-only analysis for the 39 SNPs from the list of top associations (Table 6), with the original ordering and FDR filtering, side by side with results from the U.S. sample. Table 16 describes the result of completely starting over and using only the U.S. sample to order by p-value, filter by FDR <40%, and compute LD bins. In this case, 30/39 (77%) of the SNPs in the original set of top signals (Table 6) appeared in the list of top signals in the U.S.-only analysis (Table 16), which includes the genes CHRNA5 and CHRNB3, the top genes from the initial analysis. Hence, while there were some changes in the order of the results, the primary conclusion of association with the nicotinic receptors CHRNB3 and CHRNA5 remains valid when the analysis is performed on the United States subsample.

As a companion to the candidate gene study, a genome wide association study (GWAS) was carried out in parallel (See below and Bierut (23)). Approximately 2.4 million SNPs were genotyped across the human genome in a two stage design that began with pooled genotyping in a portion of the sample and followed with individual genotyping of the entire sample for the top 40,000 signals. The twenty-first strongest signal from the GWAS was due to a SNP 3 Kb upstream of the first 5' promoter of CHRNB3, the gene with the strongest signal from the candidate gene study. This signal came from the SNP rs13277254 (genotyped only for the GWAS and not for this candidate gene study) and had a p-value of $6.52 \times 10^{-5}$. This convergence from two different study designs provides further support that the signals in this gene are not random effects.

In conclusion, several genetic variants were identified as being associated with nicotine dependence in candidate genes, the majority of which are nicotinic receptor genes. One of the SNPs implicated has a number of biologically relevant consequences, making it a particularly plausible candidate for influencing smoking behavior. These variants should be considered potential sources of genetic risk. Additional research in addition to that of the present application is contemplated to further examine replication and expand on their role in the pharmacogenetics of response to nicotine dosing as well as to treatments for nicotine dependence.

Materials and Methods for Example 3

Subjects

All subjects (Table 10) were selected from two ongoing studies. The Collaborative Genetic Study of Nicotine Dependence (U.S.) recruited subjects from three urban areas in the United States and the Nicotine Addiction Genetics (Australian) study collected subjects of European ancestry from Australia. Both studies used community-based recruitment and equivalent assessments were performed. Subjects that were identified as being smokers, using the criteria that they had smoked 100 or more cigarettes in their lifetimes, were queried in more detail using the FTND questionnaire. The U.S. samples were enrolled at sites in St. Louis, Detroit, and Minneapolis, where a telephone screening of community based subjects was used to determine if subjects met criteria for case (current FTND$\geq$4) or control status. The study participants for the Australian sample were enrolled at the Queensland Institute of Medical Research in Australia, where families were identified from two cohorts of the Australian Twin Panel, which included spouses of the older of these two cohorts, for a total of approximately 12,500 families with information about smoking. The ancestry of the Australian samples is predominantly Anglo-Celtic and Northern European. The Institutional Review Boards approved both studies and all subjects provided informed consent to participate. Blood samples were collected from each subject for DNA analysis and were submitted, together with electronic phenotypic and genetic data for both studies, to the National Institute on Drug Abuse (NIDA) Center for Genetic Studies, which manages the sharing of research data according to the guidelines of the National Institutes of Health.

Case subjects were required to score 4 or more on the Fagerström Test for Nicotine Dependence (FTND) (36) during the heaviest period of cigarette smoking (the largest possible score is 10). This is a common criterion for defining nicotine dependence. Control subjects must have smoked 100 or more cigarettes in their lifetimes, yet never exhibited symptoms of nicotine dependence: they were smokers that scored 0 on the FTND during the heaviest period of smoking. By selecting controls that had a significant history of smoking, the genetic effects that are specific to nicotine dependence can be examined. Additional data from the Australian twin panels supports this designation of a control status (see next Example and (23)). In the U.S. study, using the sample of 15,086 subjects which were determined to be smokers (smoked 100 or more cigarettes lifetime) during the screening process, the prevalence of "nicotine dependence" (FTND was greater than or equal to 4) was 46.4%, and the prevalence of "smoking without nicotine dependence" (FTND=0) was 20.1%.

Candidate Gene Selection

The criteria for the selection of the candidate genes were based on known biology, correlations between nicotine dependence and other phenotypes, and previous reports on the genetics of nicotine dependence and related traits. Genes were nominated by an expert committee of investigators from the NIDA Genetics Consortium (on the internet at zork.wustl.edu/nida) with expertise in the study of nicotine and other substance dependence. These included classic genes that respond to nicotine, such as the nicotinic receptors, and other genes involved in the addictive process.

In all, 448 genes were considered for SNP genotyping. The genes were divided into 2 categories: "A" and "B." Category "A" genes, which included the nicotinic and dopaminergic receptors, were considered to have a higher prior probability of association, and were guaranteed to be targeted for genotyping. Since the study design allowed for individual genotyping of approximately 4,000 single nucleotide polymorphisms (SNPs), the category "B" genes were too numerous to receive adequate SNP coverage once the "A" genes had been sufficiently covered. Therefore the category "B" genes were prioritized using the results of the pooled genotyping from the companion GWAS study (below and (23)). Genes exhibiting the most evidence for association with nicotine dependence were prioritized for coverage. Some genes are larger than others and therefore may receive more SNPs. These genes may therefore appear more significant due to the increased number of tests performed. Hence, correction for multiple testing was done as follows. For a given candidate gene on the "B" list, if $p_{min}$ is the minimum p-value found in the pooled genotyping of stage I of the GWAS for all the SNPs genotyped in the gene, and N is the number of SNPs tested, then the corrected minimum p-value $p_{corr}$ was computed using the formula $$p_{corr} = 1 - (1 - p_{min})^{\frac{N+1}{2}} \quad (1)$$

Since roughly 50% of the SNPs in any chromosomal region are in high linkage disequilibrium (LD) (37), (N+1)/2 was used as the exponent. The Category "B" genes were then ranked by these corrected minimum p-values and SNPs were selected from the top of the ranked list until the resources were exhausted.

SNP Selection

All SNPs within exons were chosen, regardless of allele frequency, and all SNPs within +/−2 kb of annotated gene promoters where the European American minor allele frequency was at least 4%. Tag SNPs were then chosen for all European American LD bins (38) crossing the exons of the candidate genes, with 2 SNPs for each bin with 3 or more SNPs. SNPs meeting these criteria were chosen first from those selected for individual genotyping in the companion pooled study (below and (23)), and then to cover the physical regions as uniformly as possible if there was choice available for the other SNPs. In addition, specific SNPs were included which have been reported in the literature as being associated with nicotine dependence (8, 9, 18, 34).

Pooled Genotyping

See below and Bierut (23) for a description of the pooled genotyping.

Individual Genotyping

For individual genotyping, custom high-density oligonucleotide arrays were designed to interrogate SNPs selected from candidate genes, as well quality control SNPs. Each SNP was interrogated by twenty-four 25mer oligonucleotide probes synthesized on a glass substrate. The twenty-four features comprise 4 sets of 6 features interrogating the neighborhoods of SNP reference and alternate alleles on forward and reference strands. Each allele and strand is represented by five offsets: −2, −1, 0, 1, and 2 indicating the position of the SNP within the 25-mer, with zero being at the thirteenth base. At offset 0 a quartet was tiled, which includes the perfect match to reference and alternate SNP alleles and the two remaining nucleotides as mismatch probes. When possible, the mismatch features were selected as purine nucleotide substitution for purine perfect match nucleotide and a pyrimidine nucleotide substitution for a pyrimidine perfect match nucleotide. Thus, each strand and allele tiling consisted of 6 features comprising five perfect match probes and one mismatch.

Individual Genotype Cleaning

Individual genotypes were cleaned using a supervised prediction algorithm for the genotyping quality, compiled from 15 input metrics that describe the quality of the SNP and the genotype. The genotyping quality metric correlates with a probability of having a discordant call between the Perlegen platform and outside genotyping platforms (i.e., non-Perlegen HapMap project genotypes). A system of 10 bootstrap aggregated regression trees was trained using an independent data set of concordance data between Perlegen genotypes and HapMap project genotypes. The trained predictor was then used to predict the genotyping quality for each of the genotypes in this data set (see below for more information regarding cleaning).

Population Stratification Analysis

In order to avoid false positives due to population stratification, an analysis was performed using the STRUCTURE software (39). This program identifies subpopulations of individuals who are genetically similar through a Markov chain Monte Carlo sampling procedure using markers selected across the genome. Genotype data for 289 high performance SNPs were analyzed across all 1,929 samples. This analysis revealed no evidence for population admixture.

Genetic Association Analysis

An ANOVA analysis testing the predictive power of various phenotypes indicated that gender and site (U.S.A. or Australian) were the most informative, and that age and other demographic variables did not account for significant additional trait variance (Table 11). The primary method of analysis was based on a logistic regression: if p is the probability of being a case, then the linear logistic model has the form $$\log\left(\frac{p}{1-p}\right) = \alpha + \beta_1 g + \beta_2 s + \beta_3 G + \beta_4 gG \quad (2)$$

where $\alpha$ is the intercept, g is gender coded 0 or 1 for males or females, respectively, and s is site coded as 0 or 1 for U.S.A. or Australian, respectively. The variable G represents genotype and is coded as the number of copies of the risk allele, defined as the allele more common in cases than in controls. It follows from equation (2) that the risk due to genotype is being modeled using a log-linear (i.e., multiplicative) scale rather than an additive scale. Maximum likelihood estimates for the coefficients and confidence intervals for odds ratios were computed using the SAS software package (40).

The predictors of the base model were gender and site. Whether the addition of genotype and gender by genotype interaction to the base model significantly increased the predictive power was then tested, and used the resulting 2 degree of freedom chi-squared statistic to rank the SNPs by the corresponding p-values. Table 12 shows the formulas for the odds ratios in terms of the coefficients.

Following these primary analyses, the top ranked SNPs were further analyzed for significant evidence of dominant or recessive modes of inheritance. This was done using a logistic regression of the form $$\log\left(\frac{p}{1-p}\right) = \alpha + \beta_1 g + \beta_2 s + \beta_3 G + \beta_4 H \quad (3)$$

where H is 1 for heterozygotes and 0 otherwise. When H is significant the interpretation is that the genetic effect deviates significantly from the log-linear model. Odds ratios for dominant and recessive models are then computed as described in Table 13.

Linkage Disequilibrium

An estimated $r^2$ correlation was done separately in cases and controls for all pairs of SNPs within 1 Mb windows using an EM algorithm as implemented in the computer program Haploview (version 3.2, found on the internet at the website for the Broad Institute at the Massachusetts Institute of Technology)(41). The final measure of LD is the minimum $r^2$ from the two samples. Following the algorithm in Hinds et al. (38) and Carlson et al. (42), SNPs were grouped into bins where every bin contains at least one "tag SNP" satisfying min($r^2$) ≥0.8 with every SNP in the bin. The group of association signals from such an LD bin can be viewed essentially as a single signal.

Correcting for Multiple Testing

To account for multiple testing the False Discovery Rate (FDR) was estimated (24, 25) to control the proportion of false positives among the reported signals. Since Category "A" genes were considered to have a higher prior probability of association, the recommendations of Roeder et al. (43) were followed and Category "A" gene SNPs were weighted a moderate 10-fold more heavily. Therefore, the Category "B" genes must have stronger association signals for inclusion in the list of FDR-filtered top signals. For each p-value p, a weighted p-value Pw was computed using the formula $$p_w = \begin{cases} wp & \text{Category ``A'' genes} \\ 10wp & \text{Category ``B'' genes} \end{cases}$$

where w was defined so that the average of the weights is 1 (this depends on the number of SNPs selected for "A" and "B" genes). For every weighted p-value $p_{w0}$ a q-value $q_{w0}$ was computed that has the property that the FDR is no greater than $q_{w0}$ among all SNPs with $q_w < q_{w0}$ (25, 44). This was done using the computer program QVALUE (version 1.1, on the internet at the website for Washington University) (45). The estimates of the FDR are based on the q-values.

This method of estimating the FDR does not take into account LD. Therefore, as an additional measure to correct for multiple testing and assess statistical significance, the FDR was estimated using permutations and p-values weighted for "A" and "B" genes, which preserves the LD structure. This was done by performing 1,000 random permutations of the case-control status and testing the permuted data for association. The significance of a p-value from the original data was assessed by counting the number of times a more significant weighted p-value occurs in the random permutations, where the weights were the same as those used for the FDR estimates.

Supplementary Materials for Example 3
DNA Preparation

DNA was extracted from whole blood and EBV transformed cell lines on an AutoPure LS automated DNA extractor using the PuraGene Reagent System (GENTRA Systems). RNase was added to the WBC lysis stage with isopropanol precipitation of the DNA and resuspension in 1×TE Buffer (pH 8.0). DNA was quantified by optical density (OD) at 260 nm on a DU-640 spectrophotometer (Beckman) and OD 260/280 absorbance ratios were between 1.8-2.0. DNA was aliquoted and stored frozen at −80° C. until distributed to the genotyping labs.

Individual Genotype Cleaning

Concordance is computed independently for both reference and alternate allele feature sets, then a maximum is taken of the two values. For each allele at each offset for both the forward and reverse strand feature sets the identity of the brightest feature is noted. The concordance for a particular allele is computed as a ratio of the number of times the perfect match feature is the brightest to the total number of offsets over the forward and reverse strands. In the 24 feature SNP tiling each allele is represented by 6 features, distributed along 5 offsets and forward and reverse strands, with five perfect match probes and one mismatch. If $N_{PM}^X$ is the number of times for allele X when the perfect match feature was brighter than the mismatch feature over all offsets and both strands, then:

$$concordance = \max\left(\frac{N_{PM}^{Ref}}{10}, \frac{N_{PM}^{Alt}}{10}\right)$$

SNP feature sets with concordance <0.9 were discarded from further evaluation.

Let $I^{TM}$ be the trimmed mean of perfect match intensities for a given allele and strand denoted by the subscript. The trimmed mean disregards the highest and the lowest intensity from the 5 perfect match intensities in the 24-feature tilings before computing the arithmetic mean. Let $I^M$ be the mean of the mismatch intensity; since there is only one mismatch for each allele and strand no trimming is performed. Signal to background ratio (signal/background) is then defined to be the ratio between the amplitude of signal, computed from trimmed means of perfect match feature intensities, and amplitude of background, computed from means of mismatch feature intensities. The signal and background are computed as follows:

$$signal = \sqrt{\frac{((I_{PM,Ref,Fwd}^{TM} + I_{PM,Ref,Rev}^{TM})/2)^2 +}{((I_{PM,Alt,Fwd}^{TM} + I_{PM,Alt,Rev}^{TM})/2)^2}}$$

$$background = \sqrt{\frac{((I_{MM,Ref,Fwd}^{M} + I_{MM,Ref,Rev}^{M})/2)^2 +}{((I_{MM,Alt,Fwd}^{M} + I_{MM,Alt,Rev}^{M})/2)^2}}$$

SNP feature sets with signal/background <1.5 were discarded from further evaluations. The number of saturated features was computed as the number of features that reached the highest intensity possible for the digitized numeric intensity value. SNPs with a nonzero number of saturated features were discarded from further evaluations.

As a final test, SNPs were tested for Hardy-Weinberg equilibrium (HWE). Those SNPs with an exact HWE p-value of less than $10^{-15}$ in either the cases or controls were discarded. SNPs with a HWE p-value between $10^{-15}$ and $10^{-4}$ were visually inspected and were discarded when problems with clustering were detected.

Table 14 shows Gender-specific odds ratios and 95% confidence intervals for SNPs in Table 6. The odds ratios are based on the coefficient of the genotype term G in equation (2) and represent the increase in risk for every unit increase in G; i.e., the risk follows a log-linear model (see Table 12).

TABLE 14

| SNP | Gene | Primary p-value | Rank | Gender* Genotype p-value | Male OR | Female OR |
|---|---|---|---|---|---|---|
| rs6474413 | CHRNB3 | 9.36E−05 | 1 | 1.12E−01 | 1.2 (0.9-1.5) | 1.5 (1.3-1.9) |
| rs10958726 | CHRNB3 | 1.33E−04 | 2 | 1.04E−01 | 1.2 (0.9-1.5) | 1.5 (1.2-1.9) |
| rs578776 | CHRNA3 | 3.08E−04 | 3 | 4.12E−01 | 1.5 (1.2-1.9) | 1.3 (1.1-1.6) |
| rs6517442 | KCNJ6 | 5.62E−04 | 4 | 6.17E−01 | 1.4 (1.1-1.7) | 1.3 (1.1-1.5) |
| rs16969968 | CHRNA5 | 6.42E−04 | 5 | 8.13E−01 | 1.3 (1.1-1.7) | 1.3 (1.1-1.5) |
| rs3762611 | GABRA4 | 9.22E−04 | 6 | 7.50E−02 | 2.1 (1.4-3.2) | 1.3 (0.9-1.8) |
| rs1051730 | CHRNA3 | 9.93E−04 | 7 | 1.00E+00 | 1.3 (1.0-1.6) | 1.3 (1.1-1.5) |
| rs10508649 | PIP5K2A | 1.02E−03 | 8 | 1.09E−02 | 9.7 (2.1-44.2) | 1.0 (0.3-3.1) |
| rs17041074 | DAO | 1.12E−03 | 9 | 3.70E−01 | 0.8 (0.6-1.0) | 1.3 (1.1-1.6) |
| rs3762607 | GABRA4 | 1.22E−03 | 10 | 3.43E−02 | 2.2 (1.4-3.3) | 1.2 (0.9-1.6) |
| rs2767 | CHRND | 1.50E−03 | 11 | 1.08E−01 | 1.5 (1.2-1.8) | 1.1 (1.0-1.4) |
| rs6772197 | DOCK3 (GRM2) | 1.66E−03 | 12 | 6.35E−04 | 1.6 (1.2-2.2) | 0.9 (0.7-1.1) |
| rs3021529 | AVPR1A | 1.73E−03 | 13 | 8.96E−01 | 0.8 (0.5-1.0) | 1.5 (1.1-1.9) |
| rs1206549 | CLTCL1 | 1.75E−03 | 14 | 9.11E−01 | 1.4 (1.1-1.9) | 1.4 (1.1-1.7) |
| rs637137 | CHRNA5 | 2.82E−03 | 22 | 3.18E−01 | 1.5 (1.1-1.9) | 1.2 (1.0-1.5) |
| rs3791729 | CHRND | 3.39E−03 | 25 | 3.10E−01 | 1.4 (1.1-1.7) | 1.2 (1.0-1.4) |
| rs4531 | DBH | 5.10E−03 | 30 | 9.11E−01 | 1.5 (1.0-2.1) | 1.5 (1.1-2.0) |
| rs3025382 | DBH | 5.14E−03 | 31 | 1.82E−01 | 1.6 (1.2-2.3) | 1.2 (0.9-1.6) |
| rs7877 | FMO1 | 6.33E−03 | 38 | 8.81E−01 | 1.3 (1.0-1.6) | 1.3 (1.1-1.6) |
| rs6320 | HTR5A | 6.50E−03 | 39 | 1.61E−03 | 0.7 (0.6-1.0) | 1.2 (1.0-1.5) |
| rs4802100 | CYP2B6 | 6.76E−03 | 41 | 2.82E−01 | 0.9 (0.6-1.4) | 1.6 (1.2-2.1) |
| rs2304297 | CHRNA6 | 6.91E−03 | 42 | 1.59E−01 | 1.1 (0.8-1.4) | 1.4 (1.1-1.7) |
| rs3760657 | CYP2B6 | 6.98E−03 | 43 | 3.38E−02 | 0.9 (0.7-1.4) | 1.6 (1.2-2.1) |
| rs2276560 | CHRNG | 7.42E−03 | 44 | 8.58E−02 | 1.5 (1.1-1.9) | 1.1 (0.9-1.3) |
| rs742350 | FMO1 | 8.45E−03 | 48 | 2.67E−01 | 1.2 (0.9-1.6) | 1.5 (1.1-1.9) |
| rs684513 | CHRNA5 | 8.72E−03 | 49 | 1.72E−01 | 1.5 (1.1-1.9) | 1.2 (0.9-1.4) |
| rs510769 | OPRM1 | 9.84E−03 | 58 | 1.38E−01 | 1.1 (0.8-1.4) | 1.3 (1.1-1.6) |
| rs4245150 | DRD2 | 1.08E−02 | 61 | 2.79E−03 | 0.8 (0.6-1.0) | 1.2 (1.0-1.4) |
| rs3743078 | CHRNA3 | 1.10E−02 | 63 | 1.54E−01 | 1.5 (1.1-2.0) | 1.2 (0.9-1.4) |
| rs1657273 | HTR5A | 1.11E−02 | 64 | 3.06E−03 | 0.8 (0.6-1.0) | 1.2 (1.0-1.5) |
| rs17602038 | DRD2 | 1.17E−02 | 69 | 3.13E−03 | 0.8 (0.6-1.0) | 1.2 (1.0-1.4) |
| rs3813567 | CHRNB4 | 1.18E−02 | 70 | 9.10E−02 | 1.5 (1.1-2.0) | 1.1 (0.9-1.4) |
| rs893109 | HTR5A | 1.24E−02 | 73 | 3.46E−03 | 0.8 (0.6-1.0) | 1.2 (1.0-1.5) |
| rs16864387 | FMO4 | 1.28E−02 | 74 | 3.82E−01 | 1.2 (0.9-1.7) | 1.4 (1.1-1.9) |
| rs6045733 | PDYN | 1.55E−02 | 84 | 4.25E−03 | 1.3 (1.1-1.7) | 0.9 (0.7-1.0) |
| rs4953 | CHRNB3 | 1.61E−02 | 85 | 1.00E+00 | 1.6 (0.9-2.8) | 1.7 (1.1-2.5) |
| rs4952 | CHRNB3 | 1.63E−02 | 87 | 1.00E+00 | 1.6 (0.9-2.8) | 1.7 (1.1-2.5) |
| rs6749955 | CHRNG | 1.70E−02 | 91 | 1.67E−01 | 1.4 (1.1-1.8) | 1.1 (0.9-1.4) |
| rs7517376 | FMO1 | 1.80E−02 | 95 | 3.78E−01 | 1.2 (0.9-1.6) | 1.4 (1.1-1.8) |

Table 15 shows top associations with nicotine dependence showing results from the primary analysis side by side with results based on the U.S. sample only. The conventions are the same as for Table 6.

TABLE 15

| SNP | Gene | Function | Cat[a] | Risk Allele | US-only Risk Allele | Primary p-value | US-only p-value | Primary Rank | US-only Rank | Primary FDR | US-only FDR |
|---|---|---|---|---|---|---|---|---|---|---|---|
| rs6474413 | CHRNB3 | FP | A | T (0.81/0.76) | T (0.81/0.76) | 9.36E−05 | 3.23E−03 | 1 | 19 | 0.056 | 0.228 |
| rs10958726 | CHRNB3 | LD BIN | A | T (0.81/0.76) | T (0.81/0.77) | 1.33E−04 | 4.69E−03 | 2 | 27 | 0.056 | 0.228 |
| rs578776 | CHRNA3 | UTR | A | G (0.78/0.72) | G (0.78/0.71) | 3.08E−04 | 8.48E−05 | 3 | 1 | 0.086 | 0.071 |
| rs6517442 | KCNJ6 | FP | B | C (0.34/0.28) | C (0.35/0.28) | 5.62E−04 | 6.93E−04 | 4 | 5 | 0.344 | 0.228 |
| rs16969968 | CHRNA5 | NONSYN | A | A (0.38/0.32) | A (0.38/0.32) | 6.42E−04 | 7.32E−04 | 5 | 7 | 0.134 | 0.176 |
| rs3762611 | GABRA4 | FP | B | G (0.93/0.91) | G (0.94/0.91) | 9.22E−04 | 5.29E−03 | 6 | 31 | 0.344 | 0.533 |
| rs1051730 | CHRNA3 | SYNON | A | A (0.38/0.32) | A (0.38/0.32) | 9.93E−04 | 8.41E−04 | 7 | 10 | 0.166 | 0.176 |
| rs10508649 | PIP5K2A | SYNON | B | T (1.00/0.99) | T (1.00/0.99) | 1.02E−03 | 3.44E−04 | 8 | 2 | 0.344 | 0.228 |
| rs17041074 | DAO | INTRON | B | A (0.27/0.26) | A (0.27/0.27) | 1.12E−03 | 1.90E−03 | 9 | 13 | 0.344 | 0.349 |
| rs3762607 | GABRA4 | FP | B | A (0.93/0.91) | A (0.94/0.91) | 1.22E−03 | 6.16E−03 | 10 | 40 | 0.344 | 0.565 |
| rs2767 | CHRND | UTR | A | G (0.39/0.34) | G (0.39/0.34) | 1.50E−03 | 4.87E−03 | 11 | 28 | 0.209 | 0.228 |
| rs6772197 | (GRM2) | INTRON | B | A (0.84/0.81) | A (0.85/0.82) | 1.66E−03 | 7.39E−03 | 12 | 47 | 0.384 | 0.599 |
| rs3021529 | AVPR1A | UTR | B | G (0.86/0.85) | G (0.87/0.86) | 1.73E−03 | 5.96E−02 | 13 | 298 | 0.384 | 0.867 |
| rs1206549 | CLTCL1 | INTRON | B | G (0.86/0.82) | G (0.87/0.82) | 1.75E−03 | 4.35E−04 | 14 | 3 | 0.384 | 0.228 |
| rs637137 | CHRNA5 | INTRON | A | T (0.81/0.76) | T (0.80/0.75) | 2.82E−03 | 2.80E−03 | 22 | 16 | 0.336 | 0.228 |
| rs3791729 | CHRND | INTRON | A | A (0.36/0.32) | A (0.37/0.32) | 3.39E−03 | 1.70E−02 | 25 | 113 | 0.344 | 0.325 |
| rs4531 | DBH | NONSYN | A | G (0.93/0.91) | G (0.93/0.91) | 5.10E−03 | 2.34E−02 | 30 | 143 | 0.344 | 0.383 |
| rs3025382 | DBH | INTRON | A | G (0.9/0.88) | G (0.92/0.88) | 5.14E−03 | 8.17E−04 | 31 | 9 | 0.344 | 0.176 |
| rs7877 | FMO1 | UTR | A | C (0.74/0.70) | C (0.74/0.70) | 6.33E−03 | 8.46E−03 | 38 | 59 | 0.344 | 0.228 |
| rs6320 | HTR5A | SYNON | A | T (0.72/0.71) | T (0.72/0.71) | 6.50E−03 | 6.04E−03 | 39 | 38 | 0.344 | 0.228 |
| rs4802100 | CYP2A7P1 | FP | A | G (0.10/0.08) | G (0.10/0.09) | 6.76E−03 | 5.28E−02 | 41 | 263 | 0.344 | 0.533 |
| rs2304297 | CHRNA6 | UTR | A | G (0.79/0.75) | G (0.79/0.75) | 6.91E−03 | 1.38E−02 | 42 | 95 | 0.344 | 0.295 |

TABLE 15-continued

| SNP | Gene | Function | Cat[a] | Risk Allele | US-only Risk Allele | Primary p-value | US-only p-value | Primary Rank | US-only Rank | Primary FDR | US-only FDR |
|---|---|---|---|---|---|---|---|---|---|---|---|
| rs3760657 | CYP2A7P1 | FP | A | G (0.10/0.08) | G (0.10/0.09) | 6.98E−03 | 5.50E−02 | 43 | 277 | 0.344 | 0.540 |
| rs2276560 | CHRNG | LD BIN | A | T (0.77/0.74) | T (0.77/0.74) | 7.42E−03 | 1.04E−02 | 44 | 72 | 0.344 | 0.256 |
| rs742350 | FMO1 | SYNON | A | C (0.87/0.84) | C (0.87/0.84) | 8.45E−03 | 5.51E−03 | 48 | 33 | 0.344 | 0.228 |
| rs684513 | CHRNA5 | INTRON | A | C (0.82/0.78) | C (0.81/0.77) | 8.72E−03 | 8.15E−03 | 49 | 54 | 0.344 | 0.228 |
| rs510769 | OPRM1 | INTRON | A | T (0.27/0.24) | T (0.27/0.24) | 9.84E−03 | 2.84E−02 | 58 | 167 | 0.344 | 0.410 |
| rs4245150 | DRD2 | LD BIN | A | G (0.37/0.36) | G (0.37/0.36) | 1.08E−02 | 1.29E−02 | 61 | 87 | 0.344 | 0.284 |
| rs3743078 | CHRNA3 | INTRON | A | G (0.83/0.79) | G (0.82/0.79) | 1.10E−02 | 1.98E−02 | 63 | 128 | 0.344 | 0.349 |
| rs1657273 | HTR5A | LD BIN | A | G (0.69/0.68) | G (0.69/0.68) | 1.11E−02 | 7.74E−03 | 64 | 50 | 0.344 | 0.228 |
| rs17602038 | DRD2 | LD BIN | A | C (0.37/0.36) | C (0.37/0.36) | 1.17E−02 | 1.43E−02 | 69 | 98 | 0.344 | 0.298 |
| rs3813567 | CHRNB4 | FP | A | A (0.83/0.79) | A (0.83/0.79) | 1.18E−02 | 1.18E−02 | 70 | 81 | 0.344 | 0.274 |
| rs893109 | HTR5A | LD BIN | A | G (0.69/0.68) | G (0.69/0.68) | 1.24E−02 | 7.84E−03 | 73 | 52 | 0.344 | 0.228 |
| rs16864387 | FMO4 | UTR | A | T (0.87/0.84) | T (0.88/0.84) | 1.28E−02 | 7.58E−03 | 74 | 48 | 0.344 | 0.228 |
| rs6045733 | PDYN | LD BIN | A | G (0.66/0.65) | G (0.66/0.65) | 1.55E−02 | 1.56E−02 | 84 | 108 | 0.384 | 0.318 |
| rs4953 | CHRNB3 | SYNON | A | G (0.97/0.95) | G (0.97/0.95) | 1.61E−02 | 2.67E−02 | 85 | 160 | 0.384 | 0.410 |
| rs4952 | CHRNB3 | SYNON | A | C (0.97/0.95) | C (0.97/0.95) | 1.63E−02 | 2.71E−02 | 87 | 163 | 0.384 | 0.410 |
| rs6749955 | CHRNG | LD BIN | A | T (0.77/0.73) | T (0.77/0.73) | 1.70E−02 | 2.09E−02 | 91 | 135 | 0.384 | 0.349 |
| rs7517376 | FMO1 | SYNON | A | A (0.87/0.84) | A (0.88/0.84) | 1.80E−02 | 7.74E−03 | 95 | 51 | 0.384 | 0.228 |

[a]Category

Table 16 shows top associations with nicotine dependence based on the U.S. sample only. The p-value for the U.S. sample uses the same logistic regression model as for the primary analysis with the "site" term omitted. Only results where the weighted FDR in the U.S. sample is less than 40% are shown. LD estimates used for bins are from the U.S. sample. The conventions are the same as for Table 6.

| SNP | Gene | Function | Cat[a] | LD Bin ID | Min r² | U.S.-only Risk Allele | U.S.-only p-value | Primary p-value | U.S.-only Rank | Primary Rank | U.S.-only FDR | Primary FDR |
|---|---|---|---|---|---|---|---|---|---|---|---|---|
| rs578776 | CHRNA3 | UTR | A | — | — | G (0.78/0.71) | 8.48E−05 | 3.08E−04 | 1 | 3 | 0.071 | 0.086 |
| rs10508649 | PIP5K2A | SYNON | B | — | — | T (1.00/0.99) | 3.44E−04 | 1.02E−03 | 2 | 8 | 0.228 | 0.344 |
| rs1206549 | CLTCL1 | INTRON | B | 22-5 | 0.994 | G (0.87/0.82) | 4.35E−04 | 1.75E−03 | 3 | 14 | 0.228 | 0.384 |
| rs807429 | CLTCL1 | INTRON | B | 22-5 | 0.994 | A (0.87/0.82) | 4.89E−04 | 1.93E−03 | 4 | 15 | 0.228 | 0.402 |
| rs6517442 | KCNJ6 | FP | B | — | — | C (0.35/0.28) | 6.93E−04 | 5.62E−04 | 5 | 4 | 0.228 | 0.344 |
| rs2180529 | SNX5 | LD BIN | B | 20-6 | 0.920 | T (0.30/0.27) | 7.28E−04 | 4.87E−03 | 6 | 28 | 0.228 | 0.505 |
| rs16969968 | CHRNA5 | NONSYN | A | 15-12 | 0.989 | A (0.38/0.32) | 7.32E−04 | 6.42E−04 | 7 | 5 | 0.176 | 0.134 |
| rs10246819 | CHRM2 | LD BIN | B | 7-49 | 0.867 | C (0.56/0.54) | 7.99E−04 | 3.33E−03 | 8 | 24 | 0.228 | 0.471 |
| rs3025382 | DBH | INTRON | A | — | — | G (0.92/0.88) | 8.17E−04 | 5.14E−03 | 9 | 31 | 0.176 | 0.344 |
| rs1051730 | CHRNA3 | SYNON | A | 15-12 | 0.989 | A (0.38/0.32) | 8.41E−04 | 9.93E−04 | 10 | 7 | 0.176 | 0.166 |
| rs1061418 | GABRE | UTR | B | — | — | A (0.14/0.12) | 8.43E−04 | 6.15E−03 | 11 | 36 | 0.228 | 0.570 |
| rs1378650 | CHRM2 | LD BIN | B | — | — | G (0.56/0.51) | 1.67E−03 | 1.78E−02 | 12 | 93 | 0.325 | 0.744 |
| rs17041074 | DAO | INTRON | B | — | — | A (0.27/0.27) | 1.90E−03 | 1.12E−03 | 13 | 9 | 0.349 | 0.344 |
| rs17636651 | CAMK2D | FP | B | — | — | G (0.95/0.93) | 2.02E−03 | 1.39E−02 | 14 | 79 | 0.349 | 0.693 |
| rs3803431 | ALDH1A3 | SYNON | B | — | — | C (0.97/0.95) | 2.51E−03 | 2.78E−02 | 15 | 137 | 0.398 | 0.783 |
| rs637137 | CHRNA5 | INTRON | A | 15-3 | 0.805 | T (0.80/0.75) | 2.80E−03 | 2.82E−03 | 16 | 22 | 0.228 | 0.336 |
| rs16143 | NPY | UTR | A | 7-1 | 0.803 | T (0.28/0.26) | 3.21E−03 | 2.49E−02 | 18 | 126 | 0.228 | 0.446 |
| rs6474413 | CHRNB3 | FP | A | 8-21 | 0.988 | T (0.81/0.76) | 3.23E−03 | 9.36E−05 | 19 | 1 | 0.228 | 0.056 |
| rs16142 | NPY | UTR | A | 7-1 | 0.803 | G (0.28/0.26) | 4.46E−03 | 3.31E−02 | 26 | 173 | 0.228 | 0.471 |
| rs10958726 | CHRNB3 | LD BIN | A | 8-21 | 0.988 | T (0.81/0.77) | 4.69E−03 | 1.33E−04 | 27 | 2 | 0.228 | 0.056 |
| rs2767 | CHRND | UTR | A | 2-68 | 0.877 | G (0.39/0.34) | 4.87E−03 | 1.50E−03 | 28 | 11 | 0.228 | 0.209 |
| rs16478 | NPY | UTR | A | 7-1 | 0.803 | A (0.28/0.26) | 5.31E−03 | 3.80E−02 | 32 | 194 | 0.228 | 0.495 |
| rs742350 | FMO1 | SYNON | A | 1-7 | 0.974 | C (0.87/0.84) | 5.51E−03 | 8.45E−03 | 33 | 48 | 0.228 | 0.344 |
| rs2302761 | CHRNB1 | INTRON | A | 17-8 | 0.933 | C (0.83/0.78) | 5.64E−03 | 4.61E−02 | 34 | 238 | 0.228 | 0.504 |
| rs7210231 | CHRNB1 | INTRON | A | 17-8 | 0.933 | C (0.82/0.77) | 5.74E−03 | 4.18E−02 | 35 | 218 | 0.228 | 0.498 |
| rs6320 | HTR5A | SYNON | A | — | — | T (0.72/0.71) | 6.04E−03 | 6.50E−03 | 38 | 39 | 0.228 | 0.344 |
| rs16149 | NPY | FP | A | 7-1 | 0.803 | A (0.28/0.26) | 6.12E−03 | 3.51E−02 | 39 | 183 | 0.228 | 0.480 |
| rs16138 | NPY | INTRON | A | — | — | C (0.28/0.26) | 6.19E−03 | 4.42E−02 | 41 | 227 | 0.228 | 0.504 |
| rs2236196 | CHRNA4 | UTR | A | — | — | G (0.28/0.23) | 6.68E−03 | 2.63E−02 | 42 | 132 | 0.228 | 0.446 |
| rs16864387 | FMO4 | UTR | A | 1-7 | 0.974 | T (0.88/0.84) | 7.58E−03 | 1.28E−02 | 48 | 74 | 0.228 | 0.344 |

-continued

| SNP | Gene | Function | Cat[a] | LD Bin ID | Min r[2] | U.S.-only Risk Allele | U.S.-only p-value | Primary p-value | U.S.-only Rank | Primary Rank | U.S.-only FDR | Primary FDR |
|---|---|---|---|---|---|---|---|---|---|---|---|---|
| rs1657273 | HTR5A | LD BIN | A | 7-29 | 0.974 | G (0.69/0.68) | 7.74E−03 | 1.11E−02 | 50 | 64 | 0.228 | 0.344 |
| rs7517376 | FMO1 | SYNON | A | 1-7 | 0.974 | A (0.88/0.84) | 7.74E−03 | 1.80E−02 | 51 | 95 | 0.228 | 0.384 |
| rs893109 | HTR5A | LD BIN | A | 7-29 | 0.974 | G (0.69/0.68) | 7.84E−03 | 1.24E−02 | 52 | 73 | 0.228 | 0.344 |
| rs684513 | CHRNA5 | INTRON | A | 15-3 | 0.805 | C (0.81/0.77) | 8.15E−03 | 8.72E−03 | 54 | 49 | 0.228 | 0.344 |
| rs7877 | FMO1 | UTR | A | 1-62 | 0.887 | C (0.74/0.70) | 8.46E−03 | 6.33E−03 | 59 | 38 | 0.228 | 0.344 |
| rs740602 | COMT | SYNON | A |  | — | G (1.00/0.99) | 9.53E−03 | 3.43E−02 | 62 | 180 | 0.249 | 0.477 |
| rs16159 | NPY | LD BIN | A | 7-1 | 0.803 | T (0.31/0.29) | 9.83E−03 | 7.43E−02 | 63 | 373 | 0.249 | 0.614 |
| rs2276560 | CHRNG | LD BIN | A | 2-63 | 0.931 | T (0.77/0.74) | 1.04E−02 | 7.42E−03 | 72 | 44 | 0.256 | 0.344 |
| rs7215056 | CHRNB1 | INTRON | A | 17-8 | 0.933 | C (0.82/0.78) | 1.07E−02 | 6.09E−02 | 73 | 295 | 0.256 | 0.570 |
| rs3813567 | CHRNB4 | FP | A |  | — | A (0.83/0.79) | 1.18E−02 | 1.18E−02 | 81 | 70 | 0.274 | 0.344 |
| rs17149039 | NPY | LD BIN | A | 7-1 | 0.803 | G (0.33/0.31) | 1.27E−02 | 8.45E−02 | 85 | 428 | 0.284 | 0.632 |
| rs4245150 | DRD2 | LD BIN | A | 11-8 | 0.997 | G (0.37/0.36) | 1.29E−02 | 1.08E−02 | 87 | 61 | 0.284 | 0.344 |
| rs2304297 | CHRNA6 | UTR | A | 8-52 | 0.830 | G (0.79/0.75) | 1.38E−02 | 6.91E−03 | 95 | 42 | 0.295 | 0.344 |
| rs17602038 | DRD2 | LD BIN | A | 11-8 | 0.997 | G (0.37/0.36) | 1.43E−02 | 1.17E−02 | 98 | 69 | 0.298 | 0.344 |
| rs6045733 | PDYN | LD BIN | A | 20-34 | 0.803 | G (0.66/0.65) | 1.56E−02 | 1.55E−02 | 108 | 84 | 0.318 | 0.384 |
| rs3791729 | CHRND | INTRON | A | 2-68 | 0.877 | A (0.37/0.32) | 1.70E−02 | 3.39E−03 | 113 | 25 | 0.325 | 0.344 |
| rs12056414 | OPRK1 | INTRON | A | 8-14 | 1.000 | A (0.09/0.07) | 1.71E−02 | 3.71E−02 | 116 | 191 | 0.325 | 0.492 |
| rs3743078 | CHRNA3 | INTRON | A | 15-3 | 0.805 | G (0.82/0.79) | 1.98E−02 | 1.10E−02 | 128 | 63 | 0.349 | 0.344 |
| rs16148 | NPY | FP | A | 7-1 | 0.803 | C (0.35/0.33) | 2.01E−02 | 1.14E−01 | 130 | 556 | 0.349 | 0.676 |
| rs6045819 | PDYN | SYNON | A | 20-29 | 0.859 | A (0.90/0.88) | 2.05E−02 | 2.98E−02 | 133 | 159 | 0.349 | 0.470 |
| rs6749955 | CHRNG | LD BIN | A | 2-63 | 0.931 | T (0.77/0.73) | 2.09E−02 | 1.70E−02 | 135 | 91 | 0.349 | 0.384 |
| rs4531 | DBH | NONSYN | A |  | — | G (0.93/0.91) | 2.34E−02 | 5.10E−03 | 143 | 30 | 0.383 | 0.344 |
| rs12056411 | OPRK1 | INTRON | A | 8-14 | 1.000 | A (0.09/0.07) | 2.53E−02 | 5.21E−02 | 154 | 263 | 0.398 | 0.522 |

[a]Category

Table 9. Gender-specific odds ratios and 95% confidence intervals for SNPs in Table 6. Only SNPs where the gender by genotype interaction was significant (p<0.05) are shown, and the SNP with the most significant primary p-value was selected from each LD bin. The odds ratios are based on the coefficient of the genotype term G in equation (2) and represents the increase in risk for every unit increase in G; i.e., the risk follows a log-linear model (see Tables 12 and 13).

TABLE 9

| SNP | Gene | Primary p-value | Rank | Gender* Genotype p-value | Male Odds Ratio | Female Odds Ratio |
|---|---|---|---|---|---|---|
| rs10508649 | PIP5K2A | 1.02E−03 | 8 | 1.09E−02 | 9.7 (2.1-44.2) | 1.0 (0.3-3.1) |
| rs17041074 | DAO | 1.12E−03 | 9 | 3.70E−04 | 0.8 (0.6-1.0) | 1.3 (1.1-1.6) |
| rs3762607 | GABRA4 | 1.22E−03 | 10 | 3.43E−02 | 2.2 (1.4-3.3) | 1.2 (0.9-1.6) |
| rs6772197 | DOCK3 (GRM2) | 1.66E−03 | 12 | 6.35E−04 | 1.6 (1.2-2.2) | 0.9 (0.7-1.1) |
| rs3021529 | AVPR1A | 1.73E−03 | 13 | 8.96E−04 | 0.8 (0.5-1.0) | 1.5 (1.1-1.9) |
| rs6320 | HTR5A | 6.50E−03 | 39 | 1.61E−03 | 0.7 (0.6-1.0) | 1.2 (1.0-1.5) |
| rs4802100 | CYP2A7P1 | 6.76E−03 | 41 | 2.82E−02 | 0.9 (0.6-1.4) | 1.6 (1.2-2.1) |
| rs4245150 | DRD2 | 1.08E−02 | 61 | 2.79E−03 | 0.8 (0.6-1.0) | 1.2 (1.0-1.4) |
| rs1657273 | HTR5A | 1.11E−02 | 64 | 3.06E−03 | 0.8 (0.6-1.0) | 1.2 (1.0-1.5) |
| rs6045733 | PDYN | 1.55E−02 | 84 | 4.25E−03 | 1.3 (1.1-1.7) | 0.9 (0.7-1.0) |

Table 10. A summary of covariates and FTND scores in the sample. By definition, all control subjects scored 0 on the Fagerström test for nicotine dependence (FTND) (34).

TABLE 10

|  |  | Cases | | Controls | |
|---|---|---|---|---|---|
|  |  | U.S.A. | Australia | U.S.A. | Australia |
| Males | N | 351 | 114 | 251 | 17 |
|  | Age range | 25-44 | 30-82 | 25-44 | 34-82 |
|  | μ ± σ[a] | 36.8 ± 5.3 | 39.4 ± 9.8 | 35.3 ± 5.5 | 55.1 ± 15.4 |
|  | FTND range | 4-10 | 4-10 | — | — |
|  | μ ± σ | 6.4 ± 1.7 | 6.1 ± 1.6 | — | — |
| Females | N | 446 | 139 | 562 | 49 |
|  | Age range | 25-45 | 27-79 | 25-44 | 27-78 |
|  | μ ± σ | 37.1 ± 5.2 | 40.4 ± 10.3 | 35.9 ± 5.5 | 46.4 ± 14.0 |
|  | FTND range | 4-10 | 4-10 | — | — |
|  | μ ± σ | 6.4 ± 1.8 | 6.0 ± 1.6 | — | — |
| Combined | N | 797 | 253 | 813 | 66 |
|  | Total | 1,050 | | 879 | |

[a]Mean ± standard deviation.

Table 11. ANOVA analysis of covariates. Logistic regression, modeling the probability of being a case, was performed for the indicated covariates. The $\chi^2$ statistic is from the formula where $\Delta \log L$ is the change in likelihood in the logistic regression. The variable "site" has two levels: U.S.A. and Australia.

TABLE 11

| Model | ANOVA Evaluated Covariate | $\chi^2$ (1df) | p-value |
|---|---|---|---|
| gender | gender | 40.0 | $4.2 \times 10^{-10}$ |
| gender + age | age | 10.3 | $1.3 \times 10^{-03}$ |
| gender + site | site | 100.4 | $1.2 \times 10^{-23}$ |
| gender + site + age | age | 0.25 | 0.62 |
| gender + site + gender * site | gender * site | 0.84 | 0.36 |

Tables 12 and 13. (12) Coding of the gender term g and the genotype term G used in the primary logistic regression model. The allele a is the risk allele, the allele more common in cases than in controls. The variable G is defined as the number of copies of the risk allele, and g is 0 or 1 for male or female, respectively. The last column shows the expression for the gender-specific odds ratio for a given genotype compared to the AA genotype, which follows directly from the logistic regression model in equation (2). (13) Codings used for the secondary logistic regression model. The odds ratios follow directly from equation (3). Note that for a dominant model the two odds ratios are equal, and for a recessive model the odds ratio for aA is 1.

Table 12

TABLE 13

| Genotype | g | G | Odds Ratio |
|---|---|---|---|
| AA | 0 | 0 | — |
| aA | 0 | 1 | |
| aa | 0 | 2 | $e^{2\beta_3}$ |
| AA | 1 | 0 | — |
| aA | 1 | 1 | $e^{\beta_3} e^{\beta_4}$ |
| aa | 1 | 2 | |

| Genotype | G | H | Odds Ratio |
|---|---|---|---|
| AA | 0 | 0 | — |
| aA | 1 | 1 | $e^{\beta_3} e^{\beta_4}$ |
| aa | 2 | 0 | $e^{2\beta_3}$ |

References For Example 3

1. World Health Organization, *World Health Statistics* 2006 (2006) WHO Press, on the internet at www.who.int/whosis (accessed Jun. 20, 2006).
2. Warren, C. W., Jones, N. R., Eriksen, M. P. and Asma, S. (2006) Global Tobacco Surveillance System (GTSS) collaborative group. Patterns of global tobacco use in young people and implications for future chronic disease burden in adults. *Lancet*, 367, 749-753.
3. Tapper, A. R., Nashmi, R. and Lester, H. A. (2006) Neuronal nicotinic acetylcholine receptors and nicotine dependence. In Madras, B. K., Colvis, C. M., Pollock, J. D., Rutter, J. L., Shurtleff, D., von Zastrow, M., (eds.), *Cell Biology of Addiction*. Cold Spring Harbor Laboratory Press, Cold Spring Harbor, N.Y.
4. Laviolette, S. R. and Van de Kooy, D. (2004) The neurobiology of nicotine addiction: Bridging the gap from molecules to behavior. *Nat. Rev. Neurosci.* 5, 55-65.
5. Corrigall, W. A., Coen, K. M. and Adamson, K. L. (1994) Self-administered nicotine activates the mesolimbic dopamine system through the ventral tegmental area. *Brain. Res.*, 653, 278-284.
6. World Health Organization, *The Tobacco Atlas* (2006), Types of Tobacco Use, on the internet at www.who.int/tobacco/resources/publications/tobacco_atlas (accessed Jun. 19, 2006)
7. Lessov, C. N., Martin, N. G., Statham, D. J., Todorov, A. A., Slutske, W. S., Bucholz, K. K., Heath, A. C., Madden, P. A. (2004) Defining nicotine dependence for genetic research: evidence from Australian twins. *Psychol. Med.*, 34, 865-879.
8. Feng, Y., Niu, T., Xing, H., Xu, X., Chen, C., Peng, S., Wang, L., Laird, N. and Xu, X. (2004) A common haplotype of the nicotine acetylcholine receptor alpha 4 subunit gene is associated with vulnerability to nicotine addiction in men. *Am. J. Hum. Genet.*, 75, 112-121.
9. Li, M. D., Beuten, J., Ma, J. Z., Payne, T. J., Lou, X. Y., Garcia, V., Duenes, A. S., Crews, K. M. and Elston, R. C. (2005) Ethnic- and gender-specific association of the nicotinic acetylcholine receptor alpha4 subunit gene (CHRNA4) with nicotine dependence. *Hum. Mol. Genet.*, 14, 1211-1219.
10. Greenbaum, L., Kanyas, K., Karni, O., Merbl, Y., Olender, T., Horowitz, A., Yakir, A., Lancet, D., Ben-Asher, E. and Lerer, B. (2006) Why do young women smoke? I. Direct and interactive effects of environment, psychological characteristics and nicotinic cholinergic receptor genes. *Mol. Psychiatr.*, 11, 312-322.
11. Boustead, C., Taber, H., Idle, J. R. and Cholerton, S. (1997) CYP2D6 genotype and smoking behaviour in cigarette smokers. *Pharmacogenetics*, 7, 411-414.
12. Pianezza, M. L., Sellers, E. M., and Tyndale, R. F. (1998) Nicotine metabolism defect reduces smoking. *Nature*, 393, 750.
13. Cholerton, S., Boustead, C., Taber, H., Arpanahi, A. and Idle, J. R. (1996) CYP2D6 genotypes in cigarette smokers and non-tobacco users. *Pharmacogenetics*, 6, 261-263.
14. Comings, D. E., Ferry, L., Bradshaw-Robinson, S., Burchette, R., Chiu, C. and Muhleman, D. (1996) The dopamine D2 receptor (DRD2) gene: a genetic risk factor in smoking. *Pharmacogenetics* 6, 73-79.
15. Shields, P. G., Lerman, C., Audrain, J., Bowman, E. D., Main, D., Boyd, N. R. and Caporaso, N. E. (1998) Dopamine D4 receptors and the risk of cigarette smoking in African-Americans and Caucasians. *Cancer Epidemiol. Biomarkers Prev.*, 7, 453-458.
16. Lerman, C., Caporaso, N. E., Audrain, J., Main, D., Bowman, E. D., Lockshin, B., Boyd, N. R. and Shields, P. G. (1999) Evidence suggesting the role of specific genetic factors in cigarette smoking. *Health Psychol.*, 18, 14-20.
17. Spitz, M. R., Shi, H., Yang, F., Hudmon, K. S., Jiang, H., Chamberlain, R. M., Amos, C. I., Wan, Y., Cinciripini, P., Hong, W. K. and Wu, X. (1998) Case-control study of the D2 dopamine receptor gene and smoking status in lung cancer patients. *J. Natl. Cancer. Inst.*, 90, 358-363.
18. Beuten, J., Ma, J. Z., Payne, T. J., Dupont, R. T., Crews, K. M., Somes, G., Williams, N. J., Elston, R. C. and Li, M. D. (2005) Single- and multilocus allelic variants within the GABA(B) receptor subunit 2 (GABAB2) gene are significantly associated with nicotine dependence. *Am. J. Hum. Genet.*, 76, 859-864.
19. Hu, S., Brody, C. L., Fisher, C., Gunzerath, L., Nelson, M. L., Sabol, S. Z., Sirota, L. A., Marcus, S. E., Greenberg, B. D., Murphy, D. L. and Hamer, D. H. (2000) Interaction between the serotonin transporter gene and neuroticism in cigarette smoking behavior. *Mol. Psychiatry*, 5, 181-188.
20. Lerman, C., Caporaso, N. E., Audrain, J., Main, D., Boyd, N. R. and Shields, P. G. (2000) Interacting effects of the serotonin transporter gene and neuroticism in smoking practices and nicotine dependence. *Mol. Psychiatry*, 5, 189-192.
21. Beuten, J., Ma, J. Z., Payne, T. J., Dupont, R. T., Quezada, P., Huang, W., Crews, K. M. and Li, M. D. (2005) Significant association of BDNF haplotypes in European-American male smokers but not in European-American female or African-American smokers. *Am. J. Med. Genet. B Neuropsychiatr. Genet.*, 139B, 73-80.
22. Li, M. D. (2006) The genetics of nicotine dependence. *Curr. Psychiatry. Rep.*, 8, 158-164.
23. Bierut, L. J., et al., (2006) Novel genes identified in a high-density genome wide association study for nicotine dependence, Hum. Mol. Genet., 16, 24-35.
24. Hochberg, Y. and Benjamini, Y. (1990) More powerful procedures for multiple significance testing. *Stat. Med.*, 9, 811-818.
25. Storey, J. D. (2002) A direct approach to false discovery rates. *J. R. Statist. Soc. B*, 64, 479-498.
26. CDC (2005) Annual smoking-attributable mortality, years of potential life lost, and productivity losses-United States. *Morbidity & Mortality Weekly Report*, 54, 625-628.
27. Lindstrom, J. M. (2003) Nicotinic acetylcholine receptors of muscles and nerves: comparison of their structures, functional roles, and vulnerability to pathology. *Ann. N.Y. Acad. Sci.*, 998, 41-52.
28. Salminen, O., Murphy, K. L., McIntosh, J. M., Drago, J., Marks, M. J., Collins, A. C. and Grady, S. R. (2004) Subunit composition and pharmacology of two classes of striatal presynaptic nicotinic acetylcholine receptors mediating dopamine release in mice. *Mol. Pharmacol.*, 65, 1526-1535.
29. Cserzo, M., Wallin, E., Simon, I., von Heijne, G. and Elofsson, A. (1997) Prediction of transmembrane alpha-helices in prokaryotic membrane proteins: the dense alignment surface method. *Protein Eng.*, 10, 673-676.
30. Stitzel, J. A., Dobelis, P., Jimenez, M. and Collins, A. C. (2001) Long sleep and short sleep mice differ in nicotine-stimulated 86Rb+ efflux and alpha4 nicotinic receptor subunit cDNA sequence. Pharmacogenetics, 4, 331-339.
31. Dobelis, P., Marks, M. J., Whiteaker, P., Balogh, S. A., Collins, A. C. and Stitzel, J. A. (2002) A polymorphism in the mouse neuronal alpha4 nicotinic receptor subunit results in an alteration in receptor function. *Mol. Pharmacol.*, 62, 334-342.
32. Butt, C. M., Hutton, S. R., Stitzel, J. A., Balogh, S. A., Owens, J. C. and Collins, A. C. (2003) A polymorphism in the alpha4 nicotinic receptor gene (Chrna4) modulates enhancement of nicotinic receptor function by ethanol. *Alcohol. Clin. Exp. Res.*, 27, 733-742.
33. Butt, C. M., King, N. M., Hutton, S. R., Collins, A. C. and Stitzel, J. A. (2005) Modulation of nicotine but not ethanol preference by the mouse Chrna4 A529T polymorphism. *Behav. Neurosci.*, 119, 26-37.
34. Lewohl, J. M., Wilson, W. R., Mayfield, R. D., Brozowski, S. J., Morrisett, R. A. and Harris, R. A. (1999) G-protein-coupled inwardly rectifying potassium channels are targets of alcohol action. *Nat. Neurosci.*, 12, 1084-1090.
35. Ma, J. Z., Beuten, J., Payne, T. J., Dupont, R. T., Elston, R. C. and Li, M. D. (2005) Haplotype analysis indicates an association between the DOPA decarboxylase (DDC) gene and nicotine dependence. *Hum. Mol. Genet.*, 14, 1691-1698.
36. Heatherton, T. F., Kozlowski, L. T., Frecker, R. C. and Fagerström, K. O. (1991) The Fagerström Test for Nicotine Dependence: a revision of the Fagerström Tolerance Questionnaire. *Br. J. Addict.*, 86, 1119-1127.
37. Saccone, S. F., Rice, J. P., Saccone, N. L. (2006) Power-based, phase-informed selection of single nucleotide polymorphisms for disease association screens. *Genet. Epidemiol.*, 30, 459-470.
38. Hinds, D. A., Stuve, L. L., Nilsen, G. B., Halperin, E., Eskin, E., Ballinger, D. G., Frazer, K. A. and Cox, D. R. (2005) Whole-genome patterns of common DNA variation in three human populations. *Science*, 18, 1072-1079.
39. Pritchard, J. K., Stephens, M. and Donnelly, P. J. (2000) Inference of population structure using multilocus genotype data. *Genetics*, 155, 945-959.
40. SAS Institute Inc. (2004) SAS Release 9.1.3, Cary, N.C.
41. Barrett, J. C., Fry, B., Maller, J. and Daly, M. J. (2005) Haploview: analysis and visualization of LD and haplotype maps. *Bioinformatics*, 15, 263-265.
42. Carlson, C. S., Eberle, M. A., Rieder, M. J., Yi, Q., Kruglyak, L. and Nickerson, D. A. (2004) Selecting a maximally informative set of single-nucleotide polymorphisms for association analyses using linkage disequilibrium. *Am. J. Hum. Genet.*, 74, 106-120.
43. Roeder, K., Bacanu, S.-A., Wasserman, L. and Devlin, B. (2006) Using linkage genome scans to improve power of association genome scans. *Am. J. Hum. Genet.*, 78, 243-252.
44. Benjamini, Y. and Hochberg, Y. (1995) Controlling the false discovery rate: a practical and powerful approach to multiple testing. *J. R. Stat. Soc. B*, 57, 289-300.
45. Storey, J. D. and Tibshirani, R. (2003) Statistical significance for genomewide studies. *Proc. Natl. Acad. Sci.*, 100, 9440-9445.
46. Stein, L. D., Mungall, C., Shu, S., Caudy, M., Mangone, M., Day, A., Nickerson, E., Stajich, J. E., Harris, T. W., Arva, A., et al. (2002) The generic genome browser: a building block for a model organism system database. *Genome. Res.*, 12, 1599-1610.

Example 4

Variants in Novel Genes Influence Nicotine Dependence

Tobacco use is a leading contributor to disability and death worldwide, and genetic factors contribute in part to the development of nicotine dependence. To identify novel genes for which natural variation contributes to the development of nicotine dependence, we performed a comprehensive genome wide association study using nicotine dependent smokers as cases and non-dependent smokers as controls. To allow the efficient, rapid, and cost effective screen of the genome, the study was carried out using a two-stage design. In the first stage, genotyping of over 2.4 million SNPs was completed in case and control pools. In the second stage, we selected SNPs for individual genotyping based on the most significant allele frequency differences between cases and controls from the pooled results. Individual genotyping was performed in 1050 cases and 879 controls using 31,960 selected SNPs. The primary analysis, a logistic regression model with covariates of age, gender, genotype and gender by genotype interaction, identified 35 SNPs with p-values less than $10^{-4}$ (minimum p-value $1.53 \times 10^{-6}$). Although none of the individual findings is statistically significant after correcting for multiple tests, additional statistical analyses support the existence of true findings in this group. Our study nominates several novel genes, such as Neurexin 1 (NRXN1), in the development of nicotine dependence while also identifying a known candidate gene, the β3 nicotinic cholinergic receptor.

Tobacco use, primarily through cigarette smoking, is responsible for about 5 million deaths annually, making it the largest cause of preventable mortality in the world (1), and nicotine is the component in tobacco that is responsible for the maintenance of smoking. Because of increasing tobacco use in developing nations, it is predicted that the death toll worldwide will rise to more than 10 million per year by 2020.

In the United States, 21% of adults were current smokers in 2004, with 23% of men and 19% of women smoking (2). Each year, approximately 440,000 people die of a smoking related illness (3). The economic burden of smoking is correspondingly high. Annual costs are estimated at $75 billion in direct medical expenses and $92 billion in lost productivity. The prevalence of cigarette smoking has decreased over the last 30 years in the U.S., primarily through smokers' successful efforts to quit. Yet, the rate of smoking cessation among adults has been slowing since the mid-1990's underscoring the limitations of current treatments for smoking. In addition, adolescents continue to initiate cigarette use, with 21% of high school students reporting cigarette smoking in the last month (4).

Smoking behaviors, including onset of smoking, smoking persistence (current smoking versus past smoking), and nicotine dependence, cluster in families (5), and large twin studies indicate that this clustering reflects genetic factors (6-10). Previous approaches have used genetic linkage studies (11-14) and candidate gene tests (15-17) to identify chromosomal regions and specific genetic variants suspected to be involved in smoking and nicotine dependence. We have extended the search for genetic factors by performing a high-density whole genome association study using a case-control design in unrelated individuals to identify common genetic variants that contribute to the transition from cigarette smoking to the development of nicotine dependence.

Results for Example 4

The final sample of 1,050 nicotine dependent case subjects and 879 non-dependent controls who smoked was examined for population stratification, and no evidence of admixture was observed. Quality control measures were applied to the individually genotyped SNPs and 31,960 SNPs were available for analysis.

Figure 16:
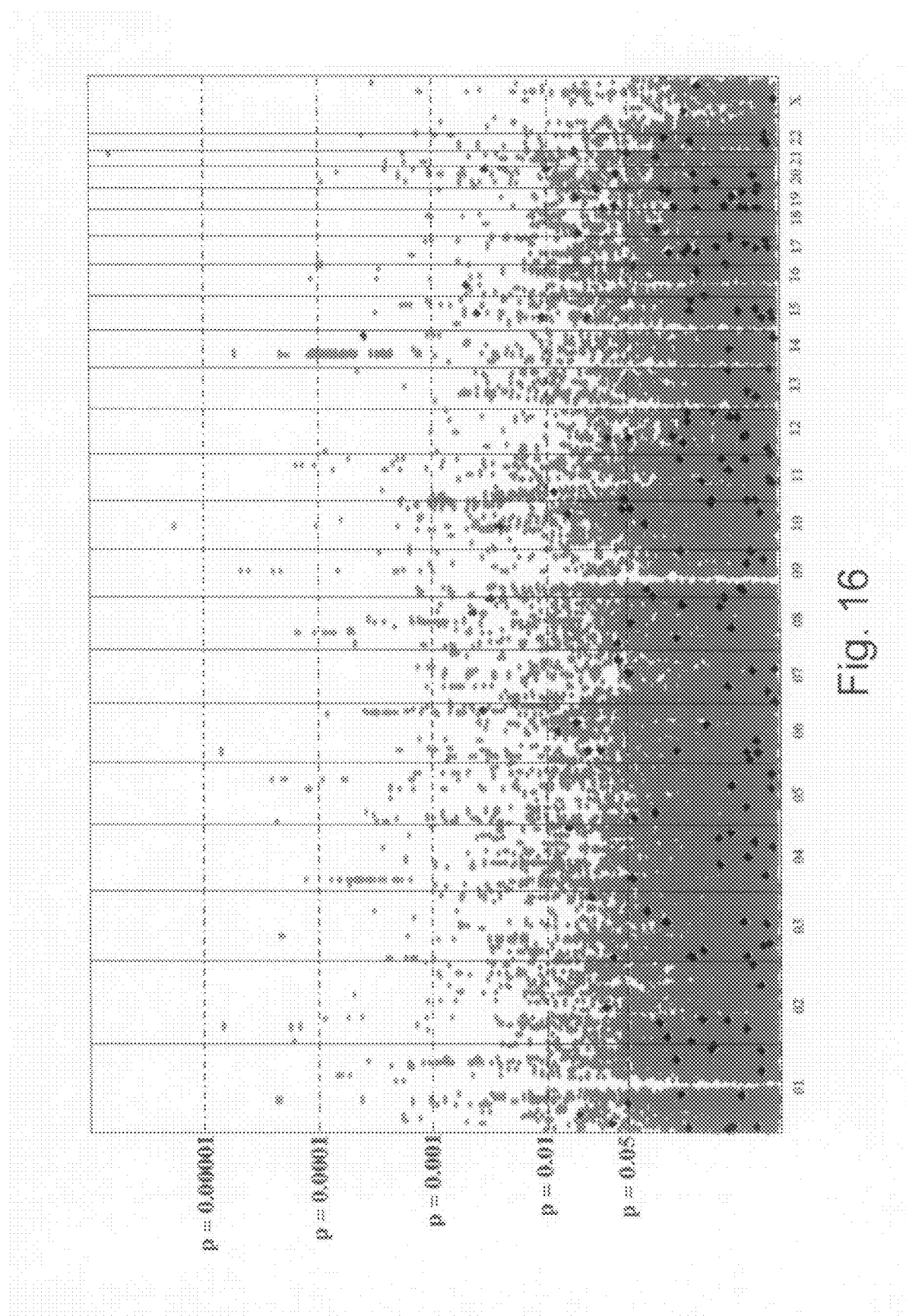
FIG. 16 shows P values of genome-wide association scan for genes that affect the risk of developing nicotine dependence.

The most significant findings are presented in Table 17 for those SNPs with a p value of less than $10^{-4}$. Several genes not previously implicated in the development of nicotine dependence are listed and their hypothesized mechanism of involvement is discussed below. The most significant result was observed with rs2836823 (p-value=$1.53 \times 10^{-6}$). This SNP is intergenic, as are several of the top findings. A SNP was defined as "intergenic" if it was not physically in a gene or within 10 kb of a known transcribed region. See FIG. 16 for an overview of the individual genotyping results. In FIG. 16, P values of genome-wide association scan for genes that affect the risk of developing nicotine dependence. $-\log_{10}(p)$ is plotted for each SNP in chromosomal order. The spacing between SNPs on the plot is based on physical map length. The horizontal lines show P values for logistic analysis. The vertical lines show chromosomal boundaries. Black diamonds represent SNPs that result in non-synonymous amino acid changes.

Because of the dense genome-wide scope of our study, the interpretation of these p-values was complicated by the large number of statistical tests. Approximately 2.4 million SNPs were examined in the pooled screening stage. Although this is a large sample with nearly 2,000 subjects, no SNP showed a genome-wide significant p-value after Bonferroni correction for multiple tests. Yet, several independent lines of evidence provided support that true genetic associations were identified in this top group of SNPs.

We used the agreement of direction of effect for the top SNPs in the Stage I samples (those included in the pooled genotyping, N=948) as compared with those samples added in Stage II (N=981) as a measure of evidence for real associations within the dataset. If there were no true associations in the data, the expectation would be a random assortment of effect direction between the two sample sets. In contrast, 30 of the top 35 SNPs in the Stage I samples show the same direction of effect in the additional Stage II sample set. This level of agreement was highly significant, with a p-value of $1.1 \times 10^{-5}$ from the binomial distribution indicating the error rate associated with rejecting the hypothesis of chance agreement. Thus, our top SNPs were enriched for real and reproducible allele frequency differences between cases and controls.

Further evidence for the presence of true associations came from comparison of these results with a candidate gene study conducted simultaneously [described above and in Saccone 18]. The β3 nicotinic receptor candidate gene, CHRNB3, the most significant finding in the candidate gene study, was also tagged by SNPs identified in the genome wide association study. This gene has a strong prior probability of a relationship with nicotine dependence, and the likelihood of any of the candidate genes in the above example being selected in the top group of SNPs in the genome wide association study is less than 5%.

Figure 17A:
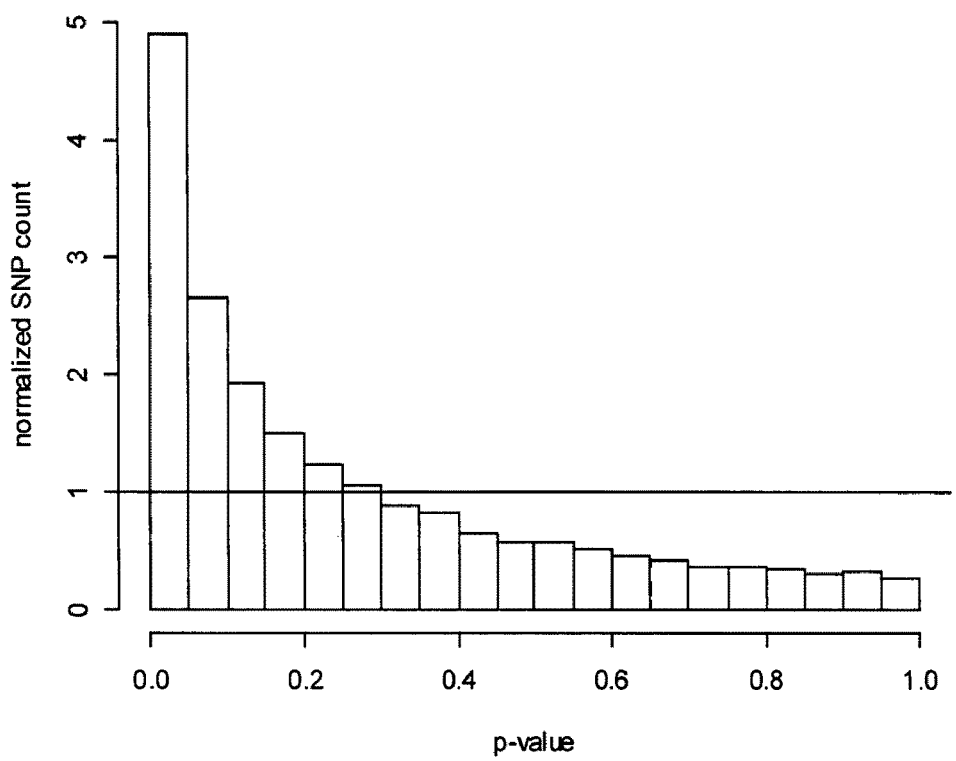
FIG. 17, Panels a and b, shows (A) distribution of p-values from the Stage I sample of the 31,960 individually genotyped SNPs that were selected from pooled genotyping stage and (B) distribution of p-values from the additional samples added in Stage II.
Figure 17B:
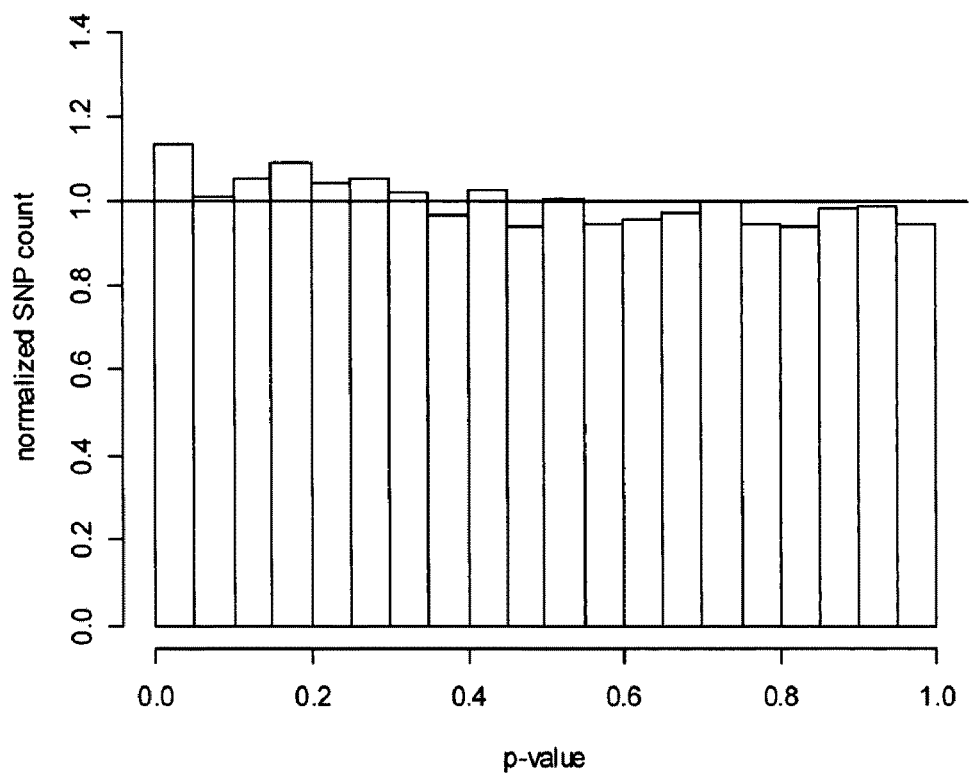

To investigate the accuracy of pooled genotyping estimates of the allele frequency differences between cases and controls, we examined the relationship between the pooled and individual genotyping results. The pooled genotyping indeed enriched the selected set of SNPs for sizable allele frequency differences between cases and controls included in the pooled study. When p-values were computed from individual genotypes using only Stage I samples, there is a strong enrichment of small p-values (see FIG. 17a). If the pooled genotyping was not at all successful, the distribution of p-values would be uniform, and if the pooling was completely accurate, then only small p-values would be present in the individual genotyping stage assessed in this sample subset. As seen in FIG. 17a, our results lie between these extremes. We also examined the p-values of the samples added into the Stage II that were not in the pooling step. Because these Stage II samples are an independent random sample from the case and control populations, they are not expected to show the same allele frequency differences as Stage I samples where those differences are due to sampling error. Thus, their p-values should be uniformly distributed except for possible real associations, which would be consistent between the two sets of samples. This is seen in FIG. 17b. The graph is fairly uniform with only a slight increase in small p-values. In FIG. 17, Panel A shows distribution of p-values from the Stage I sample of the 31,960 individually genotyped SNPs that were selected from pooled genotyping stage. The distribution shows that the pooled genotyping produced an enrichment of SNPs with small p-values. A uniform distribution from 0-1 would be expected if there were no correlation between pooled genotyping and individual genotyping. Panel B in FIG. 17 shows distribution of p-values from the additional samples added in Stage II. The distribution is fairly uniform with only a slight enrichment of small p-values.

Figure 18:
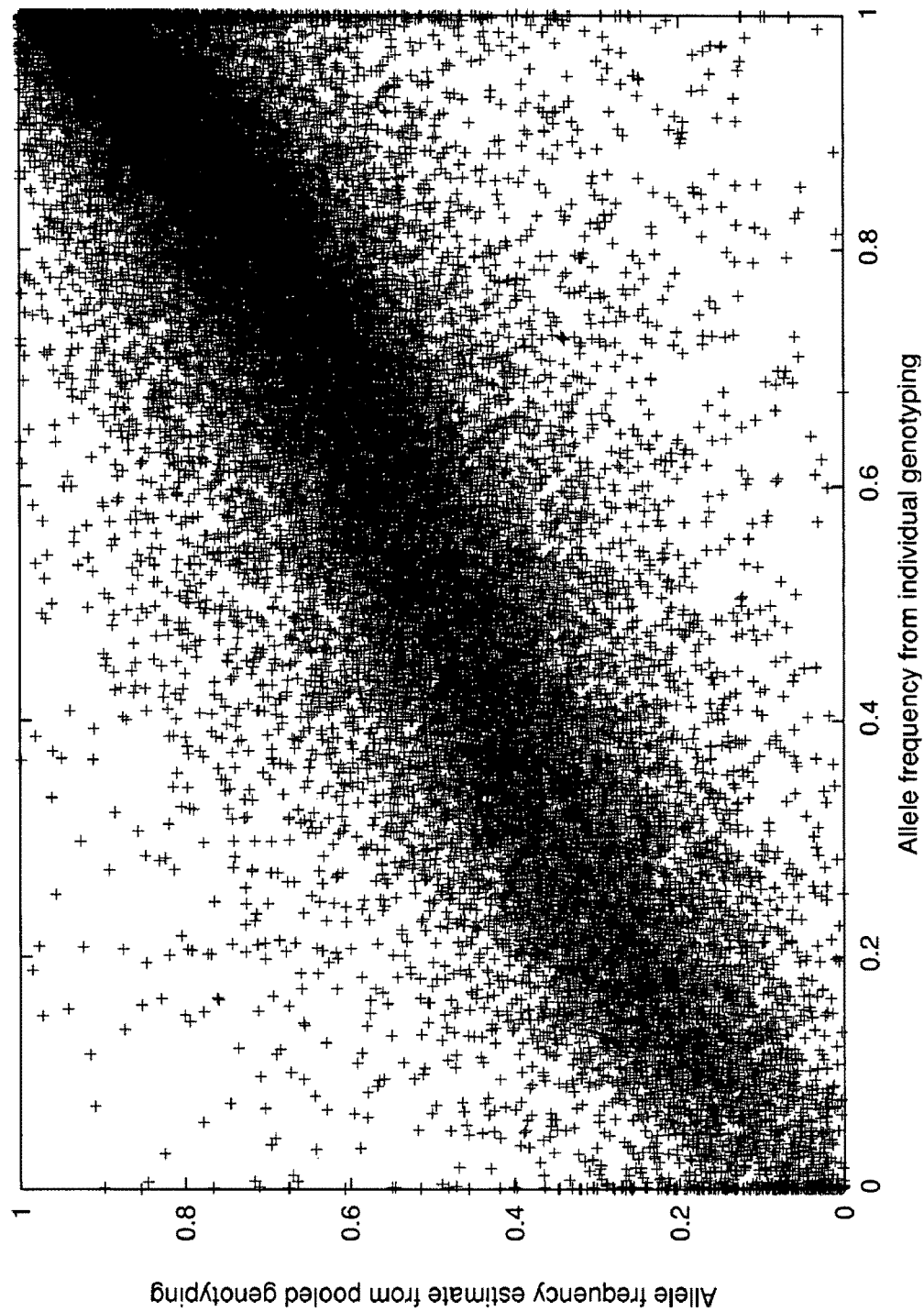
FIG. 18 shows a scatter plot of the allele frequencies from pooling and individual genotyping from the Stage I sample.

In addition, we directly compared allele frequency estimates based on the pooled genotyping with those based on individual genotyping. As seen in FIG. 18, the majority of the allele frequency estimates from the pooled and individual genotyping results lie along the diagonal. A similar finding is seen if case or control samples are examined separately. We computed a correlation of 87% between allele frequencies estimated from the case pooled genotyping and allele frequencies computed in the individual genotyping sample of cases from Stage I (case subjects N=482). Similarly, there was an 84% correlation of allele frequencies seen in the comparison of the pooled and individual genotyping in the control sample from Stage I (control subjects N=466). When we compared the allele frequency differences between cases and controls in pools (which is implicitly large because the SNPs were selected for individual genotyping) with the difference between cases and controls in the individual genotyping, we found a 58% correlation. This indicates a high level of concordance between the pooled and individual genotyping results; thus, the pooled genotyping was successful in identifying SNPs that would show allele frequency differences in individually genotyped case and control subjects. FIG. 18 shows a scatter plot of the allele frequencies from pooling and individual genotyping from the Stage I sample.

Lastly, we examined potential differences between the U.S. and Australian samples. A comparison of cases and controls from the two populations did not show any significant differences by gender or stratification results.

Discussion of Example 4

Smoking contributes to the morbidity and mortality of a large component of the population, and twin studies provide strong evidence that genetic factors contribute substantially to the risk of developing nicotine dependence. This is the first high density, genome wide association study with the goal to identify common susceptibility or resistance gene variants for nicotine dependence.

Several novel genes were identified in this study as potential contributors to the development of nicotine dependence, such as Neurexin 1 (NRXN1). There were at least two signals in NRXN1. See Table 18. The SNP rs10490162 is weakly correlated with the other two SNPs that were genotyped in the gene (maximum pair wise correlation is $r^2$=0.45 with the other two SNPs, which were found to be in strong disequilibrium with each other). Interestingly, another neurexin gene, Neurexin 3 (NRXN3), was reported as a susceptibility gene for polysubstance addiction in a pooled genome wide association study by Uhl and colleagues (19). In addition, the most significant SNP in NRXN3 in our study, rs2221299, had a p-value of 0.0034. While there was substantially less evidence for association with NRXN3 in our study, the fact that two independent studies of substance dependence found evidence of association with neurexin genes merits further investigation.

The neurexin gene family is a group of polymorphic cell surface proteins expressed primarily in neurons that function in cell-cell interactions and are required for normal neurotransmitter release (20). Neurexins are important factors in GABAergic and glutamatergic synapse genesis and are the only known factors reported to induce GABAergic postsynaptic differentiation. NRXN1 and NRXN3 are among the largest known human genes, and they utilize at least two promoters and alternatively spliced exons to produce thousands of distinct mRNA transcripts and protein isoforms. It is hypothesized that differential expression of neurexin isoforms by GABAergic and glutamatergic neurons contribute to the local induction of postsynaptic specialization. Because substance dependence is modeled as a relative imbalance of excitatory and inhibitory neurotransmission (or related to "disinhibition") (1), the neurexin genes are plausible new candidate genes that contribute to the neurobiology of dependence through the regulated choice between excitatory or inhibitory pathways. Biological characterization of these genes may define a role of neural development or neurotransmitter release and dependence.

This study also identified a vacuolar sorting protein, VPS13A, as a potential contributor to nicotine dependence. Interestingly, three independent genetic linkage studies of smoking (11-13) identified a region on chromosome 9 near this gene. This gene appears to control the cycling of proteins through the cell membrane, and there are numerous alternative transcripts. Variants in the VPS13A gene cause progressive neurodegeneration and red cell acanthocytosis (22). Another novel gene for further study is TRPC7 (transient receptor potential canonical) channel which encodes a subunit of multimeric calcium channels (23). A recent study using animal model indicated that TRPC channels can functionally regulate nicotine-induced neuronal activity in the locomotion circuitry (24).

There are several other genes tagged by the top SNPs. An alpha catenin gene, CTNNA3, inhibits Wnt signaling and has variants that affect the levels of plasma amyloid beta protein (Abeta42) in Alzheimer's disease families (25), though other reports fail to find an association with Alzheimer's disease (26). The CLCA1 gene encodes a calcium-activated chloride channel that may contribute to the pathogenesis of asthma (27) and chronic obstructive pulmonary disease (28). While none of these genes has a known relationship to nicotine metabolism or mechanism of action, they are involved in brain and lung function and therefore have plausible biological relationships to smoking behavior and dependence.

In addition to the novel genes implicated in the genome wide association study, a classic candidate gene, the β3 nicotinic receptor (CHRNB3) is among the top group. The nicotinic receptors are a family of ligand-gated ion channels that mediate fast signal transmission at synapses. Nicotine is an agonist of these receptors that produce physiological responses.

The SNPs were tested for varying gender effects as part of the primary analytic model. Several of the top SNPs had significantly different odds ratios for men and women (Table 17). It is clear from epidemiological data that there are significant gender differences in the risk for the development of dependence, and this study provides evidence that separate genes may contribute to the development of nicotine dependence in men and women. Following the primary analyses, we further analyzed the top ranked SNPs to determine if there was evidence for other modes of transmission, such as recessive or dominant models. There was no evidence for improvement in the fit for either of these models for any of the SNPs in the top group.

The maximum effect size for these top associated SNPs is an odds ratio of 2.53. These estimates are likely to be overestimates of the true population values due to the "jackpot effect" of many multiple comparisons. Several alternatives exist for correction of these estimates, but have not been applied to these data. The effect size estimates are consistent with multiple genes of modest effect contributing to the development of dependence.

This genome wide association study is a first step in a large-scale genetic examination of nicotine dependence. Our analytic plan was determined a priori so that we would be able to interpret the results most clearly. We purposefully chose to examine the entire sample as the primary analysis, rather than use a split sample design because we felt that this had the greatest power to detect true findings (29).

Several other issues are optionally contemplated in examination of these data. For example, smoking and nicotine dependence are correlated with many other disorders, such as alcohol dependence and major depressive disorder (30-33). Preliminary analyses of our sample have confirmed that this clustering of other disorders with nicotine dependence is present in our sample. In addition, nicotine dependence can be defined by other measures, such as the American Psychiatric Association criteria in the Diagnostic and Statistical Manual, Version IV (DSM-IV) (34). Previous work has shown that though different measures of nicotine dependence are correlated, there is not perfect overlap because the FTND and DSM-IV definitions focus on different features of dependence (35). The FTND is a measure that focuses on physiological dependence, whereas the DSM-IV dependence includes cognitive and behavioral aspects of dependence. Different classification by FTND and DSM-IV nicotine dependence is also seen in our sample with 75% of our cases (FTND≧4) and 24% of our controls (FTND=0) affected with DSM-IV nicotine dependence. It is also contemplated that comorbid disorders and varying definitions of nicotine dependence can be examined to explicate some of the individual features that contribute to these findings of association.

In summary, efforts to understand nicotine dependence are important so that new approaches can be developed to reduce tobacco use, especially cigarette smoking. This systematic survey of the genome nominates novel genes, such as NRXN1, that increase an individual's risk of transitioning from smoking to nicotine dependence. The genetic and biological characterization of these genes helps in understanding the underlining causality of nicotine dependence and can optionally provide novel drug development targets for smoking cessation. These variants are also optionally involved in addictive behavior in general. The current pharmacological treatments for nicotine dependence continue to produce only limited abstinence success, and the tailoring of medications to promote smoking cessation to an individual's genetic background (e.g., via the current invention) may significantly increase the efficacy of treatment. Our work can optionally facilitate personalized approaches in the practice of medicine through large-scale study of genetic variants. Novel targets can now be studied and hopefully will facilitate the development of improved treatment options to alleviate this major health burden and reduce smoking related deaths.

Materials and Methods for Example 4

The purpose of this study was to identify genes contributing to the progression from smoking to the development of nicotine dependence. As a result, the study examined the phenotypic contrast between nicotine dependent subjects and individuals who smoked but never developed nicotine dependence.

Subjects

All subjects (1050 cases and 879 controls) were selected from two ongoing studies: the Collaborative Genetic Study of Nicotine Dependence, a United States based sample (St. Louis, Detroit, and Minneapolis), and the Nicotine Addiction Genetics study, an Australian based, European-Ancestry sample. The United States sample was recruited through telephone screening of community based subjects to determine eligibility for recruitment as case (current FTND≧4) or control status. Qualifying subjects were invited to participate in the genetic study. The Australian participants were enrolled at the Queensland Institute of Medical Research as families and spouses of the Australian Twin Panel.

The Institutional Review Board approved both studies, and all subjects provided informed consent to participate. Blood samples were collected from each subject for DNA analysis and submitted together with electronic phenotypic data to the NIDA Center for Genetic Studies, which manages the sharing of research data in accordance with NIH guidelines. All subjects were self-identified as being of European descent. See Table 19 for further demographic details.

Phenotype Data

Equivalent assessments were performed at both sites. A personal interview that comprehensively assessed nicotine dependence using several different criteria such as the Fagerström Test for Nicotine Dependence (36) and the Diagnostic and Statistical Manual of Mental Disorders-IV (34) was administered.

Case Definitions of Nicotine Dependence

The focus of this example was a case-control design of unrelated individuals for a genetic association study of nicotine dependence. Cases were defined by a commonly used definition of nicotine dependence, a Fagerström Test for Nicotine Dependence (FTND) score of 4 or more when smoking the most (maximum score of 10) (36). No significant difference was observed in FTND score between the U.S. and Australian samples (mean FTND: 6.43 for U.S. and 6.06 for Australian cases).

Control Definitions

Control subject status was defined as an individual who smoked (defined by smoking at least 100 cigarettes during their lifetime), yet never became dependent (lifetime FTND=0). Historically, the threshold of smoking 100 or more cigarettes has been used in survey research as a definition of a "smoker." With the selection of controls who smoked, the study focused on those genetic effects related to the transition from smoking to the development of nicotine dependence. Additional data from the Australian twin panels supports this designation of a control status. Among monozygotic twins who smoked, the rate of nicotine dependence, defined as a score of 4 or more using the Heavy Smoking Index (HSI—an abbreviated version of the FTND) (37), was lowest in those whose co-twin had an HSI score of 0; lower even than in those whose co-twin had experimented with cigarettes, but never became a smoker, or those whose co-twin had never smoked even a single cigarette (see Table 20).

DNA Preparation

DNA was extracted from whole blood and EBV transformed cell lines and was aliquoted and stored frozen at −80° C. until distributed to the genotyping labs.

Study Design

To allow the efficient, rapid, and cost-effective screening of over 2.4 million SNPs, we performed a whole genome association study using a two-stage design.

Stage I—Pooled Genotyping High-Density Oligonucleotide Genotyping Arrays:

In Stage I, 482 case and 466 control DNA samples from U.S. and Australian subjects of European ancestry were selected for study. To examine potential population stratification, we performed a STRUCTURE analysis (38) using 295 individually genotyped SNPs. The selected SNPs were roughly evenly spaced across the autosomes and were selected for stratification analyses (39). The STRUCTURE program identifies subpopulations of individuals who are genetically similar through a Markov chain Monte Carlo sampling procedure using markers selected across the genome. There was no evidence of population admixture. Cases and controls were then placed in pools for genotyping of 2.4 million SNPs, and estimates of allele frequency differences between case and control pools were determined.

Pooled genotyping was performed using 8 case and 8 control pools. DNA was quantified using Pico Green. The concentrations were normalized and verified to within a coefficient of variation of <10%. Equimolar amounts of DNA from approximately 60 individuals were placed into each of the 16 pools. An individual's sample was included in only one pool. The 16 pools were hybridized to 49 chip designs to interrogate U.S. Pat. No. 2,427,354 SNPs across the whole genome.

Determination of Pooled Allele Frequency Estimates:

Allele frequencies were approximated using the intensities collected from the high-density oligonucleotide arrays. A SNP's allele frequency p was a ratio of the relative amount of the DNA with reference allele to the total amount of DNA, and thus can have values between 0 and 1:

$$p = \frac{C_{Ref}}{C_{Ref} + C_{Alt}}$$

where $C_{Ref}$ and $C_{Alt}$ are the concentrations of reference allele and alternate allele, respectively. As probe intensities were directly related to the concentrations of the SNP alleles, the $\hat{p}$ computed from the intensities of reference and alternate features was a good approximation of the true allele frequency p. The $\hat{p}$ value was computed from the trimmed mean intensities of perfect match features, after subtracting a measure of background computed from trimmed means of intensities of mismatch features:

$$\hat{p} = \frac{I_{PM,Ref}^{TM} - I_{MM}^{TM}}{(I_{PM,Ref}^{TM} - I_{MM}^{TM}) + (I_{PM,Alt}^{TM} - I_{MM}^{TM})}$$

where $$I_{MM}^{TM} = (I_{MM,Ref,Fwd}^{TM} + I_{MM,Ref,Rev}^{TM} + I_{MM,Alt,Fwd}^{TM} + I_{MM,Alt,Rev}^{TM})/4$$

$$I_{PM,Ref}^{TM} = (I_{PM,Ref,Fwd}^{TM} + I_{PM,Ref,Rev}^{TM})/2$$

$$I_{PM,Alt}^{TM} = (I_{PM,Alt,Fwd}^{TM} + I_{PM,Alt,Rev}^{TM})/2$$

$I^{TM}$ was the trimmed mean of perfect match or mismatch intensities for a given allele and strand denoted by the subscript. The trimmed mean disregarded the highest and the lowest intensity from the 5 perfect match intensities and also from the 5 mismatch intensities in the 40-feature tilings before computing the arithmetic mean.

Three quality control metrics were developed to assess the reliability of the intensities for a SNP on an array scan. The first metric, concordance, evaluated the presence of a target for a SNP. The second metric, signal to background ratio, related the amount of specific and non-specific binding, estimated from the intensities of perfect match and mismatch features. The third metric tracked the number of features in each SNP tiling that had saturated intensities. Cutoffs were applied to all three metrics, and SNP feature sets that did not pass were discarded from further evaluation.

Concordance was computed independently for both reference and alternate allele feature sets, then a maximum was taken of the two values. For each allele at each offset for both the forward and reverse strand feature sets, the identity of the brightest feature was noted. The concordance for a particular allele was computed as a ratio of the number of times the perfect match feature was the brightest to the total number of offsets over the forward and reverse strands. In the 40 feature SNP tiling each allele was represented by 20 features, distributed along 5 offsets and forward and reverse strands. If $N_{PM}^X$ was the number of times for allele X when the perfect match feature was brighter than the mismatch feature over all offsets and both strands, then:

$$\text{concordance} = \max\left(\frac{N_{PM}^{Ref}}{10}, \frac{N_{PM}^{Alt}}{10}\right)$$

SNP feature sets with concordance <0.9 were discarded from further evaluation.

Signal to background ratio was the ratio between the amplitude of signal, computed from trimmed means of perfect match feature intensities, and amplitude of background, computed from trimmed means of mismatch feature intensities. The signal and background were computed as follows:

$$\text{signal} = \sqrt{((I_{PM,Ref,Fwd}^{TM} + I_{PM,Ref,Rev}^{TM})/2)^2 + ((I_{PM,Alt,Fwd}^{TM} + I_{PM,Alt,Rev}^{TM})/2)^2}$$

$$\text{background} = \sqrt{((I_{MM,Ref,Fwd}^{TM} + I_{MM,Ref,Rev}^{TM})/2)^2 + ((I_{MM,Alt,Fwd}^{TM} + I_{MM,Alt,Rev}^{TM})/2)^2}$$

The trimmed mean intensities $I^{TM}$ for both the perfect match and mismatch feature sets were obtained as described above. SNP feature sets with signal/background <1.5 were discarded from further evaluations.

The number of saturated features was computed as the number of features that reached the highest intensity possible for the digitized numeric intensity value. SNPs with number of saturated features >0 were discarded from further evaluations.

Stage II SNP Selection:

Computation of Empirical P-Values to Evaluate Each SNP's Association Independently Corrected t-test P-values were computed similarly to regular t-test P-values. For testing of the difference between average case $\hat{p}$ and average control $\hat{p}$, the standard error was corrected by a chip design-specific additive constant. The additive constant was obtained by minimizing the coefficient of variation of the t-tests for each chip design. This standard error additive constant ensured that SNP selection was not biased to low or high standard errors, as there was no prior evidence that SNPs with low or high standard errors were more or less likely to be associated with the phenotype. The empirical P-values were computed from ranks of the corrected t-test P-values for each chip design by dividing the rank by the total number of passing SNPs on the chip design. See FIG. 19 for a distribution of standard errors.

SNP Selection Criteria

The SNPs were selected from among SNPs that had at least two passing $\hat{p}$ values for cases and controls. Selected SNPs mapped onto human genome build 35 and had successfully designed assays. An empiral P-value cutoff of 0.0196 was used to select SNPs.

Stage II Individual Genotyping

For individual genotyping, we designed a custom array to interrogate 41,402 SNPs that included SNPs selected from the pooled genotyping (39,213) and stratification and quality control SNPs (2,189). In Stage II, we performed individual genotyping on the original case and control samples and additional case and control subjects of European descent, for a final sample size of 1,929 individuals (1,050 cases and 879 controls).

Individual genotypes were determined by clustering all SNP scans in the 2-dimensional space defined by reference and alternate perfect match trimmed mean intensities. Trimmed mean intensities were computed as described above in section "Determination of Pooled Allele Frequency Estimates". The genotype clustering procedure was an iterative algorithm developed as a combination of K-means and constrained multiple linear regressions. The K-means at each step reevaluated the cluster membership representing distinct diploid genotypes. The multiple linear regressions minimized the variance in $\hat{p}$ within each cluster while optimizing the regression lines' common intersect. The common intersect defined a measure of common background that was used to adjust the allele frequencies for the next step of K-means. The K-means and multiple linear regression steps were iterated until the cluster membership and background estimates converged. The best number of clusters was selected by maximizing the total likelihood over the possible cluster counts of 1, 2 and 3 (representing the combinations of the 3 possible diploid genotypes). The total likelihood was composed of data likelihood and model likelihood. The data likelihood was determined using a normal mixture model for the distribution of $\hat{p}$ around the cluster means. The model likelihood was calculated using a prior distribution of expected cluster positions, resulting in optimal $\hat{p}$ positions of 0.8 for the homozygous reference cluster, 0.5 for the heterozygous cluster and 0.2 for the homozygous alternate cluster.

A genotyping quality metric was compiled for each genotype from 15 input metrics that described the quality of the SNP and the genotype. The genotyping quality metric correlated with a probability of having a discordant call between the Perlegen platform and outside genotyping platforms (i.e., non-Perlegen HapMap project genotypes). A system of 10 bootstrap aggregated regression trees was trained using an independent data set of concordance data between Perlegen genotypes and HapMap project genotypes. The trained predictor was then used to predict the genotyping quality for each of the genotypes in this data set.

Figure 19:
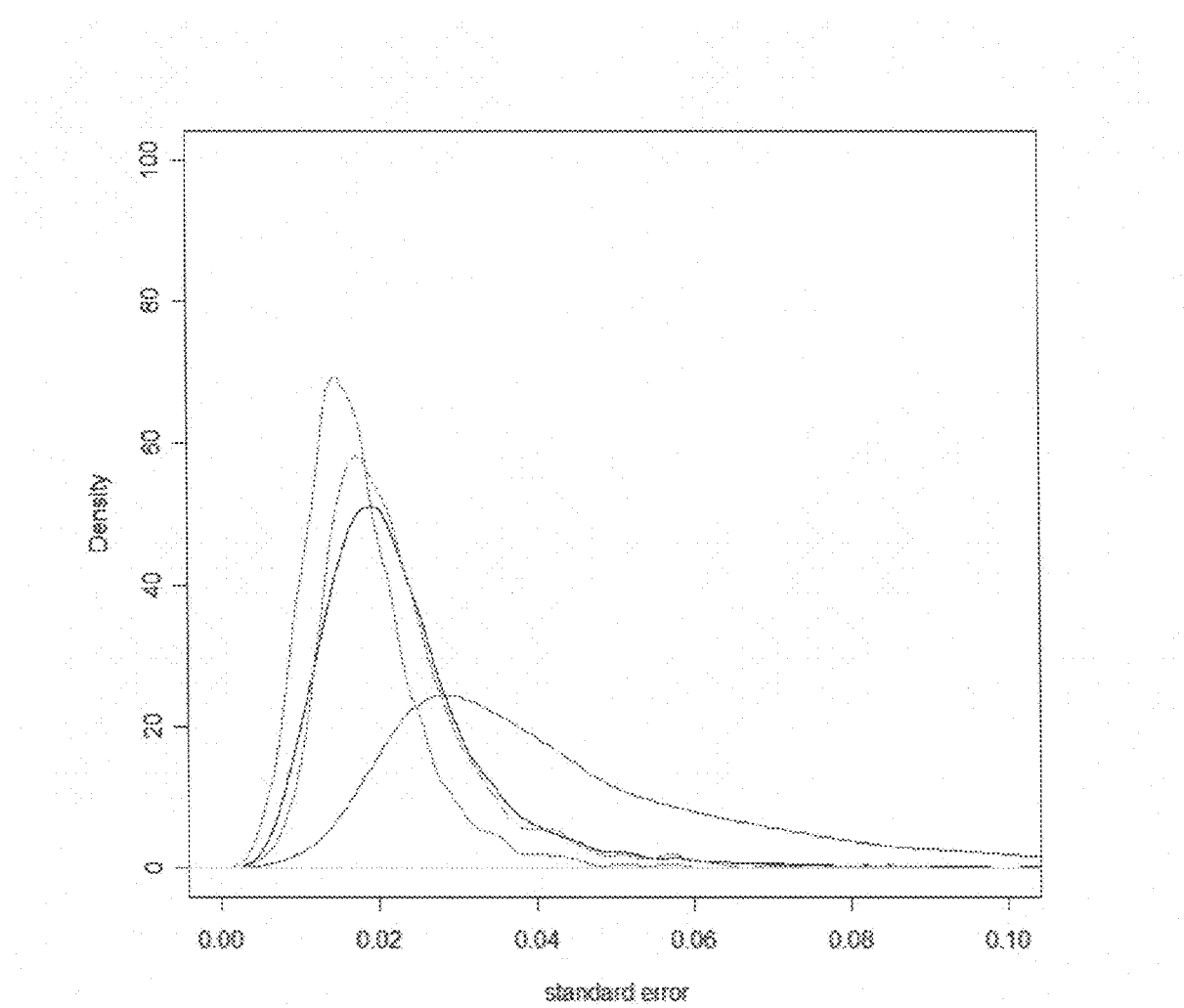
FIG. 19 shows a plot of distributions of standard errors of SNPs selected using different criteria.

FIG. 19 shows a plot of distributions of standard errors of SNPs selected using different criteria. The plot illustrates that delta $\hat{p}$ cutoff selects preferentially SNPs with high standard errors of delta $\hat{p}$, regular t-test preferentially selects SNPs with low standard errors and the corrected t-test is centered on the standard error distribution from all SNPs. In the standard error density comparison in FIG. 19, the red (highest peak) =t-test, the green (second highest peak)=corrected t-test, the black (third highest peak)=all SNPs, and the blue (lowest peak)=delta phat.

Hardy Weinberg Equilibrium

Hardy Weinberg Equilibrium (HWE) was tested separately for cases and controls. SNPs that did not follow HWE at a level of p-value $<10^{-15}$ in either cases or controls were discarded. There were 859 and 797 autosomal SNPs excluded because of this extreme disequilibrium in cases and controls, respectively, and 765 of these SNPs were common to both groups. This level of deviation from HWE indicates issues with SNP genotyping and clustering. Because association with the phenotype can result in SNPs not being in HWE, SNPs with HWE p-values between $10^{-4}$ and $10^{-15}$ were visually inspected, and where problems with clustering were detected, the SNP was discarded from further analysis. This results in 31,960 SNPs available for analysis.

Population Stratification

Figure 20:
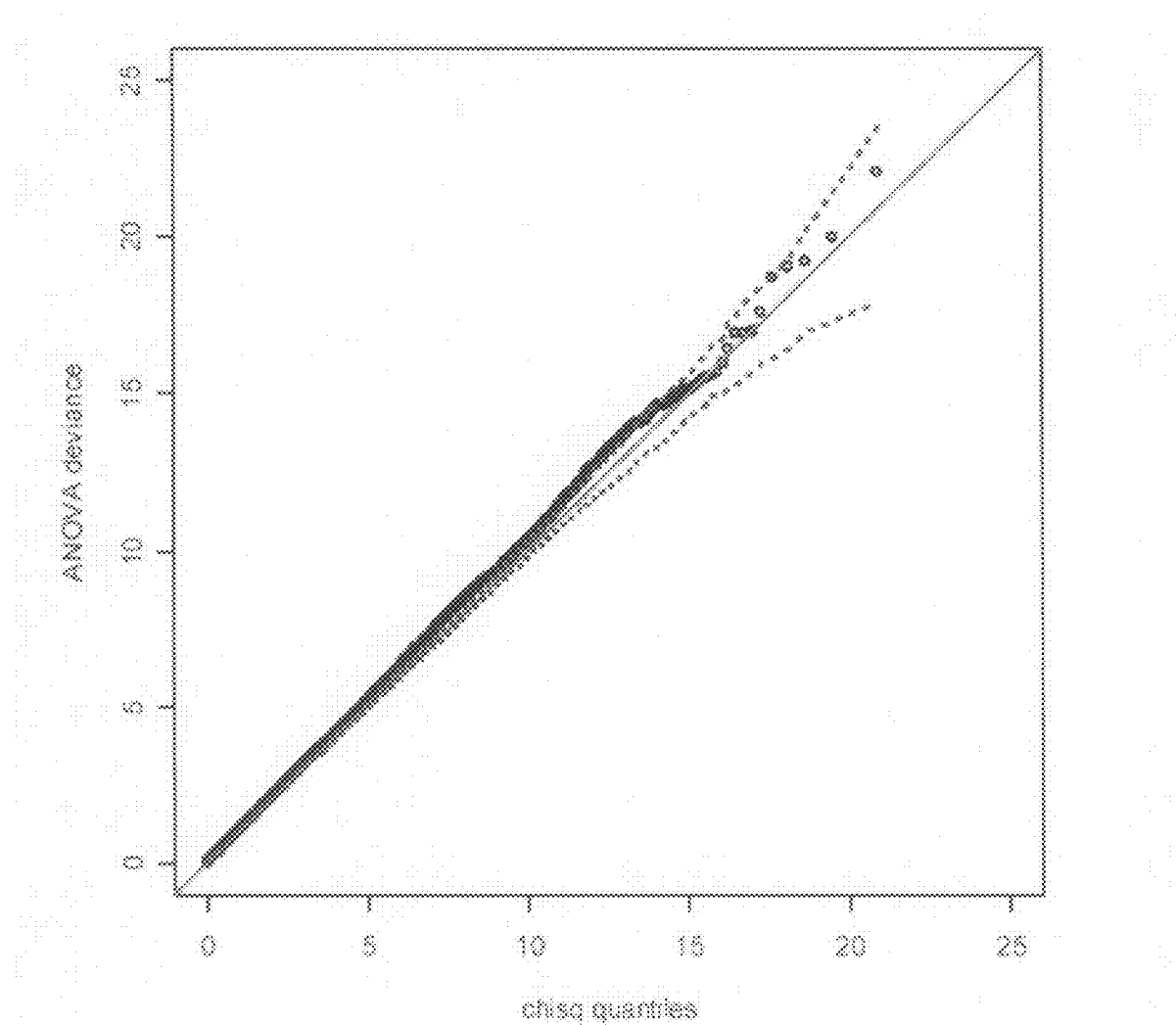
FIG. 20 shows Q-Q plot of logistic regression ANOVA deviance produced from samples added to Stage I samples at Stage II.

In order to avoid false positive results due to cryptic population stratification in the larger sample, we repeated a STRUCTURE analysis in the expanded sample of 1929 subjects (38) using genotype data for 289 well performing SNPs (39). This again revealed no evidence of population admixture. Additionally, the non-inflated Q-Q plot of test statistics in the Stage II only samples (FIG. 20) indicates a lack of population admixture correlated with case control status. FIG. 20 shows Q-Q plot of logistic regression ANOVA deviance produced from samples added to Stage I samples at Stage II. Because these samples are independent of Stage I samples used for the SNP selection from pooled genotyping the test statistic is expected to largely follow the null distribution (Chi-square distribution with 2 degrees of freedom). Due to the lower power of this sample set compared to the combined set of samples and the small effect sizes found in this study, any possible associations are not expected to cluster together at low p-values, thereby changing the linear shape of this Q-Q plot. The dotted line represents 95% point-wise confidence envelope of expected null distribution.

Covariate Analysis

The covariates available for individuals were sex, age, site (U.S. or Australia) and sample (first or second). Prior to performing genetic analyses, inspection of the data indicated that the covariates of gender and recruitment site were important predictors of case and control status and were used as covariates in the logistic regression model.

Genetic Association

We developed an a priori analytic strategy so that we could then interpret our results and avoid issues of multiple testing from using varying methods of analysis. We chose to examine the total sample of 1929 individuals in the primary analysis because this had the greatest power to detect true findings (29). For our primary single SNP association analyses, we used logistic regression to incorporate the significant covariates sex and site (U.S., Australia), and tested the effect of genotype together with a genotype-by-sex interaction term using a standard likelihood-ratio chi-squared statistic with 2 degrees of freedom. This approach allowed us to detect SNPs having gender-specific effects as well as SNPs with similar effects in males and females. For these primary analyses, we coded genotype according to the number of "risk" alleles (0, 1 or 2) where the risk allele was defined to be the allele having higher frequency in cases than in controls. This coding was additive on the log scale and thus corresponded to a multiplicative genetic model. The full model was compared to a reduced model including gender and recruitment site only, and significance was assessed by a chi square test with 2 degrees of freedom. The resulting p-values were used to rank the SNPs.

Following these primary analyses, we further analyzed the top ranked SNPs to determine if there was significant evidence for alternative modes of transmission such as dominant or recessive models.

TABLE 17

SNPs with primary model p-value < 0.0001. Listed genes are within 10 kb of the SNP position.

| SNP | Gene | Chr | Pos(bp) | Risk Allele[h] | Primary p-value | Male odds ratio (95% CI) | Female odds ratio (95% CI) |
|---|---|---|---|---|---|---|---|
| rs2836823 |  | 21 | 39,302,119 | T (0.48/0.4) | 1.53E−06 | 1.35 (1.08-1.68) | 1.46 (1.23-1.73) |
| rs4142041 | CTNNA3 | 10[a] | 68,310,957 | G (0.41/0.34) | 5.64E−06 | 1.73 (1.37-2.2)* | 1.14 (0.97-1.35)* |
| rs999[i] | GPSM3, AGPAT1, NOTCH4, RNF5, AGER, PBX2, AGER | 6 | 32,261,864 | C (0.96/0.94) | 1.42E−05 | 1.92 (1.06-3.45) | 2.53 (1.62-3.95) |
| rs12623467 | NRXN1 | 2[g] | 51,136,740 | C (0.96/0.92) | 1.48E−05 | 2.42 (1.51-3.88) | 1.57 (1.14-2.16) |
| rs1782159 |  | 14[b] | 40,826,319 | C (0.25/0.2) | 1.87E−05 | 1.97 (1.46-2.65)* | 1.09 (0.87-1.36)* |
| rs12380218 | VPS13A | 9[c] | 77,165,214 | G (0.24/0.19) | 2.09E−05 | 1.18 (0.9-1.55) | 1.56 (1.28-1.91) |
| rs2022443 | VPS13A | 9[c] | 77,099,406 | G (0.24/0.19) | 2.49E−05 | 1.12 (0.86-1.45)* | 1.57 (1.29-1.91)* |
| rs2673931 | TRPC7 | 5[d] | 135,717,335 | T (0.66/0.61) | 3.89E−05 | 1.68 (1.34-2.12)* | 1.04 (0.87-1.24)* |
| rs4142603 |  | 9[c] | 76,998,948 | C (0.25/0.19) | 4.05E−05 | 1.15 (0.9-1.47) | 1.52 (1.26-1.84) |
| rs1031006 |  | 5 | 14,040,103 | A (0.67/0.62) | 4.30E−05 | 0.98 (0.78-1.24)* | 1.49 (1.25-1.78)* |
| rs2791480 | CLCA1 | 1 | 86,680,605 | G (0.78/0.72) | 4.38E−05 | 1.53 (1.19-1.97) | 1.33 (1.1-1.61) |
| rs10049135 |  | 3 | 72,731,670 | A (0.89/0.86) | 4.65E−05 | 2.09 (1.51-2.91)* | 0.96 (0.75-1.24)* |
| rs11145381 | VPS13A | 9[c] | 77,144,695 | C (0.23/0.18) | 4.72E−05 | 1.19 (0.91-1.57) | 1.54 (1.26-1.88) |
| rs2798983 |  | 14[b] | 40,841,983 | C (0.28/0.22) | 4.77E−05 | 1.63 (1.25-2.13) | 1.28 (1.05-1.55) |
| rs2546657 | TRPC7 | 5[d] | 135,711,634 | A (0.66/0.62) | 4.96E−05 | 1.67 (1.33-2.09)* | 1.01 (0.85-1.2)* |
| rs1782182 |  | 14[b] | 40,766,891 | G (0.31/0.25) | 5.28E−05 | 1.72 (1.33-2.22)* | 1.14 (0.95-1.38)* |
| rs10490162 | NRXN1 | 2 | 51,159,308 | T (0.91/0.86) | 5.66E−05 | 1.92 (1.34-2.75) | 1.39 (1.08-1.79) |
| rs11694463 |  | 2 | 12,732,219 | C (0.12/0.09) | 6.10E−05 | 2.1 (1.4-3.15) | 1.37 (1.05-1.78) |
| rs17706334 |  | 11[e] | 108,486,074 | A (0.97/0.94) | 6.38E−05 | 1.71 (1.05-2.8) | 2.19 (1.44-3.33) |
| rs17706299 |  | 11[e] | 108,486,027 | C (0.97/0.94) | 6.51E−05 | 1.71 (1.05-2.79) | 2.19 (1.44-3.33) |
| rs13277254 | CHRNB3 | 8[f] | 42,669,139 | A (0.81/0.76) | 6.54E−05 | 1.19 (0.92-1.55) | 1.55 (1.26-1.91) |
| rs12467557 | NRXN1 | 2[g] | 51,153,921 | A (0.96/0.93) | 6.88E−05 | 2.53 (1.48-4.31) | 1.62 (1.14-2.3) |
| rs17633258 |  | 11[e] | 108,491,084 | C (0.97/0.94) | 7.31E−05 | 1.9 (1.14-3.15) | 2.11 (1.38-3.23) |
| rs4859365 |  | 4 | 35,345,098 | A (0.52/0.45) | 7.72E−05 | 1.49 (1.2-1.86) | 1.24 (1.04-1.47) |
| rs10793832 | FBXL17 | 5 | 107,348,129 | C (0.32/0.26) | 8.13E−05 | 1.11 (0.87-1.41) | 1.47 (1.23-1.76) |
| rs1782134 |  | 14[b] | 40,785,318 | T (0.3/0.25) | 8.18E−05 | 1.68 (1.3-2.18)* | 1.15 (0.96-1.39)* |
| rs11157219 |  | 14[b] | 40,852,451 | G (0.3/0.24) | 8.78E−05 | 1.7 (1.31-2.2)* | 1.16 (0.96-1.4)* |
| rs2302673 | FTO | 16 | 52,625,622 | T (0.87/0.84) | 8.85E−05 | 1.04 (0.76-1.44)* | 1.69 (1.33-2.16)* |
| rs1612945 |  | 14[b] | 40,805,691 | C (0.3/0.24) | 8.91E−05 | 1.66 (1.29-2.15)* | 1.18 (0.98-1.42)* |
| rs1782145 |  | 14[b] | 40,800,126 | C (0.3/0.24) | 9.06E−05 | 1.65 (1.28-2.14)* | 1.18 (0.98-1.42)* |
| rs1782141 |  | 14[b] | 40,795,921 | A (0.3/0.25) | 9.20E−05 | 1.68 (1.3-2.16)* | 1.15 (0.96-1.39)* |
| rs17633211 |  | 11[e] | 108,490,715 | T (0.97/0.94) | 9.33E−05 | 1.9 (1.14-3.15) | 2.09 (1.37-3.19) |
| rs6474413 | CHRNB3 | 8[f] | 42,670,221 | T (0.81/0.76) | 9.36E−05 | 1.18 (0.91-1.53) | 1.54 (1.25-1.9) |
| rs9332406 | CTNNA3 | 10[a] | 68,340,205 | A (0.4/0.34) | 9.71E−05 | 1.63 (1.28-2.06)* | 1.11 (0.94-1.32)* |
| rs1782144 |  | 14[b] | 40,799,523 | G (0.3/0.24) | 9.88E−05 | 1.65 (1.28-2.14)* | 1.18 (0.98-1.43)* |

Legend for Table 17:
*Significantly different Odds Ratio for men and women.
[a] Two Chr 10 SNPs with $r^2$ correlation of 0.89
[b] Nine Chr 14 SNPs with minimum pair-wise $r^2$ correlation of >0.85
[c] Four Chr 9 SNPs with minimum pair-wise $r^2$ correlation of >0.85
[d] Two Chr 5 SNPs with $r^2$ correlation of 0.99 (the other two Chr 5 SNPs are uncorrelated)
[e] Four Chr 11 SNPs with minimum pair-wise $r^2$ correlation of >0.95
[f] Two Chr 8 SNPs with $r^2$ correlation of 1
[g] Two Chr 2 SNPs with $r^2$ correlation of 0.91 (the other two Chr 2 SNPs have pair-wise correlations of <50%).
[h] The risk allele is chosen arbitrarily to be the allele more prevalent in cases to facilitate comparison of effect sizes across SNPs. This does not imply that the effect of the variant is known in any case; the other allele could be protective. In addition, the alleles could be complementary to those reported in dbSNP (see online SNP information).
[i] The allele frequency for rs999 is quite different in these data than reported in dbSNP; this may represent a failure to accurately genotype this SNP in this study.

TABLE 18

All SNPs individually genotyped in the genes NRNX1 and VPS13A

| SNP ID | Chr[a] | Position | Minor Allele Frequency | Risk Allele | p-value[b] | Male Odds Ratio (95% CI) | Female Odds Ratio (95% CI) |
|---|---|---|---|---|---|---|---|
| NRXN1 | | | | | | | |
| afd1260848 | 2 | 50,088,115 | 0.0111 | T | 0.306199180 | 1.16 (0.43-3.13) | 1.91 (0.81-4.50) |
| rs1400882 | 2 | 50,371,747 | 0.4237 | G | 0.366666760 | 1.02 (0.82-1.27) | 1.13 (0.95-1.33) |
| afd743424 | 2 | 50,673,793 | 0.0285 | C | 0.339442817 | 1.5 (0.84-2.79) | 1.13 (0.68-1.88) |
| rs17040897 | 2 | 50,751,878 | 0.0010 | T | 0.435646837 | 0.0 | 2.63 (0.21-33.00) |
| rs17041112 | 2 | 51,064,107 | 0.0278 | A | 0.041036238 | 2.27 (1.04-4.95) | 1.40 (0.88-2.24) |
| afd737192 | 2 | 51,065,341 | 0.0117 | T | 0.038498276 | 3.28 (0.96-11.27) | 1.83 (0.87-3.86) |
| rs12623467 | 2 | 51,136,740 | 0.0607 | C | 0.000014776 | 2.42 (1.51-3.88) | 1.57 (1.14-2.16) |
| rs12467557 | 2 | 51,153,921 | 0.0547 | A | 0.000068795 | 2.53 (1.48-4.31) | 1.62 (1.14-2.30) |
| rs10490162 | 2 | 51,159,308 | 0.1126 | T | 0.000056606 | 1.92 (1.34-2.75) | 1.39 (1.08-1.79) |
| afd736936 | 2 | 51,173,172 | 0.0161 | C | 0.007967325 | 3.50 (1.27-9.67) | 1.79 (0.94-3.39) |

TABLE 18-continued

All SNPs individually genotyped in the genes NRNX1 and VPS13A

| SNP ID | Chr[a] | Position | Minor Allele Frequency | Risk Allele | p-value[b] | Male Odds Ratio (95% CI) | Female Odds Ratio (95% CI) |
|---|---|---|---|---|---|---|---|
| VPS13A | | | | | | | |
| rs10869910 | 9 | 77,053,556 | 0.1982 | T | 0.000490786 | 1.11 (0.84-1.46) | 1.48 (1.21-1.82) |
| rs2022443 | 9 | 77,099,406 | 0.2200 | G | 0.000024860 | 1.12 (0.86-1.45) | 1.57 (1.29-1.91) |
| rs7864334 | 9 | 77,134,110 | 0.4888 | C | 0.004466534 | 0.95 (0.76-1.18) | 1.31 (1.11-1.55) |
| rs11145381 | 9 | 77,144,695 | 0.2093 | C | 0.000047241 | 1.19 (0.91-1.57) | 1.54 (1.26-1.88) |
| rs17423381 | 9 | 77,147,214 | 0.0850 | G | 0.365266659 | 1.30 (0.89-1.90) | 0.96 (0.71-1.30) |
| rs12380218 | 9 | 77,165,214 | 0.2155 | G | 0.000020915 | 1.18 (0.90-1.55) | 1.56 (1.28-1.91) |
| rs11145388 | 9 | 77,179,410 | 0.1857 | T | 0.001001859 | 1.11 (0.84-1.47) | 1.47 (1.19-1.82) |
| rs11145410 | 9 | 77,241,954 | 0.1909 | A | 0.000785556 | 1.19 (9.90-1.57) | 1.45 (1.18-1.78) |

[a]Chromosome;
[b]Primary 2df p-value from the logistic regression analysis

TABLE 19

Distribution of sex, age, FTND score, and recruitment site in cases and controls

| | CASES (N = 1050) | Controls (N = 879) |
|---|---|---|
| SEX | | |
| Males | 44.2% | 30.4% |
| Females | 55.8% | 69.6% |
| AGE (YEARS) | | |
| Mean ± SD | 37.7 ± 6.9 | 36.7 ± 7.5 |
| Range | 25-82 | 25-82 |
| FTND | | |
| Mean ± SD | 6.3 ± 1.7 | 0 |
| SITE | | |
| U.S. | 797 | 713 |
| Australia | 253 | 66 |

TABLE 20

Prevalence of nicotine dependence in monozygotic twins

| Co-Twin Smoking History | Respondent % Nicotine Dependent Among Smokers |
|---|---|
| Never Smoked | 16.67% |
| Smoked 1-2 Times | 4.84% |
| Smoked 3-20 Times | 4.17% |
| Smoked 21-99 Times | 6.52% |
| Smoked 100 Times or More, HSI = 0 | 1.63% |
| Smoked 100 Times or More, HSI = 1 | 2.47% |
| Smoked 100 Times or More, HSI = 2 | 4.79% |
| Smoked 100 Times or More, HSI = 3 | 5.06% |
| Smoked 100 Times or More, HSI = 4 | 50.78% |
| Smoked 100 Times or More, HSI = 5 | 68.42% |
| Smoked 100 Times or More, HSI = 6 | 72.73% |

References For Example 4

1. WHO (2006) (on the internet at www.wpro.who.int/media_centre/fact_sheets/fs_20060530.htm) The facts about smoking and health.
2. CDC (2005) Annual smoking-attributable mortality, years of potential life lost, and productivity losses—United States, 1997-2001. *Morbidity & Mortality Weekly Report,* 54, 625-628.
3. CDC (2005) Cigarette smoking among adults-United States, 2004. *Morbidity & Mortality Weekly Report,* 54, 1121-1124.
4. CDC (2004) Cigarette use among high school students—United States, 1991-2003. *Morbidity & Mortality Weekly Report,* 53, 499.
5. Bierut, L. J., Dinwiddie, S. H., Begleiter, H., Crowe, R. R., Hesselbrock, V., Nurnberger, J. I., Jr., Porjesz, B., Schuckit, M. A. and Reich, T. (1998) Familial transmission of substance dependence: alcohol, marijuana, cocaine, and habitual smoking: a report from the Collaborative Study on the Genetics of Alcoholism. *Arch. Gen. Psychiatry,* 55, 982-988.
6. Carmelli, D., Swan, G. E., Robinette, D. and Fabsitz, R. (1992) Genetic influence on smoking—a study of male twins. *N. Engl. J. Med.,* 327, 829-833.
7. Heath, A. C. and Martin, N. G. (1993) Genetic models for the natural history of smoking: evidence for a genetic influence on smoking persistence. *Addict. Behav.,* 18, 19-34.
8. True, W. R., Xian, H., Scherrer, J. F., Madden, P. A., Bucholz, K. K., Heath, A. C., Eisen, S. A., Lyons, M. J., Goldberg, J. and Tsuang, M. (1999) Common genetic vulnerability for nicotine and alcohol dependence in men. *Arch. Gen. Psychiatry,* 56, 655-661.
9. Madden, P. A., Heath, A. C., Pedersen, N. L., Kaprio, J., Koskenvuo, M. J. and Martin, N. G. (1999) The genetics of smoking persistence in men and women: a multicultural study. *Behav. Genet.,* 29, 423-431.
10. Lessov, C. N., Martin, N. G., Statham, D. J., Todorov, A. A., Slutske, W. S., Bucholz, K. K., Heath, A. C. and Madden, P. A. (2004) Defining nicotine dependence for genetic research: evidence from Australian twins. *Psychol. Med.,* 34, 865-879.
11. Li, M. D., Ma, J. Z., Cheng, R., Dupont, R. T., Williams, N. J., Crews, K. M., Payne, T. J. and Elston, R. C. (2003) A genome-wide scan to identify loci for smoking rate in the Framingham Heart Study population. *BMC Genet.,* 4 Suppl 1, S103.
12. Bierut, L. J., Rice, J. P., Goate, A., Hinrichs, A. L., Saccone, N. L., Foroud, T., Edenberg, H. J., Cloninger, C. R., Begleiter, H., Conneally, P. M. et al. (2004) A genomic scan for habitual smoking in families of alcoholics: common and specific genetic factors in substance dependence. *Am. J. Med. Genet. A,* 124, 19-27.
13. Gelernter, J., Liu, X., Hesselbrock, V., Page, G. P., Goddard, A. and Zhang, H. (2004) Results of a genomewide linkage scan: support for chromosomes 9 and 11 loci increasing risk for cigarette smoking. *Am. J. Med. Genet. B Neuropsychiatr. Genet.,* 128, 94-101.

14. Swan, G. E., Hops, H., Wilhelmsen, K. C., Lessov-Schlaggar, C. N., Cheng, L. S., Hudmon, K. S., Amos, C. I., Feiler, H. S., Ring, H. Z., Andrews, J. A. et al. (2006) A genome-wide screen for nicotine dependence susceptibility loci. *Am. J. Med. Genet. B Neuropsychiatr. Genet.,* 141, 354-360.

15. Li, M. D., Beuten, J., Ma, J. Z., Payne, T. J., Lou, X. Y., Garcia, V., Duenes, A. S., Crews, K. M. and Elston, R. C. (2005) Ethnic- and gender-specific association of the nicotinic acetylcholine receptor alpha4 subunit gene (CHRNA4) with nicotine dependence. *Hum. Mol. Genet.,* 14, 1211-1219.

16. Beuten, J., Ma, J. Z., Payne, T. J., Dupont, R. T., Crews, K. M., Somes, G., Williams, N. J., Elston, R. C. and Li, M. D. (2005) Single- and multilocus allelic variants within the GABA(B) receptor subunit 2 (GABAB2) gene are significantly associated with nicotine dependence. *Am. J. Hum. Genet.,* 76, 859-864.

17. Feng, Y., Niu, T., Xing, H., Xu, X., Chen, C., Peng, S., Wang, L. and Laird, N. (2004) A common haplotype of the nicotine acetylcholine receptor alpha 4 subunit gene is associated with vulnerability to nicotine addiction in men. *Am. J. Hum. Genet.,* 75, 112-121.

18. Saccone, et al., (2006) Cholinergic nicotinic receptor genes implicated in a nicotine dependence association study targeting 348 candidate genes with 3713 SNPs, *Hum. Mol. Genet.,* 16:36-49.

19. Liu, Q. R., Drgon, T., Walther, D., Johnson, C., Poleskaya, O., Hess, J. and Uhl, G. R. (2005) Pooled association genome scanning: validation and use to identify addiction vulnerability loci in two samples. *Proc. Natl. Acad. Sci. U.S.A.,* 102, 11864-11869.

20. Craig, A. M., Graf, E. R. and Linhoff, M. W. (2006) How to build a central synapse: clues from cell culture. *Trends Neurosci.,* 29, 8-20.

21. Iacono, W. G., Carlson, S. R., Malone, S. M. and McGue, M. (2002) P3 event-related potential amplitude and the risk for disinhibitory disorders in adolescent boys. *Arch. Gen. Psychiatry,* 59, 750-757.

22. Dobson-Stone, C., Danek, A., Rampoldi, L., Hardie, R. J., Chalmers, R. M., Wood, N. W., Bohlega, S., Dotti, M. T., Federico, A., Shizuka, M. et al. (2002) Mutational spectrum of the CHAC gene in patients with chorea-acanthocytosis. *Eur. J. Hum. Genet.,* 10, 773-781.

23. Zagranichnaya, T. K., Wu, X. and Villereal, M. L. (2005) Endogenous TRPC1, TRPC3, and TRPC7 proteins combine to form native store-operated channels in HEK-293 cells. *J Biol. Chem.,* 280, 29559-29569.

24. Feng, Z., Li, W., Ward, A., Piggott, B. J., Larkspur, E. R., Sternberg, P. W., Xu, X. Z. (2006) A *c. elegans* model of nicotine-dependent behavior: Regulation by TRP-family channels. *Cell,* 127, 621-633.

25. Ertekin-Taner, N., Ronald, J., Asahara, H., Younkin, L., Hella, M., Jain, S., Gnida, E., Younkin, S., Fadale, D., Ohyagi, Y. et al. (2003) Fine mapping of the alpha-T catenin gene to a quantitative trait locus on chromosome 10 in late-onset Alzheimer's disease pedigrees. *Hum. Mol. Genet.,* 12, 3133-3143.

26. Busby, V., Goossens, S., Nowotny, P., Hamilton, G., Smemo, S., Harold, D., Turic, D., Jehu, L., Myers, A., Womick, M. et al. (2004) Alpha-T-catenin is expressed in human brain and interacts with the Wnt signaling pathway but is not responsible for linkage to chromosome 10 in Alzheimer's disease. *Neuromolecular Med.,* 5, 133-146.

27. Jeulin, C., Guadagnini, R. and Marano, F. (2005) Oxidant stress stimulates Ca2+-activated chloride channels in the apical activated membrane of cultured nonciliated human nasal epithelial cells. *Am. J. Physiol. Lung Cell. Mol. Physiol.,* 289, L636-L646.

28. Hegab, A. E., Sakamoto, T., Uchida, Y., Nomura, A., Ishii, Y., Morishima, Y., Mochizuki, M., Kimura, T., Saitoh, W., Massoud, H. H. et al. (2004) CLCA1 gene polymorphisms in chronic obstructive pulmonary disease. *J. Med. Genet.,* 41, e27.

29. Skol, A. D., Scott, L. J., Abecasis, G. R. and Boehnke, M. (2006) Joint analysis is more efficient than replication-based analysis for two-stage genome-wide association studies. *Nat. Genet.,* 38, 209-213.

30. Breslau, N., Novak, S. P. and Kessler, R. C. (2004) Daily smoking and the subsequent onset of psychiatric disorders. *Psychol. Med.,* 34, 323-333.

31. Breslau, N., Novak, S. P. and Kessler, R. C. (2004) Psychiatric disorders and stages of smoking. *Biol. Psychiatry,* 55, 69-76.

32. Grant, B. F., Hasin, D. S., Chou, S. P., Stinson, F. S. and Dawson, D. A. (2004) Nicotine dependence and psychiatric disorders in the United States: results from the national epidemiologic survey on alcohol and related conditions. *Arch. Gen. Psychiatry,* 61, 1107-1115.

33. Lasser, K., Boyd, J. W., Woolhandler, S., Himmelstein, D. U., McCormick, D. and Bor, D. H. (2000) Smoking and mental illness: A population-based prevalence study. *Jama,* 284, 2606-2610.

34. American Psychiatric Association (1994) *Diagnostic and statistical manual of mental disorders.* 4th ed. American Psychiatric Association, Washington D.C.

35. Breslau, N. and Johnson, E. O. (2000) Predicting smoking cessation and major depression in nicotine-dependent smokers. *Am. J. Public Health,* 90, 1122-1127.

36. Heatherton, T. F., Kozlowski, L. T., Frecker, R. C. and Fagerström, K. O. (1991) The Fagerström Test for Nicotine Dependence: a revision of the Fagerström Tolerance Questionnaire. *Br. J. Addict.,* 86, 1119-1127.

37. Heatherton, T. F., Kozlowski, L. T., Frecker, R. C., Rickert, W. and Robinson, J. (1989) Measuring the heaviness of smoking: using self-reported time to the first cigarette of the day and number of cigarettes smoked per day. *Br. J. Addict.,* 84, 791-799.

38. Pritchard, J. K., Stephens, M. and Donnelly, P. (2000) Inference of population structure using multilocus genotype data. *Genetics,* 155, 945-959.

39. Hinds, D. A., Stokowski, R. P., Patil, N., Konvicka, K., Kershenobich, D., Cox, D. R. and Ballinger, D. G. (2004) Matching strategies for genetic association studies in structured populations. *Am. J. Hum. Genet.,* 74, 317-325.

40. Hinds, D. A., Stuve, L. L., Nilsen, G. B., Halperin, E., Eskin, E., Ballinger, D. G., Frazer, K. A. and Cox, D. R. (2005) Whole-genome patterns of common DNA variation in three human populations. *Science,* 307, 1072-1079.

Example 5

Nicotine Dependence Risk and the Alpha 5 Nicotinic Receptor

Cigarette smoking is a major public health problem that contributes to nearly 5 million deaths every year (WHO, 2006). Despite knowledge of the adverse health effects, 65 million adults in the U.S. continue to smoke and about half of these individuals are dependent on nicotine (Grant et al., 2004). Nicotine is the component in cigarettes that is responsible for the maintenance of smoking, and the physiological effects of nicotine are mediated largely through the neuronal nicotinic acetylcholine receptors (nAChRs).

Our group recently completed a large-scale genome wide association and candidate gene study of nicotine dependence that focused on the contrast between smokers who smoked at least 100 cigarettes in their lifetime, but never developed any symptoms of dependence (See above and Bierut et al, 2007; Saccone et al, 2007). This study design focused on the genetic factors that contribute to this transition from smoking to nicotine dependence. A compelling association finding for follow-up was the identification of genetic variants that results in an amino acid change in the α5 nicotinic receptor (CHRNA5).

The purpose of this study was to further define the genetic contribution of variants in the α5 nicotinic receptor to nicotine dependence, to test if this finding of association replicated in an independent dataset, and to determine if this amino acid change resulted in functional change of the nicotinic receptor.

Materials and Methods
Human Genetic Studies

Two independent datasets were used: NICSNP, a nicotine dependent case and non-dependent smoking controls series and the Collaborative Study of the Genetics of Alcoholism (COGA), a family based study of alcohol dependence, which had high rates of smoking and allowed for the genetic study of heavy and light smoking contrast groups.

NICSNP
Subjects

Subjects (1050 cases and 879 controls) were selected from two ongoing studies: the Collaborative Genetic Study of Nicotine Dependence, a United States based sample (St. Louis, Detroit, and Minneapolis), and the Nicotine Addiction Genetics study, an Australian based, European-Ancestry sample.

The Institutional Review Board approved both studies, and all subjects provided informed consent to participate. Blood samples were collected from each subject for DNA analysis and submitted together with electronic phenotypic data to the NIDA Center for Genetic Studies, which manages the sharing of research data in accordance with NIH guidelines. All subjects were self-identified as being of European descent.

Phenotype Data

Cases were defined by a commonly used definition of nicotine dependence, a Fagerström Test for Nicotine Dependence (FTND) score of 4 or more when smoking the most (maximum score of 10) (Heatherton et al., 1981). Control subject status was defined as an individual who smoked (defined by smoking at least 100 cigarettes during their lifetime), yet never became dependent (lifetime FTND=0).

SNP Genotyping

A custom array to interrogate SNPs in the CHRNA5 gene were selected and genotyped as described as above and in Bierut et al, 2007 and Saccone et al, 2007. Additional quality control measures were put into place with a specification of call rates greater than 95%. The clustering plots for all SNPs were visually inspected to insure discrimination between genotypes. Hardy Weinberg Equilibrium (HWE) was tested separately for cases and controls.

Population Stratification

In order to avoid false positive results due to cryptic population stratification, we performed a STRUCTURE analysis using genotype data for 289 well performing SNPs. This revealed no evidence of population admixture.

Statistical Analysis

For our primary single SNP association analyses, we used logistic regression to incorporate the significant covariates sex and site (U.S., Australia), and tested the effect of genotype together with a genotype-by-sex interaction term using a standard likelihood-ratio chi-squared statistic with 2 degrees of freedom. The full model was compared to a reduced model including gender and recruitment site only, and significance was assessed by a chi square test with 2 degrees of freedom. See above and Saccone et al., 2007 for additional details.

Treescan

Treescanning is an evolutionary tree based method for association analysis and can aid in the interpretation of genetic association results. The software PHASE was used to estimate haplotype phase in 1050 cases and 879 controls for the SNPs covering CHRNA5 (Stephens M et al, AJHG. 2003). PHASE estimated 33 unique haplotypes in this sample. Extremely rare haplotypes (frequencies of less than 0.1%) were removed, then the haplotype network was examined using statistical parsimony in the TCS program (Clement et al., Mol. Ecol. 2000). Haplotypes that showed significant evidence of recombination were then removed (Templeton A R et al, Genetics. 1992). The resulting network was used to assess the association of haplotypes in CHRNA5 with nicotine dependence (Templeton A R et al, Genetics. 2005).

Collaborative Study on the Genetics of Alcoholism
Sample

The Collaborative Study on the Genetics of Alcoholism (COGA) is a multi-site study recruiting families at six centers across the United States: Indiana University, State University of New York Health Science Center, University of Connecticut, University of Iowa, University of California/San Diego, and Washington University, St. Louis (Begleiter et al., 1995; Reich et al., 1998; and Foroud et al., 2000). The institutional review boards of all participating institutions approved the study.

Alcohol dependent probands were identified through inpatient or outpatient chemical dependency treatment programs. Probands and their families were administered a poly-diagnostic instrument, the Semi-Structured Assessment for the Genetics of Alcoholism (SSAGA) interview (Bucholz et al. 1994; Hesselbrock et al. 1999). The families that participated in the genetic phase of this study included a proband and at least two first-degree relatives who met both DSM-IIIR criteria (American Psychiatric Association 1987) for alcohol dependence and Feighner et al. (Feighner et al. 1972) criteria for definite alcoholism.

Though smoking history was assessed, the FTND was not administered, and so comparable nicotine phenotypes were developed. Case status was defined as habitual smoking when an individual smoked at least one pack a day for 6 months or more (Bierut et al., 2004), which was equivalent to at least a score of 3 or more on an FTND scale. A light smoking phenotype was defined as a smoker (smoking daily for at least one month or 100 cigarettes lifetime) who never smoked more than 10 cigarettes daily. Those who never smoked or did not meet the affected or unaffected status were considered "unknown" phenotypically in the analyses.

SNP Genotyping

We used MassArray spectrometry technology was used for genotyping the COGA dataset. PCR primers, termination mixes, and multiplexing capabilities were determined with Sequenom Spectro Designer software v2.00.17. Standard PCR procedures were used to amplify PCR products. All unincorporated nucleotides in the PCR product were deactivated with shrimp alkaline phosphatase. A primer extension reaction was then carried out with the mass extension primer and the appropriate termination mix. The primer extension products were then cleaned with resin and spotted onto a silicon SpectroChip. The chip was scanned with a mass spectrometry workstation (Bruker) and the resulting genotype spectra were analyzed with the Sequenom SpectroTYPER software.

All SNP genotypes were checked for Mendelian inheritance using the program PEDCHECK (O'Connell and Weeks 1998). Marker allele frequencies and heterozygosities were computed separately in the Caucasian and African American families using the program USERM13 (Boehnke 1991). Call rates of greater than 90% and HWE were set as quality control measures.

Statistical Analyses

Statistical analyses were performed using a suite of SAS Macros that utilize SAS/STAT software (SAS 2003) to fit generalized linear mixed models. Because we were analyzing heritable traits, we expected the individuals within a pedigree to be correlated in phenotype as well as genotype. Treating all individuals as unrelated could lead to a bias in the data, especially with respect to large pedigrees. Therefore, we used kinship coefficients weighted by the estimated heritability as the random-effects covariance matrix for this model (Yu et al., 2006). In addition to controlling for the expected correlation between phenotypes, age and gender were incorporated into analyses.

Functional Studies of CHRNA5 Genetic Variant

Cell Culture

HEK293T cells were maintained at 37° C. in a humidified, 5% $CO_2$ environment in Dulbecco's modified Eagle's medium (high glucose, no pyruvate) (DMEM), 10% heat-inactivated fetal bovine serum and antibiotic/antimycotic (100 U/mL penicillin, 100 µg/mL streptomycin and 0.25 µg/mL amphotericin B). Culture reagents were purchased from either Biowhittaker (East Rutherford, N.J., USA) or Invitrogen (Carlsbad, Calif., USA).

Measurement of Intracellular Calcium

Agonist-evoked changes in intracellular calcium was performed using an aequorin-based luminescence assay as previously described (Karadsheh et al., 2004). HEK293T cells were seeded onto six-well plates ($1.5 \times 10^6$ cells/well) and were transfected the following day with plasmids (0.25 µg/well for each plasmid) containing a human codon-optimized aequorin cDNA (Vernon and Printen 2002), the mouse α4 and β2 cDNAs and either the wild-type mouse α5 cDNA (D398) or a mouse α5 cDNA in which D398 was mutated to N398. Transfection was performed using either the LipofectAmine Plus Reagent (Invitrogen) or Fugene HD transfection reagent (Roche, Indianapolis, Ind.) as recommended by the manufacturers. Approximately 48 h following transfection, culture media was replaced with DMEM+0.1% fetal bovine serum and 2.5 mM coelenterizine-hcp (Invitrogen) and the cells were incubated for 3 h at 37° C. in a humidified 5% $CO_2$ incubator. Following the coelenterizine incubation, cells were gently aspirated from the culture dishes and transferred to 2 ml tubes. The cells were then pelleted by centrifugation at 4° C. for 5 min at 800 g, the supernatant was discarded, and the cells were resuspended in 1× assay buffer (Hank's Balanced Salt Solution (Cambrex, East Rutherford, N.J.) supplemented to 10 mM $CaCl_2$). Half the cells were removed for ligand binding, and the remaining cells were again pelleted and subsequently resuspended in fresh 1× assay buffer (500 µl/sample) and incubated for 1 h at 4° C. prior to initiating the assay. Sample size was n=12 for each nAChR variant (12 separate transfections per variant from 3 independent experiments).

For the epibatidine concentration-response curves, 50 µL of cells were added to each well of a 96-well opaque white plate and placed in a Victor3V plate reader (Perkin Elmer). Following a 1 second baseline read, 50 µl epibatidine was injected onto each sample and luminescence was recorded at 0.2 s intervals for 20 s immediately following the addition of agonist. At the completion of the agonist stimulation, 100 µL of a solution containing 0.1% Triton X-100 and 100 mM $CaCl_2$ was injected into each well and luminescence was recorded for 5 s at 0.1 s intervals. In order to control for differences in cell number per well as well as variation in transfection efficiency and coelenterazine loading, agonist responses were normalized by dividing the maximal peak value for the agonist-stimulated luminescence (L) by the total peak luminescence value ($L_{max}$) (maximal peak agonist-stimulated luminescence+maximal peak luminescence resulting from cell lysis in the presence of high calcium).

[$^{125}$I]-Epibatidine Binding

Membrane fractions were prepared from samples as previously described (Marks et al. 1998), with the exception that a 15 minute incubation at 37° C. with 50 µg/mL DNAse was performed prior to the first centrifugation. The binding of [$^{125}$I]-epibatidine to the membrane fractions was performed essentially as described previously (Marks et al., 1998) in a 30 µL reaction that included binding buffer (118 mM NaCl, 4.8 mM KCl, 2.5 mM $CaCl_2$, 1.2 mM $Mg_2SO_4$ and 20 mM HEPES pH 7.5) and 200 pM [$^{125}$I]-epibatidine. Non-specific binding was determined by the inclusion of 10 µM cytisine in the reaction. Ligand binding was performed with an amount of homogenate that did not produce ligand depletion. Homogenate protein levels were determined by the method of Lowry (Lowry et al. 1951).

Data Analysis

Epibatidine-evoked responses were normalized by dividing the functional response ($L/L_{max}$) by the fmol of nAChR per sample well. This normalization provides a response per receptor value. The $EC_{50}$ and maximal response values for the concentration response curves were calculated using a four parameter logistic equation in Graphpad Prism 3.0 software (San Diego, Calif.). Concentration response curves for the two nAChR populations were evaluated using 2-way ANOVA for epibatidine concentration and receptor variant. Maximal response and $EC_{50}$ values between the α4β2α5D398 and α4β2α5N398 were compared using Student's t-test.

Results

Single SNP Association

There was strong evidence of two independent genetic association findings in CHRNA5 with nicotine dependence in the NICSNP sample and habitual smoking in the COGA sample. See Table 21 for results. The most compelling finding was rs6969968, which increased the risk of nicotine dependence in both samples (OR=1.56 (1.28-1.95) p<0.0001 in NICSNP; OR=1.31 (1.14-1.54) p=0.0001). This SNP was common with a minor allele frequency (MAF) of 34-35%, and it marked an amino acid change from aspartic acid (G) to asparagine (A).

Figure 21:
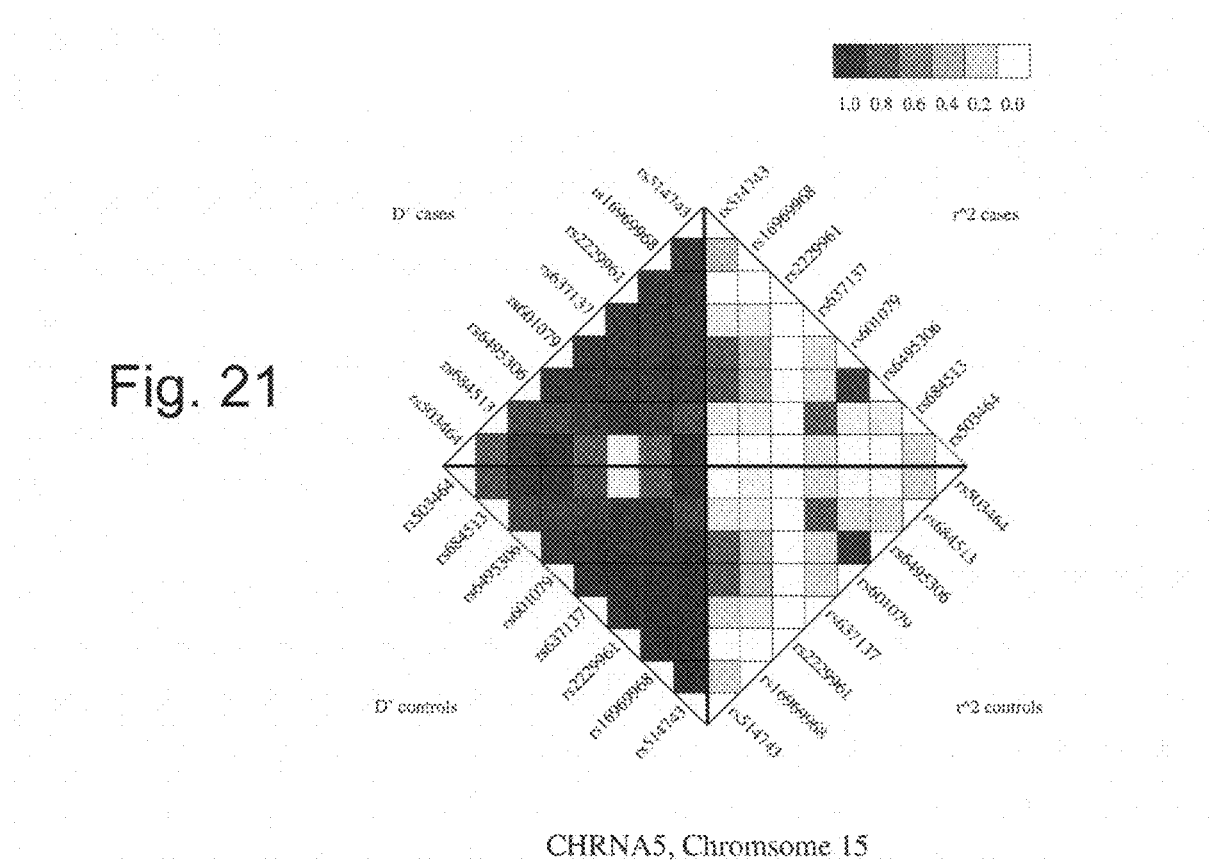
FIG. 21 shows LD and $r^2$ among SNPs in CHRNA5 nicotinic receptor gene.

A second finding was seen in this gene at rs684513, which decreased the risk of developing nicotine dependence (OR=0.79 (0.66-0.94)) in the NICSNP sample. The SNP rs905739 is in high linkage disequilibrium with rs684513 ($r^2$=0.9) and it also showed association. FIG. 21 for linkage disequilibrium across the gene. There was a trend of association with habitual smoking and these SNPs in the COGA sample.

Figure 22:
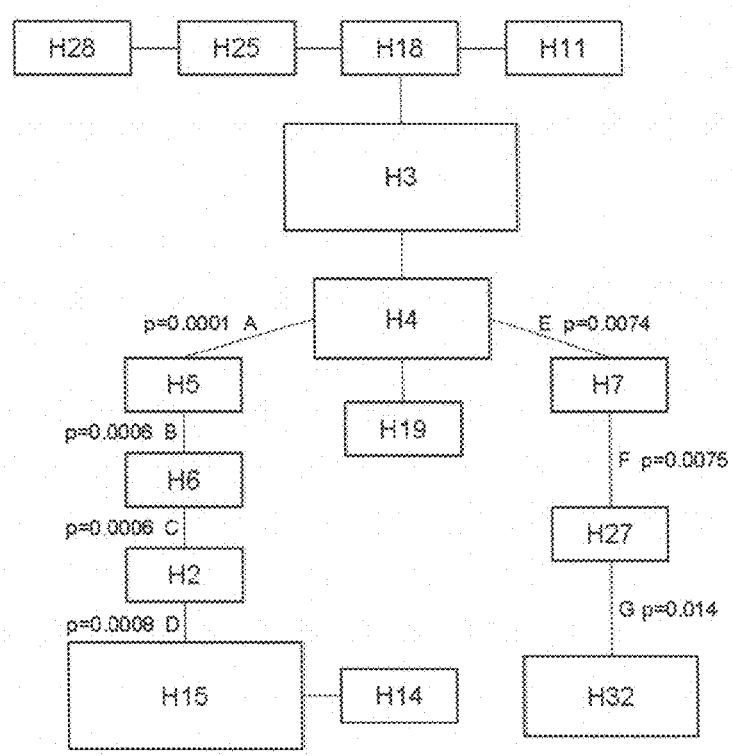
FIG. 22 shows haplotype network for CHRNA5.

To further investigate these findings of association, TREE-SCAN was performed. The treescan identified two main branches, which marked significant association with nicotine addiction (see FIG. 22). The boxes in FIG. 22 represent haplotypes and roughly correlate with haplotype counts. The small boxes have frequencies of below 2%, the medium boxes between 2% and 5%, the medium-large boxes between 5% and 25%, and the large boxes above 25%. Branch A is marked by a change from G in H4 to A in H5 at rs16969968. Branch B is marked by a change from C in H5 to A in H6 at rs601079. Branch C is marked by a change from C in H6 to T in H2 at rs2036527. Branch D is marked by a change from A in H2 to G in H15 at rs880395. Branch E is marked by a change from C in H4 to A in H7 at rs601079 and a change from T in H4 to A in H7 at rs637137. Branch F is marked by a change from A in H7 to G in H32 at both rs880395 and rs905739. Branch G is marked by a change from C in H7 to G in H32 at rs684513 P-values from the treescan at these branches are also shown. The branch A between H4 and H5 is defined by the amino acid change at rs16969968. A transition from G to A defined a haplotype group with increased risk for nicotine addiction, and the association at the branch marked was very strong (p=0.0001). This effect remained when conditioning upon the effects defined by branch E (p=0.004). The second haplotype grouping demonstrated a decreased risk for nicotine addiction. The reduced risk haplotype group was on the "protective" G allele background for rs16969968 (p values p.014-p.0074). After conditioning on the effects of the A branch, this association was no longer significant, though this may be due to a loss of power. Thus, two genetic effects in the a5 nicotinic receptor that may contribute to nicotine dependence were identified—the amino acid change at rs16969968 which is a risk variant and a second protective haplotype group.

Figure 24:
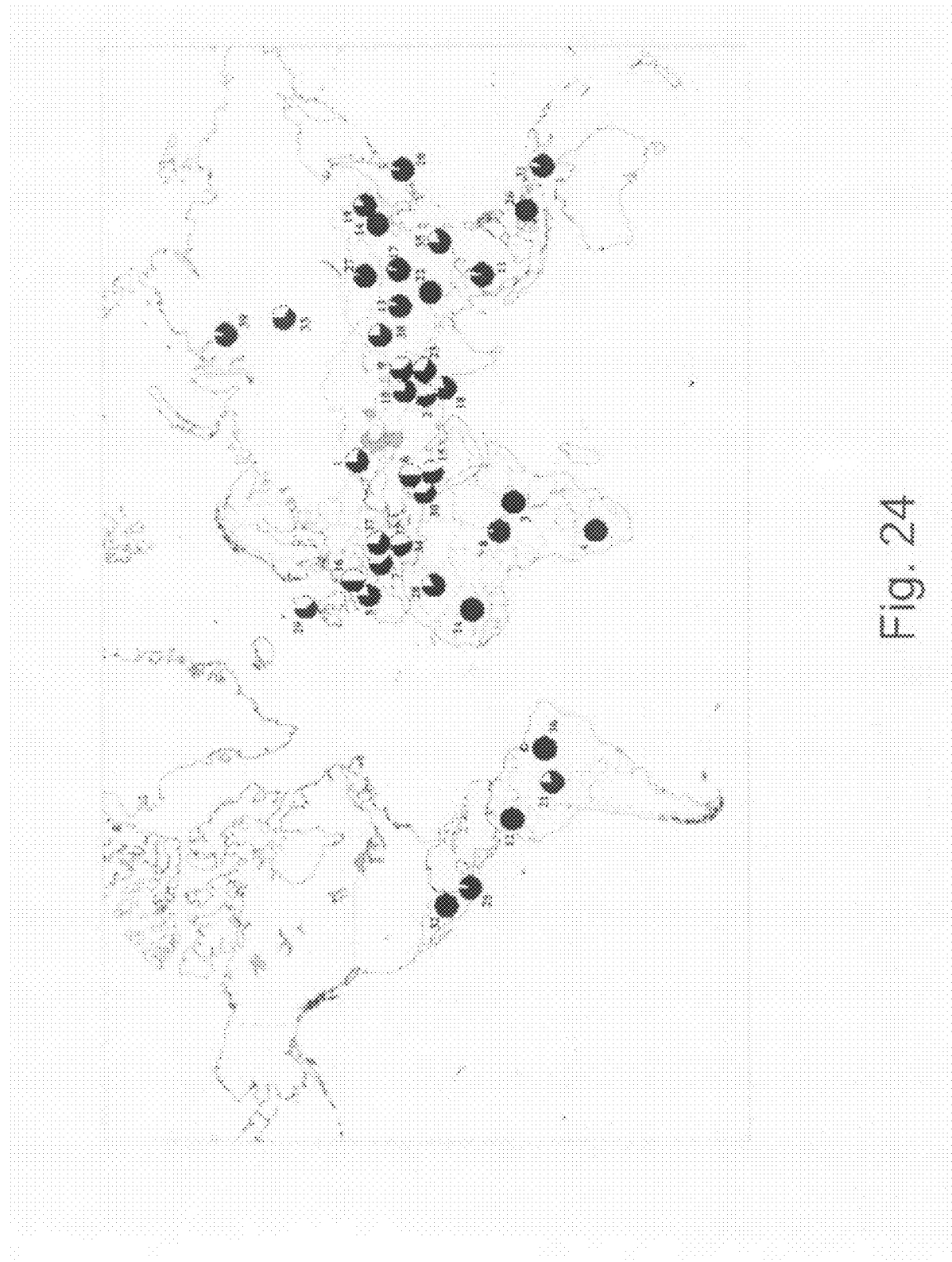
FIG. 24 shows distribution of A allele of rs16969968.

We further examined rs16969968 across species using bioinformatics databases (Reference). See FIG. 23. The aspartic acid residue at amino acid position 398 was highly conserved further suggesting its functional importance. To assess the distribution of the minor allele, A allele, of rs16969968 across multiple populations, we typed this SNP in the HGDP-CEPH Human Genome Diversity Cell Line Panel, which includes 995 individuals representing 52 different populations (Cann et al., 2002). In Caucasian populations, the A allele ranged from 21% to 50% with the exception of Yakut population (MAF=0.06). The A allele was not detected or uncommon in African and Asian population. See FIG. 24 for a geographic distribution of allele frequencies.

Figure 25:
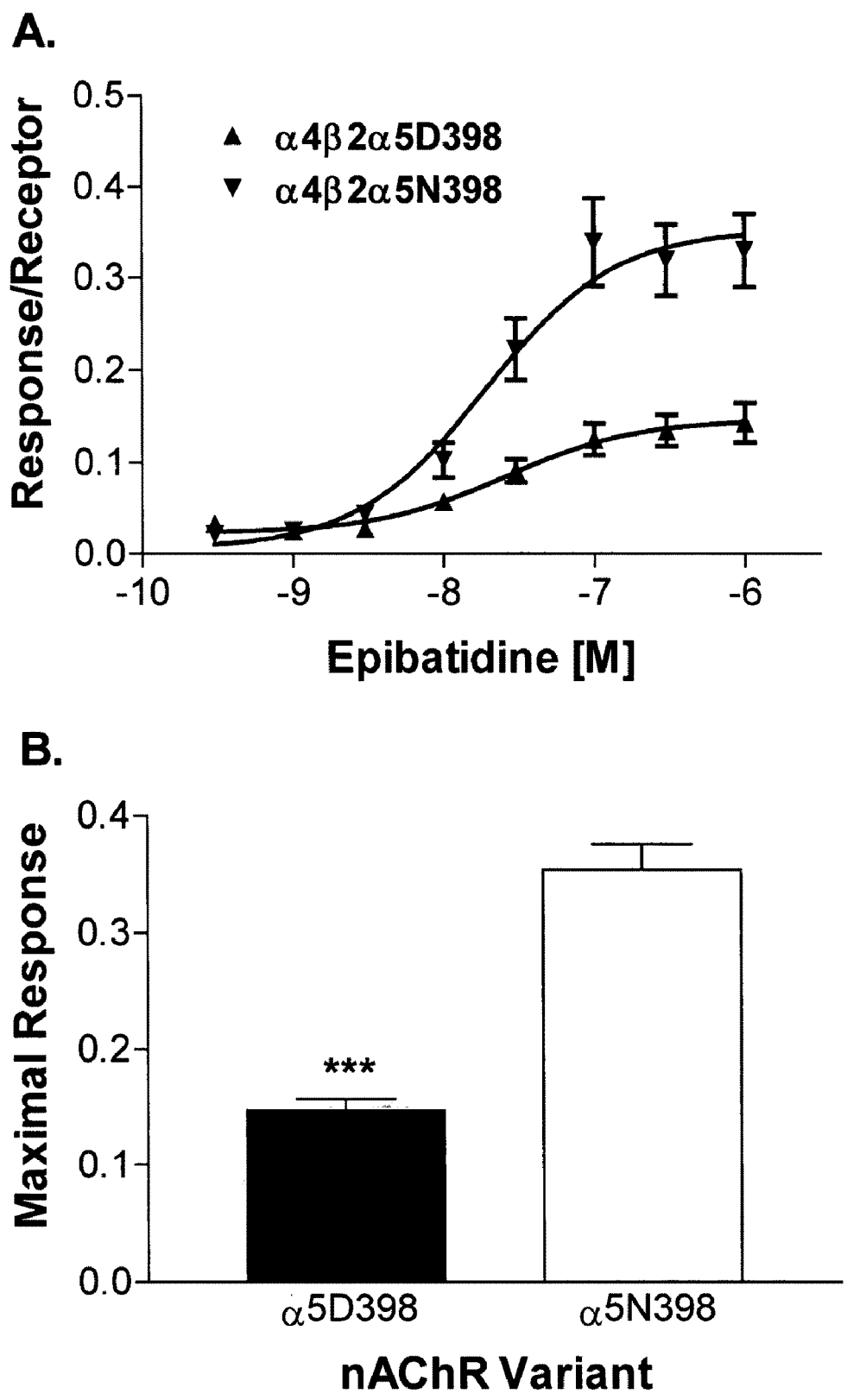
FIG. 25 A shows the concentration response curve and FIG. 25 B shows the maximal response to agonist per receptor.

To establish whether the D398N polymorphism altered nAChR function, nicotinic agonist-evoked changes in intracellular calcium were measured from HEK293T cells that heterologously expressed either α4β2α5D398 or α4β2α5N398 nAChRs. Receptor levels were determined for each sample in order to normalize agonist responses to receptor numbers. Two-way ANOVA indicated that the concentration response curves for the nicotinic agonist epibatidine were significantly different between the α4β2α5N398 and α4β2α5D398 variants (p<0.0001). The maximal response to agonist per receptor was found to be over two-fold higher for the α4β2α5N398 nAChR variant relative to the α4β2α5D398 nAChR variant (0.356±0.022 and 0.147±0.01, respectively; p<0.0005). FIG. 25 shows that the CHRNA5 D398N polymorphism affects nAChR function. Panel A shows concentration-response curves for epibatidine evoked changes in intracellular calcium measured from HEK293T cells transfected with plasmids containing a calcium sensing aequorin cDNA, α4 and β2 cDNAs and either α5D398 or α5N398 cDNA. Receptor levels were also determined for each sample using [$^{125}$I]epibatidine and agonist responses were normalized per fmol receptors. Panel B shows nAChRs possessing the N398 variant of α5 which exhibited a significantly greater maximal response to epibtidine as compared to nAChRs containing the D398 variant. The variant nAChR populations did not differ in $EC_{50}$ values for epibatidine. For FIG. 25, N=12 for each nAChR variant and the data shown were mean ±SEM and ***p<0.0005. This difference in concentration-responses curves and maximal response to agonist was not due to a shift in sensitivity to activation by epibatidine between the nAChR variants as their $EC_{50}$ values did not differ (α4β2α5D398 $EC_{50}$=25.9±1.5 pM; α4β2α5N398 $EC_{50}$=19.1±1.4 pM, p=0.25).

Discussion

This study demonstrated that an amino acid change in the α5 nicotinic receptor increased a smoker's risk of transitioning to dependence, and this finding was replicated in an independent sample. In addition, this amino acid change results in altered function of the nicotinic receptor.

The frequency of this amino acid change varies across the different ethnic/racial group. The "at risk" genotype is predominantly seen in populations of European descent and was uncommon or non-existent in populations of Asian or African origin. These findings suggest that this SNP is a much more significant risk factor for nicotine dependence among populations of European origin compared to other populations and different genetic risk factors play a more important role in other ethnic/racial groups.

The region where this amino acid change lies in the α5 receptor is highly conserved across species from mouse, rat, chicken, monkey, and chimpanzee with an aspartic acid in this location. In man, the amino acid may be either an aspartic acid or asparagine. The asparagine substitution resulted in an increased response of the α4β2α5 receptors in in vitro studies and was associated with the increase risk of developing nicotine dependence.

The α5 subunit combines with α4β2 receptors to form the pentameric receptor which is expressed in dopamine cells in the striatum. This region of the brain is associated with the reward pathway involved in dependence and the neurotransmitter dopamine plays a crucial role in the development of dependence. This converging biologic data adds additional support to our findings of the important role of CHRNA5 in the development of nicotine dependence.

There is evidence of a second genetic variant occurring with this gene that is a "protective" variant. It is unknown what the functional role this variant may be. It is also important to note that these associated SNPs are in strong linkage disequilibrium with SNPs in the alpha 3 gene, and so the functional effect may be in the alpha 3 gene.

In summary, this example provides strong evidence for an amino acid change in the alpha 5 nicotinic receptor results in functional changes, which increase an individual's risk of transitioning from being a smoker to becoming dependent on nicotine. This variant is common in populations of European descent and increases the risk of developing nicotine dependence, or conversely the ancestral variant protects against transitioning from smoking to dependence. These results support the role of the alpha 5 nicotinic receptor in the pharmacogenetic response to nicotine, which leads to dependence and provide further biologic insights into the development of dependence Table 21

| | | Risk | NICSNP | | | COGA Kinmix | | |
|---|---|---|---|---|---|---|---|---|
| SNP | Position | Allele[1] | MAF | OR (95% CI) | p | MAF | OR (95% CI) | p |
| rs1979906 | 76629344 | G | | | | 0.44 | 0.89 (0.73-1.08) | 0.2270 |
| rs880395 | 76631411 | A | 0.42 | 0.95 (0.82-1.09) | 0.4591 | 0.43 | 0.86 (0.70-1.07) | 0.1776 |
| rs7164030 | 76631716 | G | 0.43 | 0.94 (0.81-1.08) | 0.3748 | 0.43 | 0.85 (0.69-1.06) | 0.1499 |
| rs905739 | 76632165 | C | 0.22 | 0.77 (0.65-0.91) | 0.0030 | 0.23 | 0.87 (0.68-1.10) | 0.2406 |
| rs2036527 | 76638670 | T | 0.36 | 1.29 (1.11-1.50) | 0.0007 | 0.33 | 1.34 (1.07-1.67) | 0.0103 |
| rs3841324 | 76644877 | WT | | | | | 1.15 (0.94-1.29) | 0.1823 |
| rs503464 | 76644951 | A | 0.07 | 0.86 (0.62-1.20) | 0.3776 | 0.23 | 0.82 (0.65-1.03) | 0.0811 |
| rs684513 | 76645455 | G | 0.21 | 0.79 (0.66-0.94) | 0.0082 | 0.21 | 0.85 (0.66-1.08) | 0.1830 |
| rs667282 | 76650527 | G | 0.22 | 0.76 (0.64-0.91) | 0.0022 | 0.24 | 0.81 (0.65-1.01) | 0.0650 |
| rs6495306 | 76652948 | G | 0.43 | 0.95 (0.82-1.09) | 0.4716 | | | |
| rs17486278 | 76654537 | C | | | | 0.32 | 1.43 (1.14-1.79) | 0.0019 |
| rs601079 | 76656634 | T | 0.43 | 0.95 (0.82-1.09) | 0.4756 | 0.43 | 0.89 (0.73-1.09) | 0.2554 |
| rs680244 | 76658343 | A | | | | 0.43 | 0.92 (0.76-1.13) | 0.4427 |
| rs621849 | 76659916 | G | | | | 0.43 | 0.91 (0.75-1.11) | 0.3597 |
| rs569207 | 76660174 | A | | | | 0.24 | 0.78 (0.62-0.98) | 0.0314 |
| rs637137 | 76661031 | A | 0.22 | 0.75 (0.63-0.89) | 0.0010 | | | |
| rs692780 | 76663560 | G | | | | 0.37 | 0.94 (0.77-1.15) | 0.5639 |
| rs10519205 | 76665846 | T | | | | 0.00 | 1.16 (0.16-8.36) | 0.8812 |
| rs2229961 | 76667807 | A | 0.02 | 1.65 (0.96-2.84) | 0.0706 | | | |
| rs16969968 | 76669980 | A | 0.35 | 1.31 (1.13-1.52) | 0.0003 | 0.33 | 1.47 (1.18-1.83) | 0.0006 |
| rs514743 | 76671282 | A | 0.37 | 1.01 (0.87-1.17) | 0.9180 | 0.37 | 0.94 (0.77-1.15) | 0.5576 |

Summary of Logistirc Regression Analyses* of CHRNA5 SNPs with Nicotine Dependence in NICSNP and Habitual Smoking in COGA.

SNP effects modeled using KINMIX in COGA Families. Blank table entries under NICSNP and COGA indicate that the SNP was not genotyped in the correpsonding dataset.
[1]The common allele is the reference allele and the minor allele is the risk allele.
[2]rs3841324 is an indel; the 22 base-pair deletion is the reference and the wild type is the risk.

References For Example 5

1. Karadsheh, M. S., Shah, M. S., Tang, X., Macdonald, R. L., & Stitzel, J. A. Functional characterization of mouse alpha4beta2 nicotinic acetylcholine receptors stably expressed in HEK293T cells. *J. Neurochem.* 91, 1138-1150 (2004).
2. Lowry, O. H., Rosebrough, N. J., Farr, A. L., & Randall, R. J. Protein measurement with the Folin phenol reagent. *J. Biol. Chem.* 193, 265-275 (1951).
3. Marks, M. J., Smith, K. W., & Collins, A. C. Differential agonist inhibition identifies multiple epibatidine binding sites in mouse brain. *J. Pharmacol. Exp. Ther.* 285, 377-386 (1998).
4. Vernon, W. I. & Printen, J. A. Assay for intracellular calcium using a codon-optimized aequorin. *Biotechniques* 33, 730, 732, 734 (2002).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method for identifying a human individual with an increased risk for nicotine addiction, the method comprising; obtaining a biological sample comprising nucleic acid from the human individual, detecting, in the biological sample, the allele present at the rs16969968 polymorphism site on each chromosome, and determining that the human individual has an increased risk for nicotine addiction if the human individual has an A allele present on each chromosome at the rs16969968 polymorphism site compared to a human individual with one A allele or no A alleles at the rs16969968 polymorphism site.

2. The method of claim 1, wherein the detecting comprises amplifying a sequence comprising the allele present at the rs16969968 polymorphism site to generate an amplicon, and detecting the amplicon.

3. The method of claim 2, wherein the amplifying comprises:

I. admixing a primer or a primer pair with a nucleic acid template isolated from the biological sample, wherein the primer or the primer pair is complementary or partially complementary to a region proximal to or including the rs16969968 polymorphism site, and is capable of initiating nucleic acid polymerization by a polymerase on the nucleic acid template; and, II. extending the primer or the primer pair in a DNA polymerization reaction comprising a polymerase and the nucleic acid template to generate an amplicon.

4. The method of claim 2, wherein the amplicon is detected by a process that includes one or more of: hybridizing the amplicon to an array, digesting the amplicon with a restriction enzyme, or real-time PCR analysis.

5. The method of claim 2, comprising partially or fully sequencing the amplicon.

6. The method of claim 2, wherein the amplifying comprises performing a polymerase chain reaction (PCR), reverse transcriptase PCR (RT-PCR), or ligase chain reaction (LCR) using nucleic acid isolated from the biological sample as a template in the PCR, RT-PCR, or LCR.

* * * * *

SEQUENCE LISTING

<160> NUMBER OF SEQ ID NOS: 7

<210> SEQ ID NO 1
<211> LENGTH: 44
<212> TYPE: PRT
<213> ORGANISM: Homo sapiens

<400> SEQUENCE: 1

Lys Glu Glu Thr Glu Ser Gly Ser Gly Pro Lys Ser Ser Arg Asn Thr
1               5                   10                  15

Leu Glu Ala Ala Leu Asp Ser Ile Arg Tyr Ile Thr Arg His Ile Met
            20                  25                  30

Lys Glu Asn Asp Val Arg Glu Val Val Glu Asp Trp
        35                  40

```
<210> SEQ ID NO 2
<211> LENGTH: 44
<212> TYPE: PRT
<213> ORGANISM: Pan troglodytes

<400> SEQUENCE: 2

Lys Glu Glu Thr Glu Ser Gly Ser Gly Pro Lys Ser Ser Arg Asn Thr
1               5                   10                  15
Leu Glu Ala Ala Leu Asp Ser Val Arg Cys Ile Thr Arg His Ile Met
            20                  25                  30
Lys Glu Asn Asp Val Arg Glu Val Val Glu Asp Trp
        35                  40

<210> SEQ ID NO 3
<211> LENGTH: 43
<212> TYPE: PRT
<213> ORGANISM: Saimiri boliviensis

<400> SEQUENCE: 3

Glu Gln Thr Gly Ser Gly Gly Gly Pro Glu Ser Ser Arg Asn Thr Met
1               5                   10                  15
Glu Ala Ala Leu Asp Ser Ile Arg Tyr Ile Thr Arg His Ile Val Lys
            20                  25                  30
Glu Asn Ala Val Arg Glu Val Val Glu Asp Trp
        35                  40

<210> SEQ ID NO 4
<211> LENGTH: 44
<212> TYPE: PRT
<213> ORGANISM: Bos sp.

<400> SEQUENCE: 4

Lys Glu Glu Ala Arg Ser Ser Arg Gly Pro Arg Ser Ser Arg Asn Ala
1               5                   10                  15
Leu Glu Ala Ala Leu Asp Ser Val Arg Tyr Ile Thr His Val Met
            20                  25                  30
Lys Glu Thr Asp Val Arg Glu Val Val Glu Asp Trp
        35                  40

<210> SEQ ID NO 5
<211> LENGTH: 43
<212> TYPE: PRT
<213> ORGANISM: Rattus sp.

<400> SEQUENCE: 5

Arg Glu Glu Ala Glu Ser Gly Ala Gly Pro Lys Ser Arg Asn Thr Leu
1               5                   10                  15
Glu Ala Ala Leu Asp Cys Ile Arg Tyr Ile Thr Arg His Val Val Lys
            20                  25                  30
Glu Asn Asp Val Arg Glu Val Val Glu Asp Trp
        35                  40

<210> SEQ ID NO 6
<211> LENGTH: 43
<212> TYPE: PRT
<213> ORGANISM: Mus sp.

<400> SEQUENCE: 6

Arg Glu Glu Ala Glu Lys Asp Gly Gly Pro Lys Ser Arg Asn Thr Leu
1               5                   10                  15
Glu Ala Ala Leu Asp Cys Ile Arg Tyr Ile Thr Arg His Val Val Lys
            20                  25                  30
```

```
Glu Asn Asp Val Arg Glu Val Val Glu Asp Trp
        35                  40

<210> SEQ ID NO 7
<211> LENGTH: 44
<212> TYPE: PRT
<213> ORGANISM: Gallus gallus

<400> SEQUENCE: 7

Lys Glu Glu Lys Gly Asn Met Ser Gly Ser Glu Ser Ser Arg Asn Thr
1               5                   10                  15

Leu Glu Ala Ala Leu Asp Ser Ile Arg Tyr Ile Thr Arg His Val Met
            20                  25                  30

Lys Glu Asn Glu Val Arg Glu Val Val Glu Asp Trp
        35                  40
```